United States Patent
Urch et al.

(10) Patent No.: US 11,261,177 B2
(45) Date of Patent: Mar. 1, 2022

(54) BENZOXAZINONE DERIVATIVES USEFUL AS HERBICIDES

(71) Applicant: REDAG CROP PROTECTION LTD, Wigan (GB)

(72) Inventors: Christopher John Urch, Wigan (GB); Victoria Elizabeth Jackson, Wigan (GB); Calum William Muir, Wigan (GB)

(73) Assignee: REDAG CROP PROTECTION LTD, Wigan (GB)

( * ) Notice: Subject to any disclaimer, the term of this patent is extended or adjusted under 35 U.S.C. 154(b) by 238 days.

(21) Appl. No.: 16/628,332

(22) PCT Filed: Jul. 23, 2018

(86) PCT No.: PCT/GB2018/052078
§ 371 (c)(1),
(2) Date: Jan. 3, 2020

(87) PCT Pub. No.: WO2019/020987
PCT Pub. Date: Jan. 31, 2019

(65) Prior Publication Data
US 2020/0172527 A1   Jun. 4, 2020

(30) Foreign Application Priority Data

Jul. 24, 2017 (GB) .................... 1711839
Jan. 30, 2018 (GB) .................... 1801491

(51) Int. Cl.
| C07D 413/10 | (2006.01) |
|---|---|
| C07D 471/04 | (2006.01) |
| C07D 487/04 | (2006.01) |
| C07D 498/04 | (2006.01) |
| C07D 513/04 | (2006.01) |
| A01N 43/90 | (2006.01) |

(52) U.S. Cl.
CPC .......... *C07D 413/10* (2013.01); *A01N 43/90* (2013.01); *C07D 471/04* (2013.01); *C07D 487/04* (2013.01); *C07D 498/04* (2013.01); *C07D 513/04* (2013.01)

(58) Field of Classification Search
None
See application file for complete search history.

(56) References Cited

U.S. PATENT DOCUMENTS

| 4,640,707 A | 2/1987 | Nagano et al. |
|---|---|---|
| 2012/0214668 A1 | 8/2012 | Witschel et al. |
| 2013/0184155 A1 | 7/2013 | Newton et al. |
| 2014/0329682 A1 | 11/2014 | Ikeda |
| 2015/0250181 A1 | 12/2015 | Witschel et al. |

FOREIGN PATENT DOCUMENTS

CN   105061416 A   11/2015

OTHER PUBLICATIONS

Search Report Under 17(5), for International Application No. GB1711839.9, dated Jan. 23, 2018, 3 pages.
International Search Report and Written Opinion issued in corresponding to International Application No. PCT/GB2018/052078, dated Sep. 17, 2018, 13 pages.

*Primary Examiner* — Alton N Pryor
(74) *Attorney, Agent, or Firm* — Morgan, Lewis & Bockius LLP

(57) ABSTRACT

The present invention relates to compounds which are of use in the field of agriculture as herbicides. The compounds in question are of formula II and comprise a spirofused tricycle core: wherein $R^4$ and $R^5$ together with the carbon atom to which they are attached form a cyclic group.

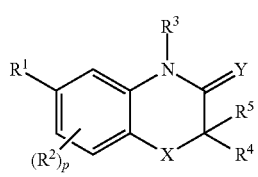

II

21 Claims, No Drawings

BENZOXAZINONE DERIVATIVES USEFUL AS HERBICIDES

This application is the U.S. national stage application of International (PCT) Patent Application Serial No. PCT/GB2018/052078, filed Jul. 23, 2018, which claims the benefit of and priority to GB Application No. 1711839.9, filed Jul. 24, 2017, and GB Application No. 1801491.0, filed Jan. 30, 2018. The entire disclosure of each of these applications is hereby incorporated by reference.

The present invention relates to compounds which are of use in the field of agriculture as herbicides.

Given the global increase in demand for food, there is an international need for new treatments to reduce food crop losses to disease, insects and weeds. Over 40% of crops are lost before harvest worldwide. Losses have actually increased since the mid-1990s.

EP0170191, EP0176101, EP0640600 and WO2010145992 describe benzoxazinone compounds that are useful as herbicides.

It is an aim of certain embodiments of the invention to provide herbicidal compounds that are more active than prior art compounds. It is an aim of certain embodiments of the invention to provide herbicidal compounds that are more selective than prior art compounds, i.e. they may have better, similar or even lower activity than prior art compounds against target plant species but are significantly less active against non-target plant species (e.g. the crops which are being protected).

This invention provides compounds that achieve one or more of the above aims.

SUMMARY OF THE INVENTION

In a first aspect of the invention is provided a compound of formula I:

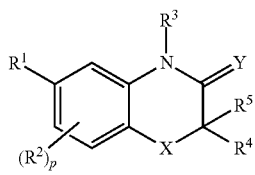

wherein
X is independently selected from $CR^6R^7$, $NR^8$, O, S, S(O) and $S(O)_2$;
Y is independently selected from O and S;
$R^1$ is independently a 5- to 7-membered heterocyclyl group; wherein said heterocyclyl group comprises at least one nitrogen atom in the ring; wherein said heterocyclyl group is optionally unsaturated and is optionally fused to either: a second ring selected from benzene, 5- or 6-membered heteroaryl, $C_3$-$C_6$-cycloalkyl and 5- to 7-membered heterocycloalkyl; or a bridged bicyclic ring system; wherein $R^1$ is optionally substituted with from 1 to 6 $R^9$ groups;
or wherein $R^1$ is —N=$CR^{10}R^{11}$ wherein $R^{10}$ and $R^{11}$ together with the carbon atom to which they are attached form a 5- to 9-membered bicyclic or monocyclic heterocyclyl group, wherein said heterocyclyl group is optionally unsaturated; and wherein said heterocyclyl group comprises at least one nitrogen atom in the ring and is optionally substituted with from 1 to 6 $R^9$ groups; $R^2$ is independently at each occurrence selected from $C_1$-$C_6$-alkyl, $C_1$-$C_6$-haloalkyl, halogen, nitro, $OR^{12}$, $SR^{13}$, $OS(O)_2R^{13}$, $S(O)_2R^{13}$, $S(O)_2NR^{13}R^{13}$, $S(O)(NR^{13})R^{13}$, $S(O)R^{13}$, cyano, $C_2$-$C_6$-alkenyl, $C_2$-$C_6$-alkynyl, and $NR^{13}R^{14}$;
$R^3$ is selected from $C_1$-$C_6$-alkyl, $C_1$-$C_6$-haloalkyl, $C_3$-$C_6$-cycloalkyl, $C_3$-$C_6$-alkenyl, $C_3$-$C_6$-alkynyl, 4- to 6-membered heterocycloalkyl, $C_2$-$C_3$-alkylene-$OR^{13a}$ and $C_1$-$C_3$-alkylene-$R^{3a}$; wherein $R^{3a}$ is selected from: cyano, 3- to 6-membered heterocycloalkyl, $C_3$-$C_6$-cycloalkyl and $CO_2R^{13a}$;
$R^4$ and $R^5$ together with the carbon atom to which they are attached form a cyclic group selected from $C_3$-$C_6$-cycloalkyl and a 4- to 6-membered heterocycloalkyl, wherein said heterocycloalkyl group comprises at least one heteroatom selected from N, O and S; and wherein said cycloalkyl group and heterocycloalkyl group is optionally substituted with from 1 to 4 $R^{15}$ groups;
$R^6$, $R^7$ and $R^8$ are each independently selected from H, $C_1$-$C_6$-alkyl and $C_3$-$C_6$-cycloalkyl;
$R^9$ is independently at each occurrence selected from: =O, =S, =$NR^{13}$, $C_1$-$C_6$-alkyl, $C_1$-$C_6$-haloalkyl, halogen, nitro, $OR^{12}$, $SR^{13}$, $S(O)_2R^{13}$, $S(O)_2NR^{13}R^{13}S(O)(NR^{13})R^{13}$, $S(O)R^{13}$, $C(O)R^{13}$, $C(O)NR^{13}R^{13}$, $C(O)OR^{13}$, cyano, $C_2$-$C_6$-alkenyl, $C_2$-$C_6$-alkynyl, and $NR^{13}R^{14}$;
$R^{12}$ is independently at each occurrence selected from: H, $C_1$-$C_6$-alkyl, $C_3$-$C_6$-cycloalkyl, $C_1$-$C_6$-haloalkyl and 4- to 6-membered heterocycloalkyl;
$R^{13}$ is independently at each occurrence selected from: H, benzyl, $C_3$-$C_6$-cycloalkyl and $C_1$-$C_6$-alkyl;
or where two $R^{13}$ groups are attached to the same nitrogen atom, said $R^{13}$ groups, together with said nitrogen atom form a 4-, 5-, 6- or 7-membered heterocycloalkyl ring;
$R^{13a}$ is independently selected from: H, $C_3$-$C_6$-cycloalkyl and $C_1$-$C_6$-alkyl;
$R^{14}$ is independently at each occurrence selected from; H, benzyl, $C_1$-$C_6$-alkyl, $C_3$-$C_6$-cycloalkyl, C(O)—$C_1$-$C_6$-alkyl, $S(O)_2$—$C_1$-$C_6$-alkyl and 4- to 6-membered heterocycloalkyl;
or where a $R^{13}$ group and a $R^{14}$ group are attached to the same nitrogen atom, said $R^{13}$ and $R^{14}$ groups, together with said nitrogen atom form a 4-, 5-, 6- or 7-membered heterocycloalkyl ring;
$R^{15}$ is independently at each occurrence selected from: =O, =S, =$NR^{13}$, $C_1$-$C_6$-alkyl, $C_1$-$C_6$-haloalkyl, halogen, nitro, $OR^{12}$, $SR^{13}$, $S(O)_2R^{13}$, $S(O)_2NR^{13}R^{13}$, $S(O)(NR^{13})R^{13}$, $S(O)R^{13}$, $C(O)R^{13}$, $C(O)NR^{13}R^{13}$, $C(O)OR^{13}$, cyano, $C_2$-$C_6$-alkenyl, $C_2$-$C_6$-alkynyl, and $NR^{13}R^{14}$;
p is an integer selected from 0, 1, 2 and 3;
wherein any $R^2$, $R^3$, $R^6$, $R^7$, $R^8$, $R^9$, $R^{12}$, $R^{13}$ or $R^{14}$ group that is alkyl, alkenyl, alkynyl, cycloalkyl, heterocycloalkyl (including where two $R^{13}$ groups or an $R^{13}$ group and an $R^{14}$ group together with a nitrogen to which they are attached form a heterocycloalkyl ring), or alkylene-cycloalkyl is optionally substituted, where chemically possible, by 1 to 4 substituents which are each independently selected at each occurrence from the group consisting of: =O; =$NR^a$, =$NOR^a$, $C_1$-$C_4$-alkyl, halo, nitro, cyano, $C_1$-$C_4$-haloalkyl, $C_2$-$C_4$-alkenyl, $C_2$-$C_4$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$ and $OR^a$;
wherein $R^a$ is independently selected from H and $C_1$-$C_4$-alkyl; and $R^b$ is independently H, $C_1$-$C_4$-alkyl, C(O)—$C_1$-$C_4$-alkyl, $S(O)_2$—$C_1$-$C_4$-alkyl; or an agronomically acceptable salt or N-oxide thereof.

In another aspect of the invention, is provided a compound of formula II:

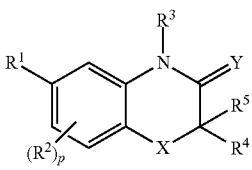

wherein
X is independently selected from $CR^6R^7$, $NR^8$, O, S, S(O) and $S(O)_2$;
Y is independently selected from O and S;
$R^1$ is independently selected from:

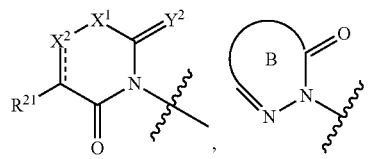

and $-N=CR^{10}R^{11}$; wherein $R^{10}$ and $R^{11}$ together with the carbon atom to which they are attached form a 5- to 9-membered bicyclic or monocyclic heterocyclyl group, wherein said heterocyclyl group is optionally unsaturated; and wherein said heterocyclyl group comprises at least one nitrogen atom in the ring and is optionally substituted with from 1 to 6 $R^9$ groups;
wherein ===== is either a double bond or a single bond;
$=Y^2$ is =O or =S;
$X^1$ is independently absent or is selected from $NR^{19}$ and $CR^{22}R^{22}$;
$X^2$ is independently absent or is $CR^{21}$;
ring B is a 5- or 6-membered heterocyclyl group; and wherein said heterocyclyl group is optionally fused to a 5- or 6-membered cycloalkyl or heterocycloalkyl ring and wherein the group $R^1$ is optionally substituted with from 1 to 5 $R^9$ groups;
$R^2$ is independently at each occurrence selected from $C_1$-$C_6$-alkyl, $C_1$-$C_6$-haloalkyl, halogen, nitro, $OR^{12}$, $SR^{13}$, $OS(O)_2R^{13}$, $S(O)_2R^{13}$, $S(O)_2NR^{13}R^{13}$, $S(O)(NR^{13})R^{13}$, $S(O)R^{13}$, cyano, $C_2$-$C_6$-alkenyl, $C_2$-$C_6$-alkynyl, and $NR^{13}R^{14}$;
$R^3$ is selected from $C_1$-$C_6$-alkyl, $C_1$-$C_6$-haloalkyl, $C_3$-$C_6$-cycloalkyl, $C_3$-$C_6$-alkenyl, $C_3$-$C_6$-alkynyl, 4- to 6-membered heterocycloalkyl, $C_2$-$C_3$-alkylene-$OR^{13a}$ and $C_1$-$C_3$-alkylene-$R^{3a}$; wherein $R^{3a}$ is selected from: cyano, 3- to 6-membered heterocycloalkyl, $C_3$-$C_6$-cycloalkyl and $CO_2R^{13a}$;
$R^4$ and $R^5$ together with the carbon atom to which they are attached form a cyclic group selected from $C_3$-$C_6$-cycloalkyl and a 4- to 6-membered heterocycloalkyl, wherein said heterocycloalkyl group comprises at least one heteroatom selected from N, O and S; and wherein said cycloalkyl group or heterocycloalkyl group is optionally substituted with from 1 to 4 $R^{15}$ groups;
$R^6$, $R^7$ and $R^8$ are each independently selected from H, $C_1$-$C_6$-alkyl and $C_3$-$C_6$-cycloalkyl;
$R^9$ is independently at each occurrence selected from: =O, =S, $=NR^{13}$, $C_1$-$C_6$-alkyl, $C_1$-$C_6$-haloalkyl, halogen, nitro, $OR^{12}$, $SR^{13}$, $S(O)_2R^{13}$, $S(O)_2NR^{13}R^{13}$, $S(O)(NR^{13})R^{13}$, $S(O)R^{13}$, $C(O)R^{13}$, $C(O)NR^{13}R^{13}$, $C(O)OR^{13}$, cyano, $C_2$-$C_6$-alkenyl, $C_2$-$C_6$-alkynyl, and $NR^{13}R^{14}$;

$R^{12}$ is independently at each occurrence selected from: H, $C_1$-$C_6$-alkyl, $C_3$-$C_6$-cycloalkyl, $C_1$-$C_6$-haloalkyl and 4- to 6-membered heterocycloalkyl;
$R^{13}$ is independently at each occurrence selected from: H, benzyl, $C_3$-$C_6$-cycloalkyl and $C_1$-$C_6$-alkyl;
or where two $R^{13}$ groups are attached to the same nitrogen atom, said $R^{13}$ groups, together with said nitrogen atom form a 4-, 5-, 6- or 7-membered heterocycloalkyl ring;
$R^{13a}$ is independently selected from: H, $C_3$-$C_6$-cycloalkyl and $C_1$-$C_6$-alkyl;
$R^{14}$ is independently at each occurrence selected from; H, benzyl, $C_1$-$C_6$-alkyl, $C_3$-$C_6$-cycloalkyl, $C(O)$—$C_1$-$C_6$-alkyl, $S(O)_2$—$C_1$-$C_6$-alkyl and 4- to 6-membered heterocycloalkyl;
or where a $R^{13}$ group and a $R^{14}$ group are attached to the same nitrogen atom, said $R^{13}$ and $R^{14}$ groups, together with said nitrogen atom form a 4-, 5-, 6- or 7-membered heterocycloalkyl ring; $R^{15}$ is independently at each occurrence selected from: =O, =S, $=NR^{13}$, $C_1$-$C_6$-alkyl, $C_1$-$C_6$-haloalkyl, halogen, nitro, $OR^{12}$, $SR^{13}$, $S(O)_2R^{13}$, $S(O)_2NR^{13}R^{13}$, $S(O)(NR^{13})R^{13}$, $S(O)R^{13}$, $C(O)R^{13}$, $C(O)NR^{13}R^{13}$, $C(O)OR^{13}$, cyano, $C_2$-$C_6$-alkenyl, $C_2$-$C_6$-alkynyl, and $NR^{13}R^{14}$;
$R^{19}$ is independently selected from H, $C_1$-$C_6$-alkyl, $C_1$-$C_6$-haloalkyl, $C_3$-$C_6$-cycloalkyl, $C_3$-$C_6$-alkenyl, $C_3$-$C_6$-alkynyl, 4- to 6-membered heterocycloalkyl, $C_2$-$C_3$-alkylene-$OR^{3a}$ and $C_1$-$C_3$-alkylene-$R^{19a}$; wherein $R^{19a}$ is selected from: cyano, 3- to 6-membered heterocycloalkyl, $C_3$-$C_6$-cycloalkyl and $CO_2R^{13a}$;
$R^{21}$ is independently selected from H, halo, $C_1$-$C_4$-alkyl and $C_1$-$C_4$-haloalkyl;
or two $R^{21}$ groups, together with the carbon atoms to which they are attached form a phenyl ring, a $C_3$-$C_6$-cycloalkyl ring, 5- to 7-membered heterocycloalkyl ring or a 5- or 6-membered bridged bicyclic cycloalkyl or cycloalkenyl ring system, said ring or ring system being optionally substituted with from 1 to 6 $R^9$ groups;
or $R^{19}$ and one $R^{21}$ group, together with the nitrogen and carbon atoms to which they are attached form a 5- to 7-membered heterocycloalkyl ring, said ring being optionally substituted with from 1 to 6 $R^9$ groups;
$R^{22}$ is independently at each occurrence selected from H and $C_1$-$C_4$-alkyl; and
p is an integer selected from 0, 1, 2 and 3;
wherein any abovementioned alkyl, alkenyl, alkynyl, alkylene, cycloalkyl, heterocycloalkyl (including where two $R^{13}$ groups or an $R^{13}$ group and an $R^{14}$ group together with a nitrogen to which they are attached form a heterocycloalkyl ring) group is optionally substituted, where chemically possible, by 1 to 4 substituents which are each independently selected at each occurrence from the group consisting of: =O; $=NR^a$, $=NOR^a$, $C_1$-$C_4$-alkyl, halo, nitro, cyano, $C_1$-$C_4$-haloalkyl, $C_2$-$C_4$-alkenyl, $C_2$-$C_4$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$ and $OR^a$;
wherein $R^a$ is independently selected from H and $C_1$-$C_4$-alkyl; and $R^b$ is independently H, $C_1$-$C_4$-alkyl, $C(O)$—$C_1$-$C_4$-alkyl, $S(O)_2$—$C_1$-$C_4$-alkyl; or an agronomically acceptable salt or N-oxide thereof.

In an embodiment, the compound of formula I or formula II is a compound of formula III:

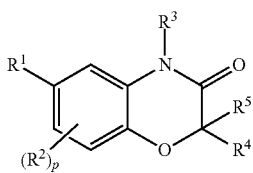

III wherein $R^1$, $R^2$, $R^3$, $R^4$, $R^5$ and p are as described above for compounds of formula I or formula II.

In an embodiment, the compound of formula I or formula II is a compound of formula IV:

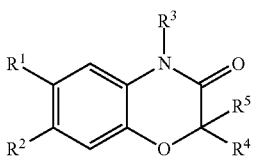

IV wherein $R^1$, $R^2$, $R^3$, $R^4$ and $R^5$ are as described above for compounds of formula I or formula II.

In an embodiment, the compound of formula I or formula II is a compound of formula V:

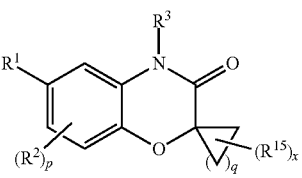

V wherein $R^1$, $R^2$, $R^3$, $R^{15}$ and p are as described above for compounds of formula I or formula II; wherein x is an integer selected from 0, 1, 2, 3 and 4; and q is an integer selected from 1, 2, 3 and 4.

In an embodiment, the compound of formula I or formula II is a compound of formula VI:

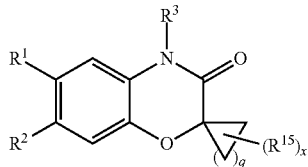

VI wherein $R^1$, $R^2$, $R^3$ and $R^{15}$ are as described above for compounds of formula I or formula II;
wherein x is an integer selected from 0, 1, 2, 3 and 4; and q is an integer selected from 1, 2, 3 and 4.

In an embodiment, the compound of formula I or formula II is a compound of formula VII:

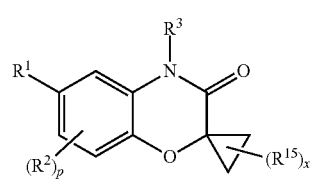

VII wherein $R^1$, $R^2$, $R^3$, $R^{15}$ and p are as described above for compounds of formula I or formula II; and wherein x is an integer selected from 0, 1, 2, 3 and 4.

In an embodiment, the compound of formula I or formula II is a compound of formula VIII:

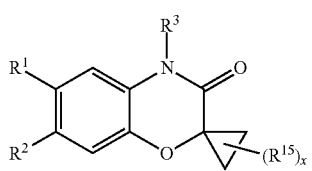

VIII wherein $R^1$, $R^2$, $R^3$ and $R^{15}$ are as described above for compounds of formula I or formula II; and wherein x is an integer selected from 0, 1, 2, 3 and 4.

In an embodiment, the compound of formula I or formula II is a compound of formula IX:

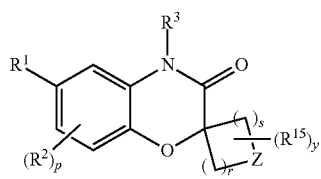

IX wherein $R^1$, $R^2$, $R^3$, $R^{15}$ and p are as described above for compounds of formula I or formula II; and wherein Z is independently selected from —$NR^{16}$—, —O—, —S(O)—, —S(O)$_2$—, —S(O)$NR^{17}$— and —S—; $R^{16}$ is independently selected from H, $C_1$-$C_4$-alkyl, S(O)$_2R^{13}$, C(O)$R^{13}$, $C_3$-$C_4$-alkenyl and $C_3$-$C_4$-alkynyl; $R^{17}$ is independently selected from H, $C_1$-$C_4$-alkyl, $C_3$-$C_4$-alkenyl and $C_3$-$C_4$-alkynyl; y is an integer selected from 0, 1, 2 and 3; r and s are each an integer selected from 1, 2 and 3; and wherein the sum of r and s is 2, 3 or 4.

In an embodiment, the compound of formula I or formula II is a compound of formula X:

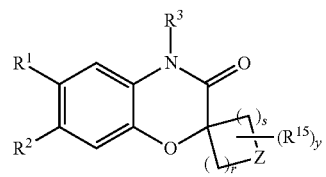

X wherein $R^1$, $R^2$, $R^3$ and $R^{15}$ are as described above for compounds of formula I or formula II; and wherein Z is independently selected from —$NR^6$—, —O—, —S(O)—, —S(O)$_2$—, —S(O)NR$^{17}$— and —S—; R$^{16}$ is independently selected from H, C$_1$-C$_4$-alkyl, S(O)$_2$R$^{13}$C(O)R$^{13}$, C$_3$-C$_4$-alkenyl and C$_3$-C$_4$-alkynyl; R$^{17}$ is independently selected from H, C$_1$-C$_4$-alkyl, C$_3$-C$_4$-alkenyl and C$_3$-C$_4$-alkynyl; y is an integer selected from 0, 1, 2 and 3; r and s are each an integer selected from 1, 2 and 3; and wherein the sum of r and s is 2, 3 or 4.

In an embodiment, the compound of formula I or formula II is a compound of formula XI:

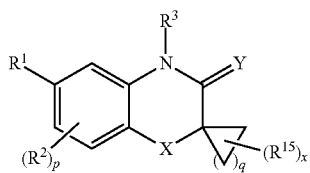

XI wherein R$^1$, R$^2$, R$^3$, R$^{15}$, X, Y and p are as described above for compounds of formula I or formula II; wherein x is an integer selected from 0, 1, 2, 3 and 4; and q is an integer selected from 1, 2, 3 and 4.

In an embodiment, the compound of formula I or formula II is a compound of formula XII:

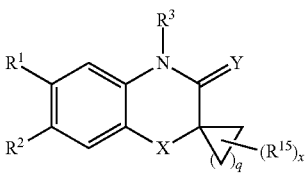

XII wherein R$^1$, R$^2$, R$^3$, R$^{15}$, X and Y are as described above for compounds of formula I or formula II; wherein x is an integer selected from 0, 1, 2, 3 and 4; and q is an integer selected from 1, 2, 3 and 4.

In an embodiment, the compound of formula I or formula II is a compound of formula XIII:

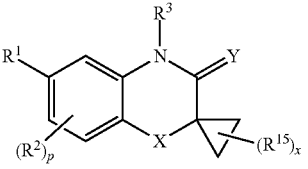

XIII wherein R$^1$, R$^2$, R$^3$, R$^{15}$, X, Y and p are as described above for compounds of formula I or formula II; and wherein x is an integer selected from 0, 1, 2, 3 and 4.

In an embodiment, the compound of formula I or formula II is a compound of formula XIV:

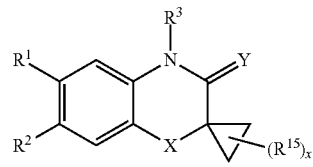

XIV wherein R$^1$, R$^2$, R$^3$, R$^{15}$, X and Y are as described above for compounds of formula I or formula II; and wherein x is an integer selected from 0, 1, 2, 3 and 4.

In an embodiment, the compound of formula I or formula II is a compound of formula XV:

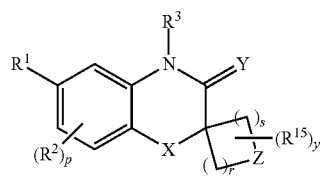

XV wherein R$^1$, R$^2$, R$^3$, R$^{15}$, X, Y and p are as described above for compounds of formula I or formula II; and wherein Z is independently selected from —NR$^6$—, —O—, —S(O)—, —S(O)$_2$—, —S(O)NR$^{17}$— and —S—; R$^{16}$ is independently selected from H, C$_1$-C$_4$-alkyl, S(O)$_2$R$^{13}$, C(O)R$^{13}$, C$_3$-C$_4$-alkenyl and C$_3$-C$_4$-alkynyl; R$^{17}$ is independently selected from H, C$_1$-C$_4$-alkyl, C$_3$-C$_4$-alkenyl and C$_3$-C$_4$-alkynyl; y is an integer selected from 0, 1, 2 and 3; r and s are each an integer selected from 1, 2 and 3; and wherein the sum of r and s is 2, 3 or 4.

In an embodiment, the compound of formula I or formula II is a compound of formula XVI:

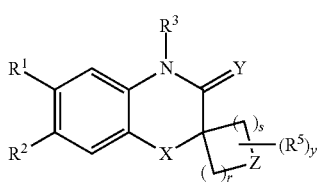

XVI wherein R$^1$, R$^2$, R$^3$, R$^{15}$, X and Y are as described above for compounds of formula I or formula II; and wherein Z is independently selected from —NR$^6$—, —O—, —S(O)—, —S(O)$_2$—, —S(O)NR$^{17}$— and —S—; R$^{16}$ is independently selected from H, C$_1$-C$_4$-alkyl, S(O)$_2$R$^{13}$, C(O)R$^{13}$, C$_3$-C$_4$-alkenyl and C$_3$-C$_4$-alkynyl; R$^{17}$ is independently selected from H, C$_1$-C$_4$-alkyl, C$_3$-C$_4$-alkenyl and C$_3$-C$_4$-alkynyl; y is an integer selected from 0, 1, 2 and 3; r and s are each an integer selected from 1, 2 and 3; and wherein the sum of r and s is 2, 3 or 4.

The following embodiments apply to compounds of any of formulae (I)-(XVI). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

It may be that $R^1$ is independently a 5- to 7-membered heterocyclyl group; wherein said heterocyclyl group is comprises at least one nitrogen atom in the ring; wherein said heterocyclyl group is optionally unsaturated and is optionally fused to a second ring selected from benzene, 5- or 6-membered heteroaryl, $C_5$-$C_6$-cycloalkyl and 5- to 7-membered heterocycloalkyl; wherein $R^1$ is optionally substituted with from 1 to 6 $R^9$ groups. It may be that the 5- to 7-membered heterocyclyl group is attached to the rest of the molecule via a nitrogen atom in the ring (where there is more than one nitrogen atom in the ring) or the nitrogen atom in the ring (where there is a single nitrogen atom in the ring).

$R^1$ may have the structure:

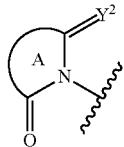

wherein ring A is a 5- or 6-membered heterocyclyl group, wherein said heterocyclyl group is optionally unsaturated and is optionally fused to a 5- or 6-membered cycloalkyl, benzene or 5- or 6-heterocycloalkyl ring; $=Y^2$ is $=O$ or $=S$ and wherein the group $R^1$ is optionally substituted with from 1 to 4 $R^9$ groups. Ring A may be a 5- or 6-membered heterocyclyl group, wherein said heterocyclyl group is optionally unsaturated; and wherein the group $R^1$ is optionally substituted with from 1 to 4 $R^9$ groups. $=Y^2$ may be $=O$.

$R^1$ may have the structure:

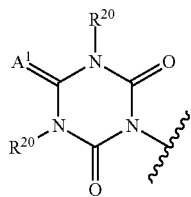

wherein $=A^1$ is independently selected from $=O$, $=S$; and $R^{20}$ is independently at each occurrence selected from H and $C_1$-$C_4$-alkyl.

$=A^1$ may be $=O$. $=A^1$ may be $=S$. $R^{20}$ may be at both occurrences $C_1$-$C_4$-alkyl, e.g. Me.

In certain illustrative examples, $R^1$ may be:

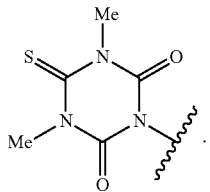

Preferably, however, $R^1$ does not have the structure:

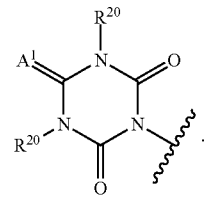

$R^1$ may have the structure:

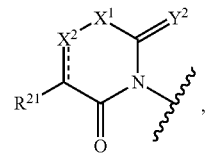

wherein ≡≡≡≡ is either a double bond or a single bond; $=Y^2$ is $=O$ or $=S$; $X^1$ is independently absent or is selected from $NR^{19}$ and $CR^{22}R^{22}$; $X^2$ is independently absent or is $CR^{21}$; $R^{19}$ is independently selected from H, $C_1$-$C_6$-alkyl, $C_1$-$C_6$-haloalkyl, $C_3$-$C_6$-cycloalkyl, $C_3$-$C_6$-alkenyl, $C_3$-$C_6$-alkynyl, 4- to 6-membered heterocycloalkyl, $C_2$-$C_3$-alkylene-$OR^{13a}$ and $C_1$-$C_3$-alkylene-$R^{19a}$; wherein $R^{19a}$ is selected from: cyano, 3- to 6-membered heterocycloalkyl, $C_3$-$C_6$-cycloalkyl and $CO_2R^{13a}$; $R^{21}$ is independently selected from H, halo, $C_1$-$C_4$-alkyl and $C_1$-$C_4$-haloalkyl; or two $R^{21}$ groups, together with the carbon atoms to which they are attached form a phenyl ring, a $C_3$-$C_6$-cycloalkyl ring, 5- to 7-membered heterocycloalkyl ring or a 5- or 6-membered bridged bicyclic cycloalkyl ring system, said ring or ring system being optionally substituted with from 1 to 6 $R^9$ groups; or $R^{19}$ and one $R^{21}$ group, together with the nitrogen and carbon atoms to which they are attached form a 5- to 7-membered heterocycloalkyl ring, said ring being optionally substituted with from 1 to 6 $R^9$ groups; and $R^{22}$ is independently at each occurrence selected from H and $C_1$-$C_4$-alkyl.

$R^1$ may have the structure:

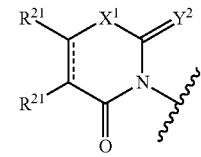

wherein ≡≡≡≡ is either a carbon-carbon double bond or a carbon-carbon single bond; $=Y^2$ is $=O$ or $=S$; $X^1$ is independently absent or is selected from $NR^{19}$ and $CR^{22}R^{22}$; $R^{19}$ is independently selected from H, $C_1$-$C_6$-alkyl, $C_1$-$C_6$-haloalkyl, $C_3$-$C_6$-cycloalkyl, $C_3$-$C_6$-alkenyl, $C_3$-$C_6$-alkynyl, 4- to 6-membered heterocycloalkyl, $C_2$-$C_3$-alkylene-$OR^{3a}$ and $C_1$-$C_3$-alkylene-$R^{19a}$; wherein $R^{19a}$ is selected from: cyano, 3- to 6-membered heterocycloalkyl, $C_3$-$C_6$-cycloalkyl and $CO_2R^{13a}$; $R^{21}$ is independently selected from H, halo, $C_1$-$C_4$-alkyl and $C_1$-$C_4$-haloalkyl; or two $R^{21}$ groups, together with the carbon atoms to which they are attached form a phenyl ring, a $C_3$-$C_6$-cycloalkyl ring, 5- to 7-membered heterocycloalkyl ring or a 5- or 6-membered bridged bicyclic cycloalkyl ring system, said ring or ring system being optionally substituted with from 1 to 6 $R^9$ groups; or $R^{19}$ and one $R^{21}$ group, together with the nitrogen and carbon atoms to which they are attached form a 5- to 7-membered heterocycloalkyl ring, said ring being optionally substituted with from 1 to 6 $R^9$ groups; and $R^{22}$ is independently at each occurrence selected from H and $C_1$-$C_4$-alkyl.

$R^1$ may have the structure:

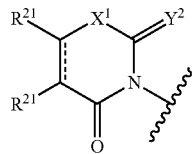

wherein ====== is either a carbon-carbon double bond or a carbon-carbon single bond; $=Y^2$ is $=O$ or $=S$; $X^1$ is independently absent or is selected from $NR^{19}$ and $CR^{22}R^{22}$; $R^{19}$ is independently selected from H and $C_1$-$C_4$-alkyl; $R^{21}$ is independently selected from H, halo, $C_1$-$C_4$-alkyl and $C_1$-$C_4$-haloalkyl or the two $R^{21}$ groups, together with the carbons to which they are attached form a phenyl ring or a $C_3$-$C_6$-cycloalkyl ring, said phenyl or cyclohexyl ring being optionally substituted with from 1 to 6 $R^9$ groups; and $R^{22}$ is independently at each occurrence selected from H and $C_1$-$C_4$-alkyl. $=Y^2$ may be $=O$. $X^1$ may be absent.

$R^1$ may be

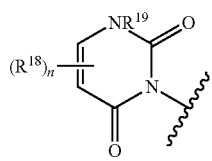

wherein $R^{18}$ is independently at each occurrence selected from $C_1$-$C_4$-alkyl, $C_1$-$C_4$-haloalkyl, halogen, nitro, $OR^{12}$, $SR^{13}$, cyano, $C_2$-$C_4$-alkenyl, $C_2$-$C_4$-alkynyl, $C_3$-$C_6$-cycloalkyl and $NR^{13}R^{14}$; $R^{19}$ is independently selected from H, $C_1$-$C_6$-alkyl, $C_1$-$C_6$-haloalkyl, $C_3$-$C_6$-cycloalkyl, $C_3$-$C_6$-alkenyl, $C_3$-$C_6$-alkynyl, 4- to 6-membered heterocycloalkyl, $C_2$-$C_3$-alkylene-$OR^{13a}$ and $C_1$-$C_3$-alkylene-$R^{19a}$; wherein $R^{19a}$ is selected from: cyano, 3- to 6-membered heterocycloalkyl, $C_3$-$C_6$-cycloalkyl and $CO_2R^{13a}$; and n is an integer independently selected from 0, 1 and 2; wherein where n is 2, the two $R^{18}$ groups may together with the carbon atoms to which they are attached form a benzene ring.

It may be that $R^{18}$ is independently at each occurrence selected from $C_1$-$C_4$-alkyl, $C_1$-$C_4$-haloalkyl, halogen, nitro, $OR^{12}$, $SR^{13}$, cyano, $C_2$-$C_4$-alkenyl, $C_2$-$C_4$-alkynyl, and $NR^{13}R^{14}$; $R^{19}$ is independently selected from H, $C_1$-$C_6$-alkyl, $C_1$-$C_6$-haloalkyl, $C_3$-$C_6$-alkenyl, $C_3$-$C_6$-alkynyl, 4- to 6-membered heterocycloalkyl, $C_2$-$C_3$-alkylene-$OR^{13a}$ and $C_1$-$C_3$-alkylene-$R^{19a}$; wherein $R^{19a}$ is selected from: cyano and $CO_2R^{13a}$; and n is an integer independently selected from 0, 1 and 2; wherein where n is 2, the two $R^{18}$ groups may together with the carbon atoms to which they are attached form a benzene ring.

It may be that n is 1. $R^{18}$ may be independently at each occurrence selected from: $C_1$-$C_4$-alkyl, $C_1$-$C_4$-haloalkyl and halogen. $R^{18}$ may be independently at each occurrence selected from: $C_1$-$C_4$-alkyl and $C_1$-$C_4$-haloalkyl. Thus, $R^{18}$ may be $C_1$-$C_4$-haloalkyl, e.g. $CF_3$.

It may be that n is 2 and the two $R^{18}$ groups may together with the carbon atoms to which they are attached form a benzene ring.

$R^{19}$ may be independently selected from $C_1$-$C_4$-alkyl, $C_3$-$C_4$-alkenyl, $C_3$-$C_4$-alkynyl and $C_1$-$C_3$-alkylene-$R^{19a}$. $R^{19a}$ may be $CO_2R^{13a}$. $R^{19}$ may independently selected from H and $C_1$-$C_4$-alkyl. $R^{19}$ may be $C_1$-$C_4$-alkyl. Preferably, $R^{19}$ is methyl.

In certain illustrative examples, $R^1$ may be selected from:

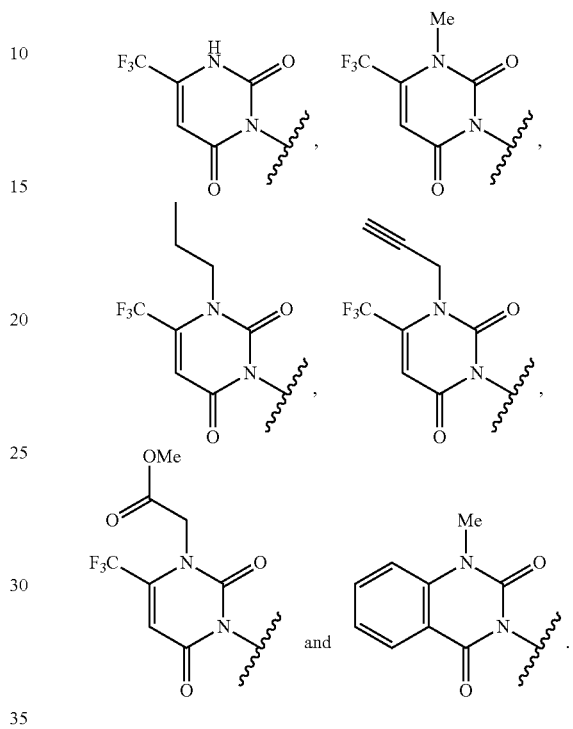

$R^1$ may have the structure:

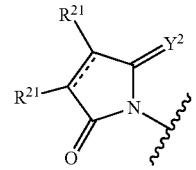

wherein ====== is either a carbon-carbon double bond or a carbon-carbon single bond; $=Y^2$ is $=O$ or $=S$; and $R^{21}$ is independently selected from H, halo, $C_1$-$C_4$-alkyl and $C_1$-$C_4$-haloalkyl or the two $R^{21}$ groups, together with the carbons to which they are attached form a ring selected from phenyl ring, $C_3$-$C_6$-cycloalkyl, 5- or 6-membered heterocycloalkyl, said ring being optionally substituted with from 1 to 6 $R^9$ groups. $=Y^2$ may be $=O$.

$R^1$ may have the structure:

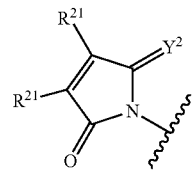

wherein $=Y^2$ is $=O$ or $=S$; and $R^{21}$ is independently selected from H, halo, $C_1$-$C_4$-alkyl and $C_1$-$C_4$-haloalkyl or the two $R^{21}$ groups, together with the carbons to which they are attached form a phenyl ring, said phenyl being optionally substituted with from 1 to 6 $R^9$ groups. $=Y^2$ may be $=O$.

$R^1$ may have the structure:

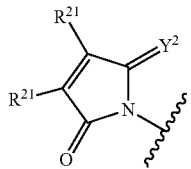

wherein $=Y^2$ is $=O$ or $=S$; and $R^{21}$ is independently selected from H, halo, $C_1$-$C_4$-alkyl and $C_1$-$C_4$-haloalkyl. $=Y^2$ may be $=O$.

$R^1$ may have the structure:

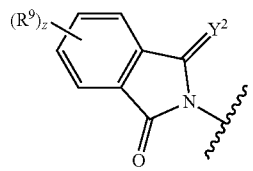

wherein $=Y^2$ is $=O$ or $=S$; and wherein z is an integer selected from 0 to 4. $=Y^2$ may be $=O$. In these embodiments, $R^9$ may be independently at each occurrence selected from halo, $OR^{12}$, $C_1$-$C_4$-alkyl and $C_1$-$C_4$-haloalkyl. In these embodiments, z may be selected from 1 and 2. z may be 1.

In certain illustrative examples, $R^1$ may be:

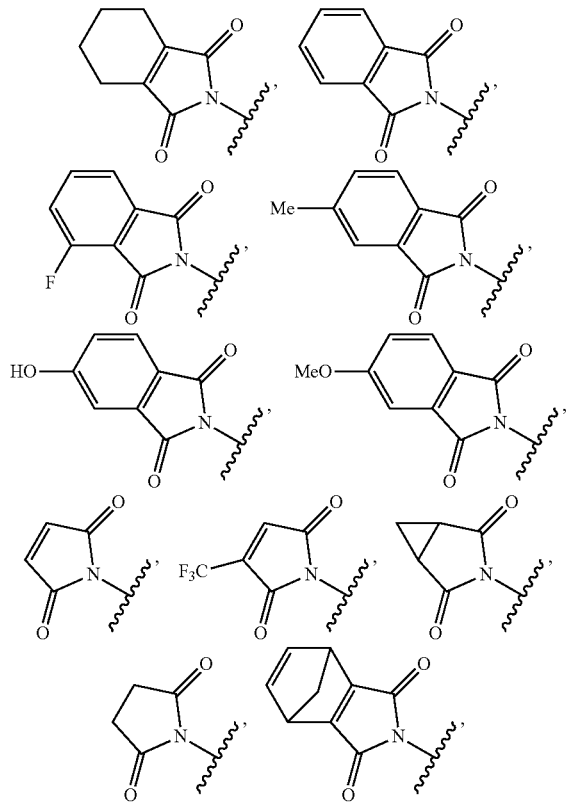

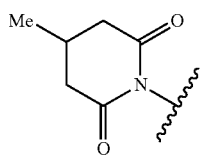 and 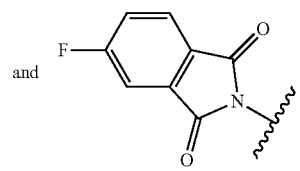

$R^1$ may have the structure:

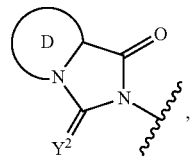

wherein $=Y^2$ is $=O$ or $=S$; and ring D is a 5- to 7-membered heterocycloalkyl ring, said ring being optionally substituted with from 1 to 6 $R^9$ groups. $=Y^2$ may be $=O$.

Ring D may be a heterocycle selected from piperidine, pyrrolidine, morpholine and thiomorpholine.

Ring D may be unsubstituted.

In certain illustrative examples, $R^1$ may be:

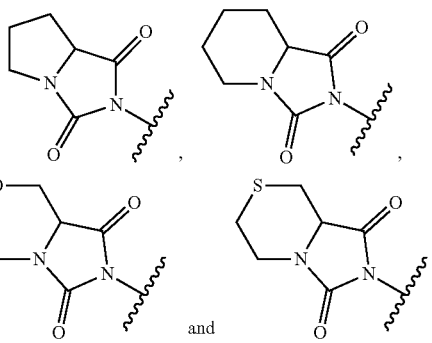

Other illustrative examples of $R^1$ include:

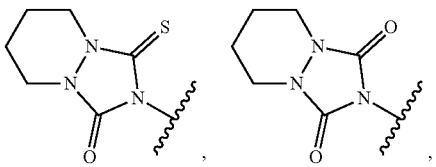

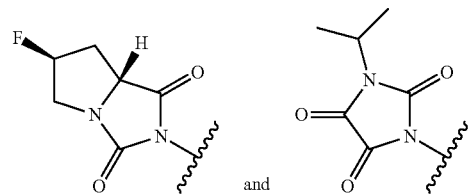

$R^1$ may have the structure:

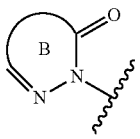

wherein ring B is a 5- or 6-membered heterocyclyl group; and wherein said heterocyclyl group is optionally fused to a 5- or 6-membered cycloalkyl or heterocycloalkyl ring and wherein the group $R^1$ is optionally substituted with from 1 to 5 $R^9$ groups. Ring B may be a 5- or 6-membered heterocyclyl group; and wherein said heterocyclyl group is optionally substituted with from 1 to 5 $R^9$ groups.

Illustrative examples of $R^1$ include:

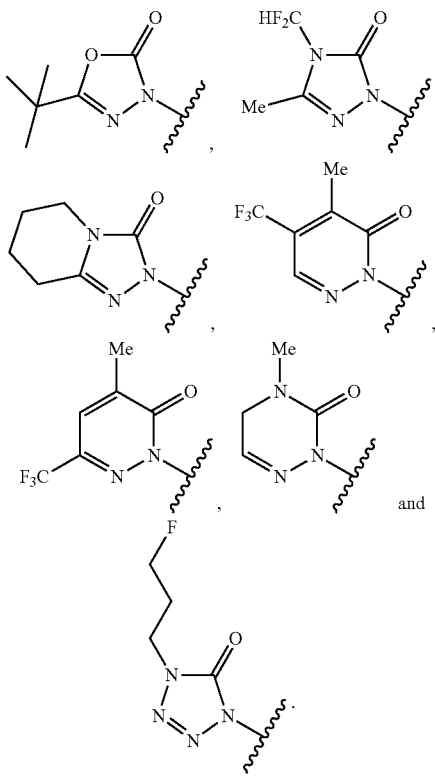

$R^1$ may be —N=CR$^{10}$R$^{11}$ wherein $R^{10}$ and $R^{11}$ together with the carbon atom to which they are attached form a 5- to 9-membered bicyclic or monocyclic heterocyclyl group, wherein said heterocyclyl group is optionally unsaturated; and wherein said heterocyclyl group comprises at least one nitrogen atom in the ring and is optionally substituted with from 1 to 6 $R^9$ groups.

$R^1$ may have the structure:

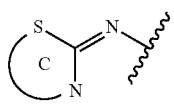

wherein ring C is a 5- or 6-membered heterocyclyl group, wherein said heterocyclyl group is optionally unsaturated; and wherein said heterocyclyl group is optionally fused to a 5- or 6-membered cycloalkyl or heterocycloalkyl ring and wherein the group $R^1$ is optionally substituted with from 1 to 5 $R^9$ groups. It may be that ring C is a 5- or 6-membered heterocyclyl group, wherein said heterocyclyl group is optionally unsaturated; and wherein said heterocyclyl group is fused to a 5- or 6-membered cycloalkyl or heterocycloalkyl ring and wherein the group $R^1$ is optionally substituted with from 1 to 5 $R^9$ groups.

Illustrative examples of $R^1$ include:

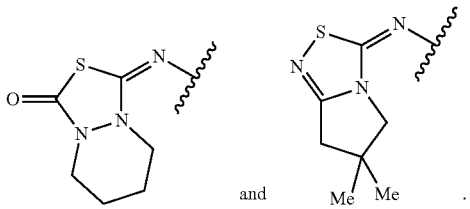 [SMILES: */N=c1/sc(=O)n2n1CCCC2 ; */N=c1/snc2n1CC(C)(C)C2]

$R^3$ may be selected from $C_1$-$C_6$-alkyl, $C_1$-$C_6$-haloalkyl, $C_3$-$C_6$-cycloalkyl, $C_1$-$C_3$-alkylene-$C_3$-$C_6$-cycloalkyl, $C_1$-$C_3$-alkylene-CO$_2$R$^{13a}$, $C_2$-$C_3$-alkylene-OR$^{13a}$, $C_3$-$C_6$-alkenyl, $C_3$-$C_6$-alkynyl and 4- to 6-membered heterocycloalkyl.

$R^3$ may be selected from $C_1$-$C_6$-alkyl, $C_3$-$C_6$-cycloalkyl, $C_1$-$C_3$-alkylene-$C_3$-$C_6$-cycloalkyl, $C_3$-$C_6$-alkenyl, $C_3$-$C_6$-alkynyl and 4- to 6-membered heterocycloalkyl. $R^3$ may be unsubstituted. $R^3$ may be selected from $C_1$-$C_4$-alkyl, $C_1$-alkylene-$C_3$-cycloalkyl, $C_3$-$C_5$-alkenyl and $C_3$-$C_4$-alkynyl. $R^3$ may be selected from $C_3$-$C_5$-alkenyl and $C_3$-$C_4$-alkynyl. $R^3$ may be selected from allyl, prenyl and propargyl. $R^3$ may be $C_3$-$C_4$-alkynyl. $R^3$ may be propargyl, which may be terminally substituted (e.g. with a halo group) or unsubstituted. $R^3$ may be unsubstituted propargyl. $R^3$ may be selected from $C_1$-$C_6$-alkyl, $C_3$-$C_6$-cycloalkyl, $C_1$-$C_3$-alkylene-CO$_2$R$^{13a}$, $C_2$-$C_3$-alkylene-OR$^{13a}$, $C_1$-$C_3$-alkylene-$C_3$-$C_6$-cycloalkyl, $C_3$-$C_6$-alkenyl, $C_3$-$C_6$-alkynyl and 4- to 6-membered heterocycloalkyl. $R^3$ may be unsubstituted. $R^3$ may be selected from $C_1$-$C_4$-alkyl, $C_1$-alkylene-$C_3$-$C_4$-cycloalkyl, $C_3$-$C_5$-alkenyl and $C_3$-$C_4$-alkynyl.

$R^3$ may be $C_1$-$C_3$-alkylene-CO$_2$R$^{13a}$. $R^3$ may be $C_1$-alkylene-CO$_2$R$^{13a}$. $R^3$ may be CH(Me)-CO$_2$—R$^{13a}$.

$R^3$ may be $C_2$-$C_3$-alkylene-OR$^{13a}$. $R^3$ may be $C_2$-alkylene-OR$^{13a}$. R$^{13a}$ may be $C_1$-$C_4$-alkyl. R$^{13a}$ may be methyl or ethyl.

$R^3$ may be $C_1$-alkylene-$C_3$-$C_4$-cycloalkyl. $R^3$ may be $C_1$-alkylene-cyclopropyl. $R^3$ may be $C_1$-alkylene-cyclobutyl. In these embodiments, $R^3$ may be unsubstituted.

$R^3$ may be $C_1$-$C_3$-alkylene-CN. $R^3$ may be $C_1$-alkylene-CN. $R^3$ may be CH$_2$CN.

$R^4$ and $R^5$ may, together with the carbon atom to which they are attached, form a $C_3$-$C_6$-cycloalkyl group; wherein the cycloalkyl group is optionally substituted with from 1 to 4 $R^{15}$ groups. Thus, $R^4$ and $R^5$ may together with the carbon atom to which they are attached form a cyclopropyl group; wherein the cyclopropyl group is optionally substituted with from 1 to 4 $R^{15}$ groups. $R^4$ and $R^5$ may together with the carbon atom to which they are attached form an unsubstituted cyclopropyl group.

$R^4$ and $R^5$ may together with the carbon atom to which they are attached form a cyclobutyl group; wherein the cyclobutyl group is optionally substituted with from 1 to 4 $R^{15}$ groups. $R^4$ and $R^5$ may together with the carbon atom to which they are attached form an unsubstituted cyclobutyl group.

$R^4$ and $R^5$ may together with the carbon atom to which they are attached form a cyclopentyl group; wherein the cyclopentyl group is optionally substituted with from 1 to 4 $R^{15}$ groups. $R^4$ and $R^5$ may together with the carbon atom to which they are attached form an unsubstituted cyclopentyl group.

$R^4$ and $R^5$ may together with the carbon atom to which they are attached form a cyclohexyl group; wherein the cyclohexyl group is optionally substituted with from 1 to 4 $R^{15}$ groups. $R^4$ and $R^5$ may together with the carbon atom to which they are attached form an unsubstituted cyclohexyl group.

$R^4$ and $R^5$ together with the carbon atom to which they are attached may form a 4- to 6-membered heterocycloalkyl group; wherein the heterocycloalkyl group is optionally substituted with from 1 to 4 $R^{15}$ groups.

$R^4$ and $R^5$ may, together with the carbon to which they are attached have the structure:

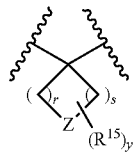

wherein Z is independently selected from —$NR^{16}$—, —O—, —S(O)—, —S(O)$_2$—, —S(O)$NR^{17}$— and —S—; $R^{16}$ is independently selected from H, $C_1$-$C_4$-alkyl, $S(O)_2R^{13}$, $C(O)R^{13}$, $C_3$-$C_4$-alkenyl and $C_3$-$C_4$-alkynyl; $R^{17}$ is independently selected from H, $C_1$-$C_4$-alkyl, $C_3$-$C_4$-alkenyl and $C_3$-$C_4$-alkynyl; y is an integer selected from 0, 1, 2 and 3; r and s are each an integer selected from 1, 2 and 3; and wherein the sum of r and s is 2, 3 or 4.

$R^4$ and $R^5$ together with the carbon atom to which they are attached may form a 4-membered heterocycloalkyl group; wherein the heterocycloalkyl group is optionally substituted with from 1 to 4 $R^{15}$ groups. Thus, it may be that r is 1 and s is 1.

$R^4$ and $R^5$ together with the carbon atom to which they are attached may form a 5-membered heterocycloalkyl group; wherein the heterocycloalkyl group is optionally substituted with from 1 to 4 $R^{15}$ groups. Thus, it may be that r is 1 and s is 2.

$R^4$ and $R^5$ together with the carbon atom to which they are attached may form a 6-membered heterocycloalkyl group; wherein the heterocycloalkyl group is optionally substituted with from 1 to 4 $R^{15}$ groups. It may be that r is 2 and s is 2. It may be that r is 1 and s is 3.

It may be that Z is $NR^{16}$. It may be that Z is $NR^{16}$, r is 1 and s is 1. It may be that Z is $NR^{16}$, r is 1 and s is 2. It may be that Z is $NR^{16}$, r is 2 and s is 2. It may be that Z is $NR^{16}$, r is 1 and s is 3. It may be that $R^{16}$ is selected from H and $C_1$-$C_4$-alkyl. It may be that $R^{16}$ is H. It may be that $R^{16}$ is $C_1$-$C_4$-alkyl, e.g. Me.

It may be that Z is O or S. It may be that Z is O. It may be that Z is S. It may be that Z is O, r is 1 and s is 1. It may be that Z is O, r is 1 and s is 2. It may be that Z is O, r is 2 and s is 2. It may be that Z is O, r is 1 and s is 3. It may be that Z is S, r is 1 and s is 1. It may be that Z is S, r is 1 and s is 2. It may be that Z is S, r is 2 and s is 2. It may be that Z is S, r is 1 and s is 3.

It may be that Z is $SO_2$. It may be that Z is $SO_2$, r is 1 and s is 1. It may be that Z is $SO_2$, r is 1 and s is 2. It may be that Z is $SO_2$, r is 2 and s is 2. It may be that Z is $SO_2$, r is 1 and s is 3. y may be 0. y may be 1.

$R^9$ may be independently at each occurrence selected from: =O, =S, $C_1$-$C_4$-alkyl, $C_1$-$C_4$-haloalkyl and halogen. $R^9$ may be independently at each occurrence selected from: =O, =S, $C_1$-$C_4$-alkyl and $C_1$-$C_4$-haloalkyl. $R^9$ may be independently at each occurrence selected from: $C_1$-$C_4$-alkyl, $C_1$-$C_4$-haloalkyl and halogen.

p may be 1 or p may be 2. $R^2$ may be independently at each occurrence selected from: $C_1$-$C_4$-alkyl, $C_1$-$C_4$-haloalkyl and halogen. It may be that $R^2$ is at each occurrence halogen. It may be that $R^2$ is at each occurrence F. Said halogen substituents may be the same or different. If, for example, p is 2, $R^2$ may be at both occurrences F. As another example, if p is 2, $R^2$ may be at one occurrence Cl and at the other occurrence F. Preferably, p is 1 and the single $R^2$ substituent is situated para to the nitrogen that is also attached to $R^3$. In these embodiments, the single $R^2$ may be halogen, e.g. fluoro. Further preferably, p is 1 and the single $R^2$ substituent is fluoro and is situated para to the nitrogen that is also attached to $R^3$.

It may be that $R^{12}$ is independently at each occurrence selected from: H, $C_1$-$C_6$-alkyl, $C_3$-$C_6$-cycloalkyl and $C_1$-$C_6$-haloalkyl; $R^{13}$ is independently at each occurrence selected from: H, $C_3$-$C_6$-cycloalkyl and $C_1$-$C_6$-alkyl; and $R^{14}$ is independently at each occurrence selected from; H, $C_1$-$C_6$-alkyl, $C_3$-$C_6$-cycloalkyl, C(O)—$C_1$-$C_6$-alkyl and $S(O)_2$—$C_1$-$C_6$-alkyl.

It may be that $R^{12}$ is independently at each occurrence selected from: H, $C_1$-$C_4$-alkyl and $C_1$-$C_4$-haloalkyl; $R^{13}$ is independently at each occurrence selected from: H and $C_1$-$C_4$-alkyl; and $R^{14}$ is independently at each occurrence selected from; H, $C_1$-$C_4$-alkyl, C(O)—$C_1$-$C_4$-alkyl and $S(O)_2$—$C_1$-$C_4$-alkyl.

$R^{15}$ may be independently at each occurrence be selected from =O, $OR^{12}$, $NR^{13}R^{14}$, $C_1$-$C_4$-alkyl and $C_1$-$C_4$-haloalkyl. $R^{15}$ may be independently at each occurrence be selected from $C_1$-$C_4$-alkyl and $C_1$-$C_4$-haloalkyl.

It may be that X is independently selected from O, S, S(O) and $S(O)_2$. Preferably, X is O.

It may be that Y is O.

It may be that X is independently selected from O, S, S(O) and $S(O)_2$ and Y is O. Preferably, X is O and Y is O.

It may be that X is independently selected from O, S, S(O) and $S(O)_2$; Y is O; $R^2$ is fluoro; p is 1 and $R^2$ is situated para to the nitrogen that is also attached to $R^3$. Preferably, X is O; Y is O and $R^2$ is fluoro; p is 1 and $R^2$ is situated para to the nitrogen that is also attached to $R^3$.

It may be that X is independently selected from O, S, S(O) and $S(O)_2$; Y is O and $R^3$ is propargyl. Preferably, X is O; Y is O and $R^3$ is propargyl.

It may be that X is independently selected from O, S, S(O) and $S(O)_2$; Y is O; $R^2$ is F; p is 1 and $R^4$ and $R^5$ together with the carbon atom to which they are attached form a cyclic group selected from $C_3$-$C_6$-cycloalkyl. Preferably X is O; Y is O; $R^2$ is F; p is 1 and $R^4$ and $R^5$ together with the carbon atom to which they are attached form cyclopropyl.

It may be that X is independently selected from O, S, S(O) and $S(O)_2$; Y is O; $R^2$ is F; p is 1; $R^3$ is propargyl and $R^4$ and $R^5$ together with the carbon atom to which they are attached form a cyclic group selected from $C_3$-$C_6$-cycloalkyl. Preferably X is O; Y is O; $R^2$ is F; p is 1; $R^3$ is propargyl and $R^4$ and $R^5$ together with the carbon atom to which they are attached form cyclopropyl.

The compound of formula I or formula II may be selected from:

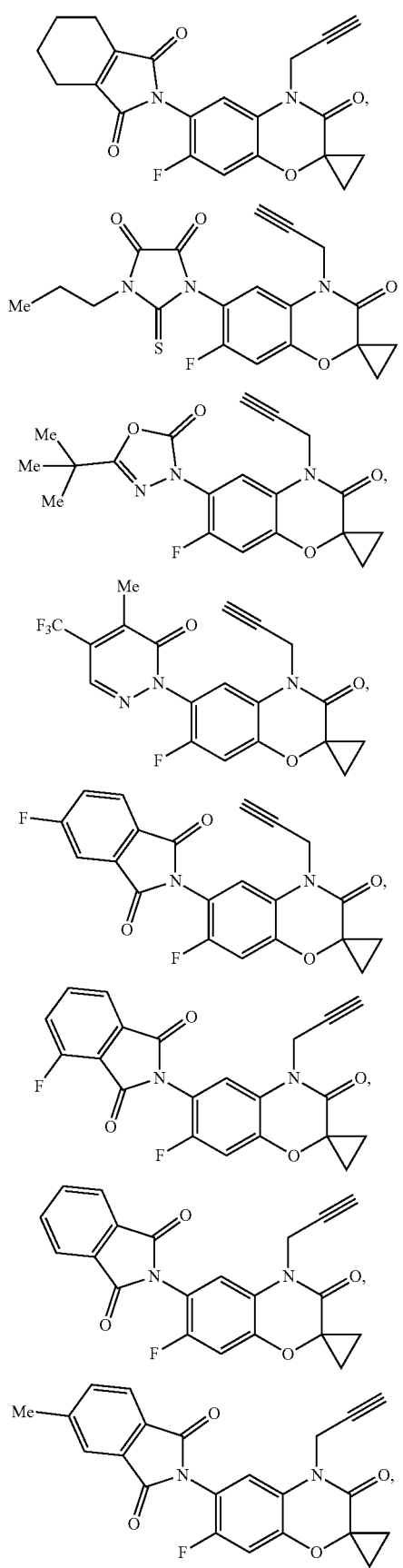
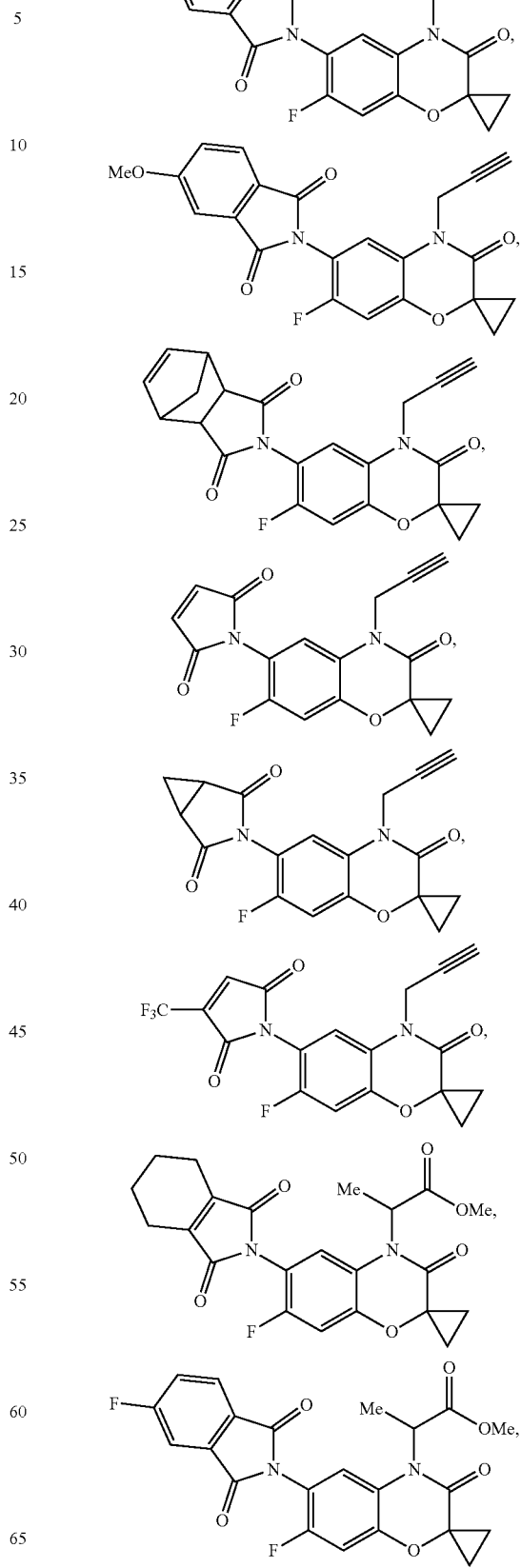

-continued
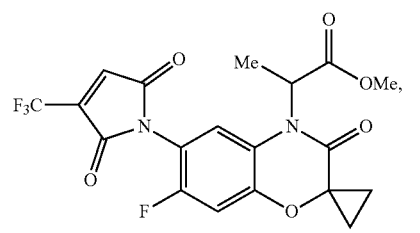
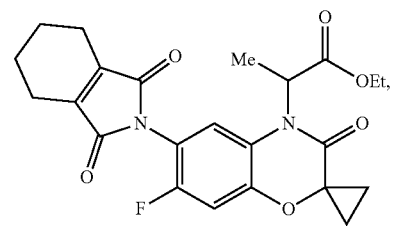
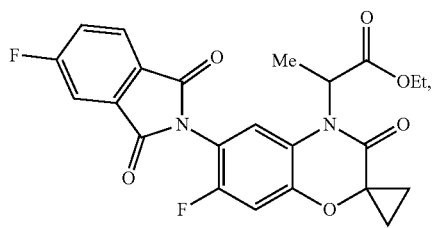
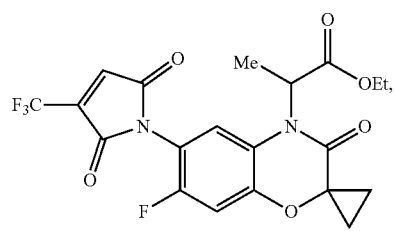
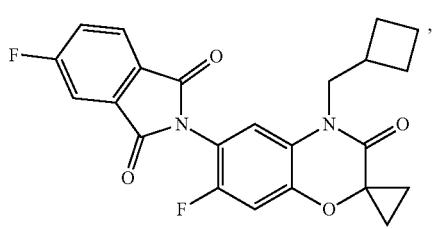
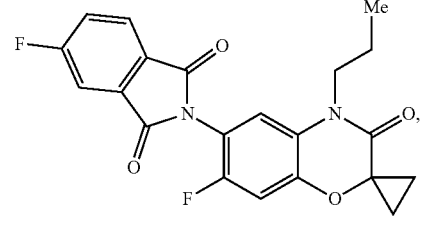
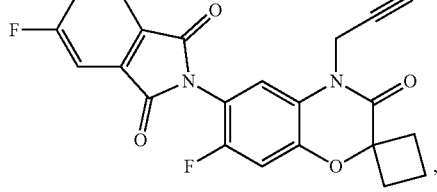
-continued
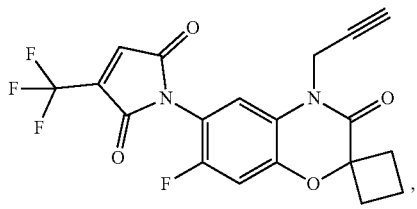
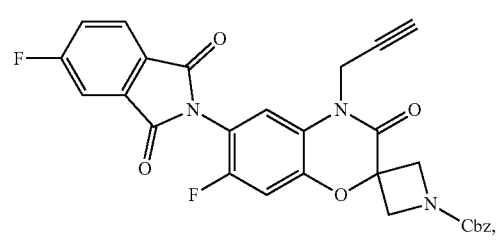
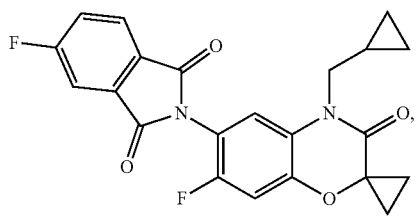
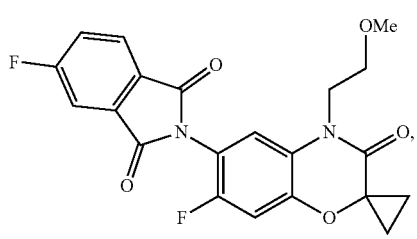
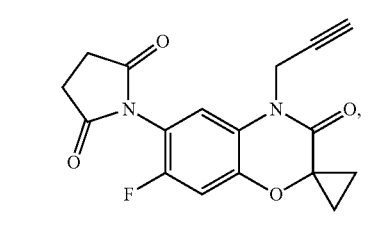
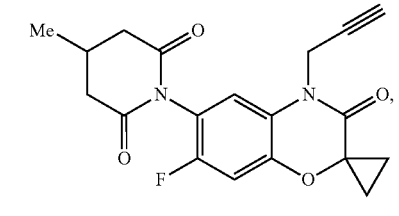
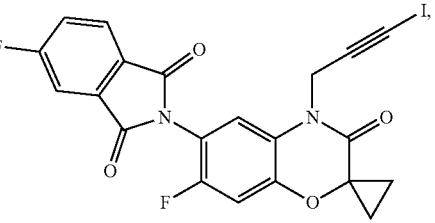

-continued

-continued

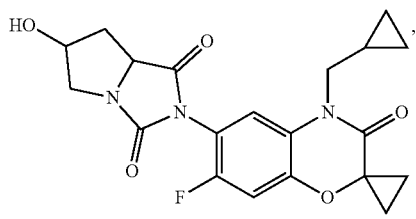

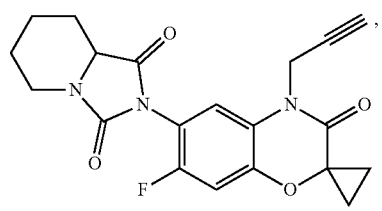

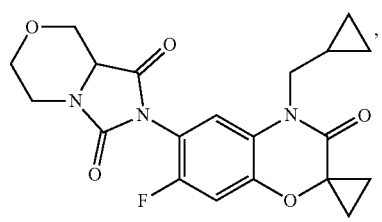

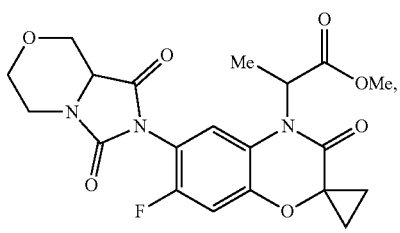

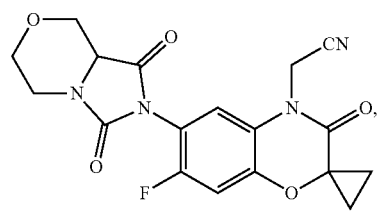

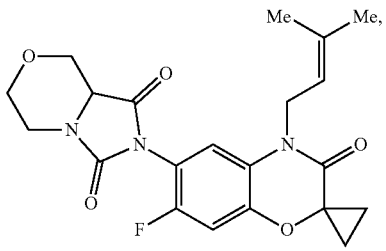

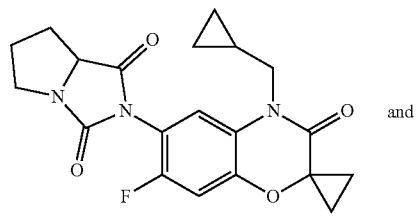 and

-continued

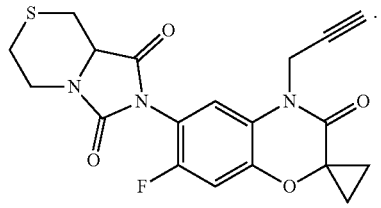

The invention is also described in the following numbered paragraphs:
1. A compound of formula Ia:

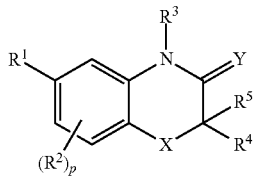

wherein

X is independently selected from $CR^6R^7$, $NR^8$, O, S, S(O) and $S(O)_2$;

Y is independently selected from O and S;

$R^1$ is independently a 5- to 7-membered heterocyclyl group; wherein said heterocyclyl group comprises at least one nitrogen atom in the ring; wherein said heterocyclyl group is optionally unsaturated and is optionally fused to a second ring selected from benzene, 5- or 6-membered heteroaryl, $C_5$-$C_6$-cycloalkyl and 5- to 7-membered heterocycloalkyl; wherein $R^1$ is optionally substituted with from 1 to 6 $R^9$ groups;

or wherein $R^1$ is $-N=CR^{10}R^{11}$ wherein $R^{10}$ and $R^{11}$ together with the carbon atom to which they are attached form a 5- to 9-membered bicyclic or monocyclic heterocyclyl group, wherein said heterocyclyl group is optionally unsaturated; and wherein said heterocyclyl group comprises at least one nitrogen atom in the ring and is optionally substituted with from 1 to 6 $R^9$ groups; $R^2$ is independently at each occurrence selected from $C_1$-$C_6$-alkyl, $C_1$-$C_6$-haloalkyl, halogen, nitro, $OR^{12}$, $SR^{13}$, $OS(O)_2R^{13}$, $S(O)_2R^{13}$, $S(O)_2NR^{13}R^{13}$, $S(O)(NR^{13})R^{13}$, $S(O)R^{13}$, cyano, $C_2$-$C_6$-alkenyl, $C_2$-$C_6$-alkynyl, and $NR^{13}R^{14}$;

$R^3$ is selected from $C_1$-$C_6$-alkyl, $C_1$-$C_6$-haloalkyl, $C_3$-$C_6$-cycloalkyl, $C_1$-$C_3$-alkylene-$C_3$-$C_6$-cycloalkyl, $C_3$-$C_6$-alkenyl, $C_3$-$C_6$-alkynyl and 4- to 6-membered heterocycloalkyl;

$R^4$ and $R^5$ together with the carbon atom to which they are attached form a cyclic group selected from $C_3$-$C_6$-cycloalkyl and a 4- to 6-membered heterocycloalkyl, wherein said heterocycloalkyl group comprises at least one heteroatom selected from N, O and S; and wherein said cycloalkyl group and heterocycloalkyl group is optionally substituted with from 1 to 4 $R^{15}$ groups;

$R^6$, $R^7$ and $R^8$ are each independently selected from H, $C_1$-$C_6$-alkyl and $C_3$-$C_6$-cycloalkyl;

$R^9$ is independently at each occurrence selected from: $=O$, $=S$, $=NR^{13}$, $C_1$-$C_6$-alkyl, $C_1$-$C_6$-haloalkyl, halogen, nitro, $OR^{12}$, $SR^{13}$, $S(O)_2R^{13}$, $S(O)_2NR^{13}R^{13}S(O)(NR^{13})R^{13}$, $S(O)R^{13}$, $C(O)R^{13}$, $C(O)NR^{13}R^{13}$, $C(O)OR^{13}$, cyano, $C_2$-$C_4$-alkenyl, $C_2$-$C_4$-alkynyl, and $NR^{13}R^{14}$;

$R^{12}$ is independently at each occurrence selected from: H, $C_1$-$C_6$-alkyl, $C_3$-$C_6$-cycloalkyl, $C_1$-$C_6$-haloalkyl and 4- to 6-membered heterocycloalkyl;

$R^{13}$ is independently at each occurrence selected from: H, $C_3$-$C_6$-cycloalkyl and $C_1$-$C_6$-alkyl; or where two $R^{13}$ groups are attached to the same nitrogen atom, said $R^{13}$ groups, together with said nitrogen atom form a 4-, 5-, 6- or 7-membered heterocycloalkyl ring;

$R^{14}$ is independently at each occurrence selected from; H, $C_1$-$C_6$-alkyl, $C_3$-$C_6$-cycloalkyl, C(O)—$C_1$-$C_6$-alkyl, $S(O)_2$—$C_1$-$C_6$-alkyl and 4- to 6-membered heterocycloalkyl;

or where a $R^{13}$ group and a $R^{14}$ group are attached to the same nitrogen atom, said $R^{13}$ and $R^{14}$ groups, together with said nitrogen atom form a 4-, 5-, 6- or 7-membered heterocycloalkyl ring;

$R^{15}$ is independently at each occurrence selected from: =O, =S, =$NR^{13}$, $C_1$-$C_6$-alkyl, $C_1$-$C_6$-haloalkyl, halogen, nitro, $OR^{12}$, $SR^{13}$, $S(O)_2R^{13}$, $S(O)_2NR^{13}R^{13}$, $S(O)(NR^{13})R^{13}$, $S(O)R^{13}$, $C(O)R^{13}$, $C(O)NR^{13}R^{13}$, $C(O)OR^{13}$, cyano, $C_2$-$C_4$-alkenyl, $C_2$-$C_4$-alkynyl, and $NR^{13}R^{14}$;

p is an integer selected from 0, 1, 2 and 3;

wherein any $R^2$, $R^3$, $R^6$, $R^7$, $R^8$, $R^9$, $R^{12}$, $R^{13}$ or $R^{14}$ group that is alkyl, alkenyl, alkynyl, cycloalkyl, heterocycloalkyl (including where two $R^{13}$ groups or an $R^{13}$ group and an $R^{14}$ group together with a nitrogen to which they are attached form a heterocycloalkyl ring), or alkylene-cycloalkyl is optionally substituted, where chemically possible, by 1 to 4 substituents which are each independently selected at each occurrence from the group consisting of: =O; =$NR^a$, =$NOR^a$, $C_1$-$C_4$-alkyl, halo, nitro, cyano, $C_1$-$C_4$-haloalkyl, $C_2$-$C_4$-alkenyl, $C_2$-$C_4$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$ and $OR^a$;

wherein $R^a$ is independently selected from H and $C_1$-$C_4$-alkyl; and $R^b$ is independently H, $C_1$-$C_4$-alkyl, C(O)—$C_1$-$C_4$-alkyl, $S(O)_2$—$C_1$-$C_4$-alkyl; or an agronomically acceptable salt or N-oxide thereof.

2. A compound of paragraph 1 wherein X is selected from O and S.

3. A compound of paragraph 1 or paragraph 2, wherein Y is O.

4. A compound of any one of paragraphs 1 to 3, wherein $R^1$ has the structure:

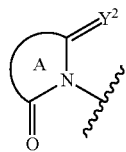

wherein ring A is a 5- or 6-membered heterocyclyl group, wherein said heterocyclyl group is optionally unsaturated and is optionally fused to a 5- or 6-membered cycloalkyl, benzene or 5- or 6-heterocycloalkyl ring; =$Y^2$ is =O or =S and wherein the group $R^1$ is optionally substituted with from 1 to 4 $R^9$ groups.

5. A compound of any one of paragraphs 1 to 3, wherein $R^1$ has the structure:

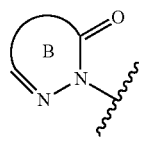

wherein ring B is a 5- or 6-membered heterocyclyl group, wherein said heterocyclyl group is optionally unsaturated; and wherein said heterocyclyl group is optionally fused to a 5- or 6-membered cycloalkyl or heterocycloalkyl ring and wherein the group $R^1$ is optionally substituted with from 1 to 5 $R^9$ groups.

6. A compound of any one of paragraphs 1 to 5, wherein $R^3$ is selected from $C_1$-$C_4$-alkyl, $C_1$-alkylene-$C_3$-cycloalkyl, $C_3$-$C_4$-alkenyl and $C_3$-$C_4$-alkynyl.

7. A compound of claim 6, wherein $R^3$ is propargyl.

8. A compound of any one of paragraphs 1 to 7, wherein $R^4$ and $R^5$ may together with the carbon atom to which they are attached form a $C_3$-$C_6$-cycloalkyl group; wherein the cycloalkyl group is optionally substituted with from 1 to 4 $R^{15}$ groups.

9. A compound of paragraph 8, wherein $R^4$ and $R^5$ together with the carbon atom to which they are attached form a cyclopropyl group; wherein the cyclopropyl group is optionally substituted with from 1 to 4 $R^{15}$ groups.

10. A compound of any one of paragraphs 1 to 7, wherein $R^4$ and $R^5$ may, together with the carbon to which they are attached have the structure:

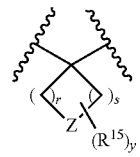

wherein Z is independently selected from —$NR^{16}$—, —O—, —S(O)—, —$S(O)_2$—, —$S(O)NR^{17}$— and —S—; $R^{16}$ is independently selected from $C_1$-$C_4$-alkyl, $S(O)_2R^{13}$C$(O)R^{13}$, $C_3$-$C_4$-alkenyl and $C_3$-$C_4$-alkynyl; $R^{17}$ is independently selected from H, $C_1$-$C_4$-alkyl, $C_3$-$C_4$-alkenyl and $C_3$-$C_4$-alkynyl; y is an integer selected from 0, 1, 2 and 3; r and s are each an integer selected from 1, 2 and 3; and wherein the sum of r and s is 2, 3 or 4.

11. A compound of paragraph 10, wherein Z is $NR^{16}$.

12. A compound of paragraph 10, wherein Z is O.

13. A compound of any one of paragraphs 10 to 12, wherein the sum of r and s is 2.

14. A compound of any one of paragraphs 10 to 12, wherein the sum of r and s is 3.

15. A compound of any one of paragraphs 10 to 12, wherein the sum of r and s is 4.

16. A compound of any one of paragraphs 1 to 3, wherein p is 1 and the single $R^2$ substituent is situated para to the nitrogen that is also attached to $R^3$.

17. A compound of formula II:

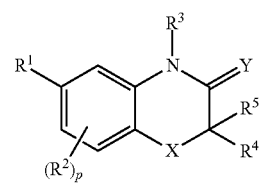

wherein
X is independently selected from $CR^6R^7$, $NR^8$, O, S, S(O) and $S(O)_2$;

Y is independently selected from O and S;
R$^1$ is independently selected from:

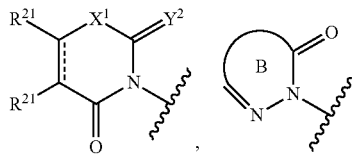

and —N=CR$^{10}$R$^{11}$; wherein R$^{10}$ and R$^{11}$ together with the carbon atom to which they are attached form a 5- to 9-membered bicyclic or monocyclic heterocyclyl group, wherein said heterocyclyl group is optionally unsaturated; and wherein said heterocyclyl group comprises at least one nitrogen atom in the ring and is optionally substituted with from 1 to 6 R$^9$ groups;
wherein ====== is either a carbon-carbon double bond or a carbon-carbon single bond;
=Y$^2$ is =O or =S;
X$^1$ is independently absent or is selected from NR$^{19}$ and CR$^{22}$R$^{22}$;
ring B is a 5- or 6-membered heterocyclyl group, wherein said heterocyclyl group is optionally unsaturated; and wherein said heterocyclyl group is optionally fused to a 5- or 6-membered cycloalkyl or heterocycloalkyl ring and wherein the group R$^1$ is optionally substituted with from 1 to 5 R$^9$ groups;
R$^3$ is selected from C$_1$-C$_6$-alkyl, C$_1$-C$_6$-haloalkyl, C$_3$-C$_6$-cycloalkyl, C$_1$-C$_3$-alkylene-C$_3$-C$_6$-cycloalkyl, C$_1$-C$_3$-alkylene-CO$_2$R$^{13a}$, C$_2$-C$_3$-alkylene-OR$^{13a}$, C$_3$-C$_6$-alkenyl, C$_3$-C$_6$-alkynyl and 4- to 6-membered heterocycloalkyl;
R$^4$ and R$^5$ together with the carbon atom to which they are attached form a cyclic group selected from C$_3$-C$_6$-cycloalkyl and a 4- to 6-membered heterocycloalkyl, wherein said heterocycloalkyl group comprises at least one heteroatom selected from N, O and S; and wherein said cycloalkyl group and heterocycloalkyl group is optionally substituted with from 1 to 4 R$^{15}$ groups;
R$^6$, R$^7$ and R$^8$ are each independently selected from H, C$_1$-C$_6$-alkyl and C$_3$-C$_6$-cycloalkyl;
R$^9$ is independently at each occurrence selected from: =O, =S, =NR$^{13}$, C$_1$-C$_6$-alkyl, C$_1$-C$_6$-haloalkyl, halogen, nitro, OR$^{12}$, SR$^{13}$, S(O)$_2$R$^{13}$, S(O)$_2$NR$^{13}$R$^{13}$, S(O)(NR$^{13}$)R$^{13}$, S(O)R$^{13}$, C(O)R$^{13}$, C(O)NR$^{13}$R$^{13}$, C(O)OR$^{13}$, cyano, C$_2$-C$_6$-alkenyl, C$_2$-C$_6$-alkynyl, and NR$^{13}$R$^{14}$;
R$^{12}$ is independently at each occurrence selected from: H, C$_1$-C$_6$-alkyl, C$_3$-C$_6$-cycloalkyl, C$_1$-C$_6$-haloalkyl and 4- to 6-membered heterocycloalkyl;
R$^{13}$ is independently at each occurrence selected from: H, C$_3$-C$_6$-cycloalkyl and C$_1$-C$_6$-alkyl;
or where two R$^{13}$ groups are attached to the same nitrogen atom, said R$^{13}$ groups, together with said nitrogen atom form a 4-, 5-, 6- or 7-membered heterocycloalkyl ring;
R$^{13a}$ is independently selected from: H, C$_3$-C$_6$-cycloalkyl and C$_1$-C$_6$-alkyl;
R$^{14}$ is independently at each occurrence selected from; H, C$_1$-C$_6$-alkyl, C$_3$-C$_6$-cycloalkyl, C(O)—C$_1$-C$_6$-alkyl, S(O)$_2$—C$_1$-C$_6$-alkyl and 4- to 6-membered heterocycloalkyl;
or where a R$^{13}$ group and a R$^{14}$ group are attached to the same nitrogen atom, said R$^{13}$ and R$^{14}$ groups, together with said nitrogen atom form a 4-, 5-, 6- or 7-membered heterocycloalkyl ring; R$^{15}$ is independently at each occurrence selected from: =O, =S, =NR$^{13}$, C$_1$-C$_6$-alkyl, C$_1$-C$_6$-haloalkyl, halogen, nitro, OR$^{12}$, SR$^{13}$, S(O)$_2$R$^{13}$, S(O)$_2$NR$^{13}$R$^{13}$, S(O)(NR$^{13}$)R$^{13}$, S(O)R$^{13}$, C(O)R$^{13}$, C(O) NR$^{13}$R$^{13}$, C(O)OR$^{13}$, cyano, C$_2$-C$_6$-alkenyl, C$_2$-C$_6$-alkynyl, and NR$^{13}$R$^{14}$;
R$^{21}$ is independently selected from H, halo, C$_1$-C$_4$-alkyl and C$_1$-C$_4$-haloalkyl or two R$^{21}$ groups, together with the carbons to which they are attached form a phenyl ring, a C$_3$-C$_6$-cycloalkyl ring or a 5- or 6-membered bridged bicyclic cycloalkyl ring system, said phenyl or cyclohexyl ring or ring system being optionally substituted with from 1 to 6 R$^9$ groups;
R$^{22}$ is independently at each occurrence selected from H and C$_1$-C$_4$-alkyl; and
p is an integer selected from 0, 1, 2 and 3;
wherein any R$^2$, R$^3$, R$^6$, R$^7$, R$^8$, R$^9$, R$^{12}$, R$^{13}$ or R$^{14}$ group that is alkyl, alkenyl, alkynyl, cycloalkyl, heterocycloalkyl (including where two R$^{13}$ groups or an R$^{13}$ group and an R$^{14}$ group together with a nitrogen to which they are attached form a heterocycloalkyl ring), or alkylene-cycloalkyl is optionally substituted, where chemically possible, by 1 to 4 substituents which are each independently selected at each occurrence from the group consisting of: =O; =NR$^a$, =NOR$^a$, C$_1$-C$_4$-alkyl, halo, nitro, cyano, C$_1$-C$_4$-haloalkyl, C$_2$-C$_4$-alkenyl, C$_2$-C$_4$-alkynyl, NR$^a$R$^b$, S(O)$_2$R$^a$, S(O)R$^a$, S(O)(NR$^a$)R$^a$, S(O)$_2$NR$^a$R$^a$, CO$_2$R$^a$, C(O)R$^a$, CONR$^a$R$^a$ and OR$^a$;
wherein R$^a$ is independently selected from H and C$_1$-C$_4$-alkyl; and R$^b$ is independently H, C$_1$-C$_4$-alkyl, C(O)—C$_1$-C$_4$-alkyl, S(O)$_2$—C$_1$-C$_4$-alkyl; or an agronomically acceptable salt or N-oxide thereof.

18. A compound of paragraph 17 wherein X is selected from O and S.
19. A compound of paragraph 17 or paragraph 18, wherein Y is O.
20. A compound of any one of paragraphs 17 to 19, wherein R$^1$ has the structure:

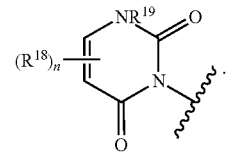

21. A compound of any one of paragraphs 17 to 19, wherein R$^1$ has the structure:

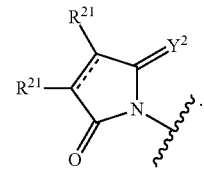

22. A compound of any one of paragraphs 17 to 19, wherein R$^1$ has the structure:

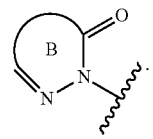

23. A compound of any one of paragraphs 17 to 22, wherein $R^3$ is selected from $C_1$-$C_4$-alkyl, $C_1$-alkylene-$C_3$-$C_4$-cycloalkyl, $C_1$-$C_3$-alkylene-$CO_2R^{13a}$, $C_2$-$C_3$-alkylene-$OR^{13a}$, $C_3$-$C_4$-alkenyl and $C_3$-$C_4$-alkynyl.

24. A compound of paragraph 23, wherein $R^3$ is propargyl.

25. A compound of any one of paragraphs 17 to 24, wherein $R^4$ and $R^5$ may together with the carbon atom to which they are attached form a $C_3$-$C_6$-cycloalkyl group; wherein the cycloalkyl group is optionally substituted with from 1 to 4 $R^{15}$ groups.

26. A compound of paragraph 25, wherein $R^4$ and $R^5$ together with the carbon atom to which they are attached form a cyclopropyl group; wherein the cyclopropyl group is optionally substituted with from 1 to 4 $R^{15}$ groups.

27. A compound of any one of paragraphs 17 to 24, wherein $R^4$ and $R^5$ may, together with the carbon to which they are attached have the structure:

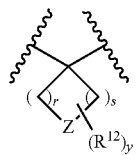

wherein Z is independently selected from —$NR^{16}$—, —O—, —S(O)—, —S(O)$_2$—, —S(O)$NR^{17}$— and —S—; $R^{16}$ is independently selected from $C_1$-$C_4$-alkyl, $S(O)_2R^{13}$, $C(O)R^{13}$, $C_3$-$C_4$-alkenyl and $C_3$-$C_4$-alkynyl; $R^{17}$ is independently selected from H, $C_1$-$C_4$-alkyl, $C_3$-$C_4$-alkenyl and $C_3$-$C_4$-alkynyl; y is an integer selected from 0, 1, 2 and 3; r and s are each an integer selected from 1, 2 and 3; and wherein the sum of r and s is 2, 3 or 4.

28. A compound of paragraph 27, wherein Z is $NR^{16}$

29. A compound of paragraph 27, wherein Z is O.

30. A compound of any one of paragraphs 27 to 29, wherein the sum of r and s is 2.

31. A compound of any one of paragraphs 27 to 29, wherein the sum of r and s is 3.

32. A compound of any one of paragraphs 27 to 29, wherein the sum of r and s is 4.

33. A compound of any one of paragraphs 17 to 32, wherein p is 1 and the single $R^2$ substituent is situated para to the nitrogen that is also attached to $R^3$.

34. A method for controlling weeds, the method comprising applying a compound of any one of paragraphs 1 to 33 to the plants themselves or to the area where it is intended that the plants will grow.

35. Use of a compound of any one of paragraphs 1 to 33 as a herbicide.

36. A herbicidal composition comprising an effective amount of an active compound of any one of paragraphs 1 to 33.

DETAILED DESCRIPTION

The term $C_m$-$C_n$ refers to a group with m to n carbon atom(s).

The term "alkyl" refers to a monovalent linear or branched saturated hydrocarbon chain. For example, $C_1$-$C_6$-alkyl may refer to methyl, ethyl, n-propyl, iso-propyl, n-butyl, sec-butyl, tert-butyl, n-pentyl and n-hexyl. The alkyl groups may be unsubstituted.

The term "alkylene" refers to a divalent linear saturated hydrocarbon chain. For example, $C_1$-$C_3$-alkylene may refer to a substituted or unsubstituted carbon chain that is 1, 2 or 3 carbons in length, e.g. —$CH_2$—, —$CH_2CH_2$—, or —$CH_2CH_2CH_2$—. The alkylene groups may be substituted, including with alkyl groups. The alkylene groups may be unsubstituted.

The term "haloalkyl" refers to a hydrocarbon chain substituted with at least one halogen atom independently chosen at each occurrence from: fluorine, chlorine, bromine and iodine. The halogen atom may be present at any position on the hydrocarbon chain. For example, $C_1$-$C_6$-haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A haloalkyl group may be a fluoroalkyl group, i.e. a hydrocarbon chain substituted with at least one fluorine atom. Thus, a haloalkyl group may have any amount of halogen substituents. The group may contain a single halogen substituent, it may have two or three halogen substituents, or it may be saturated with halogen substituents.

The term "alkenyl" refers to a branched or linear hydrocarbon chain containing at least one double bond. The double bond(s) may be present as the E or Z isomer. The double bond may be at any possible position of the hydrocarbon chain. For example, "$C_2$-$C_6$-alkenyl" may refer to ethenyl, propenyl, butenyl, butadienyl, pentenyl, pentadienyl, hexenyl and hexadienyl. The alkenyl groups may be unsubstituted. An allyl group is an example of an unsubstituted propenyl group: —$CH_2$—CH=$CH_2$.

The term "alkynyl" refers to a branched or linear hydrocarbon chain containing at least one triple bond. The triple bond may be at any possible position of the hydrocarbon chain. For example, "$C_2$-$C_6$-alkynyl" may refer to ethynyl, propynyl, butynyl, pentynyl and hexynyl. The alkynyl groups may be unsubstituted. A propargyl group is an example of an unsubstituted propynyl group: —$CH_2$—C≡CH.

The term "cycloalkyl" refers to a saturated hydrocarbon ring system containing carbon atoms. For example, "$C_3$-$C_6$-cycloalkyl" may refer to cyclopropyl, cyclobutyl, cyclopentyl, cyclohexyl. The cycloalkyl groups may be unsubstituted.

The term "cycloalkenyl" refers to an unsaturated hydrocarbon ring system containing carbon atoms. Examples include cyclohexene.

The term y-membered heterocycloalkyl group may refer to a monocyclic or bicyclic saturated or partially saturated group having y atoms in the ring system and comprising 1 or 2 heteroatoms independently selected from O, S and N in the ring system (in other words 1 or 2 of the atoms forming the ring system are selected from O, S and N). By partially saturated it is meant that the ring may comprise one or two double bonds. This applies particularly to monocyclic rings with from 5 to 6 members. The double bond will typically be between two carbon atoms but may be between a carbon atom and a nitrogen atom. Unless otherwise specified, the term y- to z-membered heterocycloalkyl group may refer to a monocyclic or bicyclic saturated group having from y to z atoms in the ring system. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane, azepine. A heterocycloalkyl group may be unsubstituted.

Aryl groups may be any aromatic carbocyclic ring system (i.e. a ring system containing 2(2n+1)π electrons). Aryl groups may have from 6 to 12 carbon atoms in the ring system. Aryl groups will typically be phenyl groups. Aryl groups may be naphthyl groups or biphenyl groups.

In any of the above aspects and embodiments, heteroaryl groups may be any aromatic (i.e. a ring system containing 2(2n+1)π electrons or n electrons that can overlap with the π system) 5 or 6 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 1-4 heteroatoms independently selected from O, S and N; and 6-membered heteroaryl groups in which the heteroaromatic ring is substituted with 1-3 (e.g. 1-2) nitrogen atoms. Specifically, heteroaryl groups may be independently selected from: pyrrole, furan, thiophene, pyrazole, imidazole, oxazole, isoxazole, triazole, oxadiazole, thiadiazole, tetrazole; pyridine, pyridazine, pyrimidine, pyrazine, triazine.

The term heterocyclyl group encompasses unsaturated, partially saturated and fully saturated heterocyclyl rings. Thus, heterocyclyl groups may be either heterocycloalkyl groups or heteroaryl groups.

Compounds of the invention containing one or more asymmetric carbon atoms can exist as two or more stereoisomers. Where a compound of the invention contains a double bond such as a C=C or C=N group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

The compounds of the invention may be obtained, stored and/or used in the form of an agronomically acceptable salt. Suitable salts include, but are not limited to, salts of acceptable inorganic acids such as hydrochloric, sulfuric, phosphoric, nitric, carbonic, boric, sulfamic, and hydrobromic acids, or salts of agronomically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Suitable salts also include salts of inorganic and organic bases, e.g. counterions such as Na, Ca, K, Li, Mg, ammonium, trimethylsulfonium. The compounds may also be obtained, stored and/or used in the form of an N-oxide.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high performance liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The activity of the compounds of the present invention can be assessed by a variety of in silico, in vitro and in vivo assays. In silico analysis of a variety of compounds has been demonstrated to be predictive of ultimate in vitro and even in vivo activity.

The present invention also includes all environmentally acceptable isotopically-labelled compounds of formulae I to XVI and their syntheses, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

If appropriate, the compounds of the invention can, at certain concentrations or application rates, be used as herbicides.

According to another aspect of the present invention, there is provided a method for controlling weeds, the method comprising applying a compound according to the invention to the weeds themselves or to the area where it is intended that the crop plants will grow. Where the crop plants are already growing or have recently been sown, an agronomically effective and substantially non-phytotoxic (to the crop plant) quantity of the compound according to the invention may be applied.

The herbicide may be applied as a foliar application, stem application, drench or drip application (chemigation) to the plant or to the fruit of the plant or to soil or to inert substrate (e.g. inorganic substrates like sand, rockwool, glasswool; expanded minerals like perlite, vermiculite, zeolite or expanded clay), Pumbe, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics).

In a further aspect, the present invention also relates to a herbicidal composition comprising an effective amount of an active compound of the invention. The composition may further comprise one or more additional herbicides.

The term "effective and non-phytotoxic amount" means an amount of pesticide according to the invention which is sufficient to control or destroy any of the targeted weeds present or liable to appear in the crops and which does not have any significant detrimental effect on the crops or indeed has a positive effect on plant vigour and yield in the absence of target organism. The amount will vary depending on the weed or weeds to be controlled, the type of crop, the climatic conditions and the compounds included in the herbicidal composition. This amount can be determined by systematic field trials, which are within the capabilities of a person skilled in the art.

Depending on their particular physical and/or chemical properties, the active compounds of the invention can be formulated as solutions, emulsions, suspensions, powders, foams, pastes, granules, aerosols, microencapsulations in polymeric substances and also as ULV cold and warm fogging formulations.

The active compounds can be used neat, or in the form of a formulation, e.g. ready-to-use solutions, emulsions, water- or oil-based suspensions, powders, wettable powders, pastes, soluble powders, dusts, soluble granules, granules for broadcasting, suspoemulsion concentrates, natural substances impregnated with active compound, synthetic substances impregnated with active compound, fertilizers and also microencapsulations in polymeric substances. Application may be carried out, for example, by watering, spraying, atomizing, broadcasting, dusting, foaming, spreading, etc. It is also possible to apply the active compounds by the ultra-low volume method or to inject the preparation of active compound or the active compound itself into the soil.

Formulations containing the compounds of the invention are produced in a known manner, for example by mixing the compounds with extenders (e.g. liquid solvents and/or solid carriers), optionally with the use of surfactants (e.g. emulsifiers and/or dispersants and/or foam-formers). The formulations are prepared either in factories/production plants or alternatively before or during the application.

Auxiliaries are substances which are suitable for imparting to the composition itself and/or to preparations derived therefrom (for example spray liquors) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and also their ethers and esters, ketones such as acetone, methyl ethyl ketone, methyl isobutyl ketone or cyclohexanone, strongly polar solvents such as dimethylformamide and dimethyl sulfoxide.

Suitable solid carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulfates, alkyl- or arylsulfonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulfonic acid derivatives, unmodified and modified celluloses, aromatic and/or aliphatic sulfonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

Further additives may be mineral and vegetable oils. It is also possible to add colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. Other possible additives are perfumes, mineral or vegetable, optionally modified oils and waxes.

The formulations may also comprise stabilizers, e.g. low-temperature stabilizers, preservatives, antioxidants, light stabilizers or other agents which improve chemical and/or physical stability.

The formulations generally comprise between 0.01 and 98% by weight of active compound, preferably between 0.1 and 95% and particularly preferably between 0.5 and 90%.

The active compounds according to the invention can also be used as a mixture with other known herbicides for example, to improve the activity spectrum or to reduce or slow the development of resistance.

A mixture with other known active compounds such as nematicides, acaricides, fungicides, insecticides or bactericides, or with fertilizers and growth regulators, safeners or semiochemicals is also possible.

Exemplary application rates of the active compounds according to the invention are: when treating leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used); when treating the soil: from 0.1 to 10 000 g/ha, preferably from 1 to 5000 g/ha.

A formulation which could be used to administer the compounds, particularly in the context of testing for activity, would be to supply all compounds as a 10% solution in DMSO. If there are solubility problems this can be helped by adding acetone (e.g. to dilute a DMSO solution/suspension by 50% resulting in a 5% solution of the compound in DMSO/acetone. The administration formulation is then obtained by adding the DMSO (or DMSO/acetone) solution to a 0.1% solution of Tween 20™ in water to give the required concentration. The result is likely to be an emulsion that can be sprayed. If crystallisation occurs, resulting in inconsistent results, further DMSO can be added to the test solution.

The compositions according to the invention are suitable for protecting any plant variety which is employed in agriculture, in the greenhouse, in forests or in horticulture and, in particular, cereals (e.g. wheat, barley, rye, millet and oats), maize, cotton, soya beans, rice, potatoes, sunflowers, beans, coffee, beet (for example sugar beet and fodder beet), peanuts, vegetables (e.g. tomatoes, cucumbers, onions and lettuce), lawns, fruit and nut trees (e.g. apples pears peaches nectarines, apricots, hazelnut, pecan, macadamia, pistachio), soft fruit (e.g. strawberries, raspberries, blackcurrants, redcurrants), grapevines, bananas, cocoa and ornamental plants.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular nematodes, which are encountered in agriculture, in horticulture, in animal husbandry, in forests, in gardens and leisure facilities, in the protection of stored products and of materials, and in the hygiene sector. They may be preferably employed as crop protection agents.

Use as Herbicides

The compounds of the invention can be used as herbicides. Some compounds of the invention may also have herbicidal activity against a broad spectrum of economically important mono- and dicotyledonous harmful plants. Some compounds of the invention may have herbicidal activity against monocotyledonous plants but no activity or little activity against dicotyledonous crops. Other compounds of the invention may be selective, having excellent herbicidal activity against dicotyledonous plants but no activity or little activity against monocotyledonous crops.

Difficult-to-control perennial weeds which produce shoots from rhizomes, root stocks or other perennial organs may also be controlled by herbicidal compounds. Here, the substances can be applied by the pre-sowing method, the pre-emergence method and/or the post-emergence method.

The following are illustrative examples of monocotyledonous weeds that may be controlled by herbicidal compounds: *Avena* spp., *Alopecurus* spp., *Brachiaria* spp., *Digitaria* spp., *Lolium* spp., *Echinochloa* spp., *Panicum* spp., *Phalaris* spp., Poa spp., *Setaria* spp. and also *Bromus* spp. such as *Bromus catharticus, Bromus secalinus, Bromus erectus, Bromus tectorum* and *Bromus japonicus* and *Cyperus* species from the annual group, and, *Agropyron, Cynodon, Imperata* and Sorghum and also perennial *Cyperus* species, from the perennial group.

The following are illustrative examples of dicotyledonous weeds that may be controlled by herbicidal compounds: *Abutilon* spp., *Amaranthus* spp., *Chenopodium* spp., *Chrysanthemum* spp., *Galium* spp. such as *Galium aparine, Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., in the case of annuals, and *Convolvulus, Cirsium, Rumex* and *Artemisia* in the case of the perennials.

If herbicidal compounds are applied to the soil surface before or during germination, the weed seedlings are inhibited or prevented completely from emerging or else the weeds grow until they have reached the cotyledon stage, but then their growth stops, and, eventually, they die completely.

If herbicidal compounds are applied post-emergence to the green parts of the plants, growth typically stops following the treatment, and the weed plants remain substantially at the growth stage of the point of time of application, or they die completely, so that in this manner competition from the weeds is eliminated quickly and in a sustained manner.

The testing of herbicides is not typically conducted in a sterile in vitro laboratory test. Herbicides are typically tested by spraying live plants or soil where seeds have been sown. There is typically greater variation in results obtained from such testing than might be the case in more controlled testing regimes that have been conducted in vitro.

DETAILED DESCRIPTION—SYNTHESIS

The skilled person will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", RC Larock, Wiley-VCH (1999 or later editions); "March's Advanced Organic Chemistry—Reactions, Mechanisms and Structure", M B Smith, J. March, Wiley, (5th edition or later); "Advanced Organic Chemistry, Part B, Reactions and Synthesis", F A Carey, R J Sundberg, Kluwer Academic/Plenum Publications, (2001 or later editions); "Organic Synthesis—The Disconnection Approach", S Warren (Wiley), (1982 or later editions); "Designing Organic Syntheses" S Warren (Wiley) (1983 or later editions); "Heterocyclic Chemistry", J. Joule (Wiley 2010 edition or later); "Guidebook To Organic Synthesis" R K Mackie and D M Smith (Longman) (1982 or later editions), etc., and the references therein as a guide.

The skilled person is familiar with a range of strategies for synthesising organic and particularly heterocyclic molecules and these represent common general knowledge as set out in text books such as Warren "Organic Synthesis: The Disconnection Approach"; Mackie and Smith "Guidebook to Organic Chemistry"; and Clayden, Greeves, Warren and Wothers "Organic Chemistry".

The skilled chemist will exercise his or her judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by TW Greene and PGM Wuts, John Wiley & Sons Inc (1999), and references therein.

Throughout this specification these abbreviations have the following meanings:

Boc—tert-Butyloxycarbonyl DCM—dichloromethane
DMF—N,N-dimethylformamide DIPEA—diisopropylethylamine
DMAP—N,N-dimethylaminopyridine DMSO—dimethylsulfoxide
EtOAc—Ethyl acetate conc.—concentrated
PE—petroleum ether THF—tetrahydrofuran
TFA—trifluoroacetic acid MeOH—methanol
HPLC—high performance liquid chromatography RT—room temperature
h—hour HATU—1-[Bis(dimethylamino)methylene]-1H-1,2,3-triazolo[4,5-b]pyridinium 3-oxid hexafluorophosphate Certain compounds of the invention can be made according to the following general synthetic schemes. Certain compounds of the invention can be made according to or analogously to the methods described in Examples 1 to 34.

General Synthetic Schemes

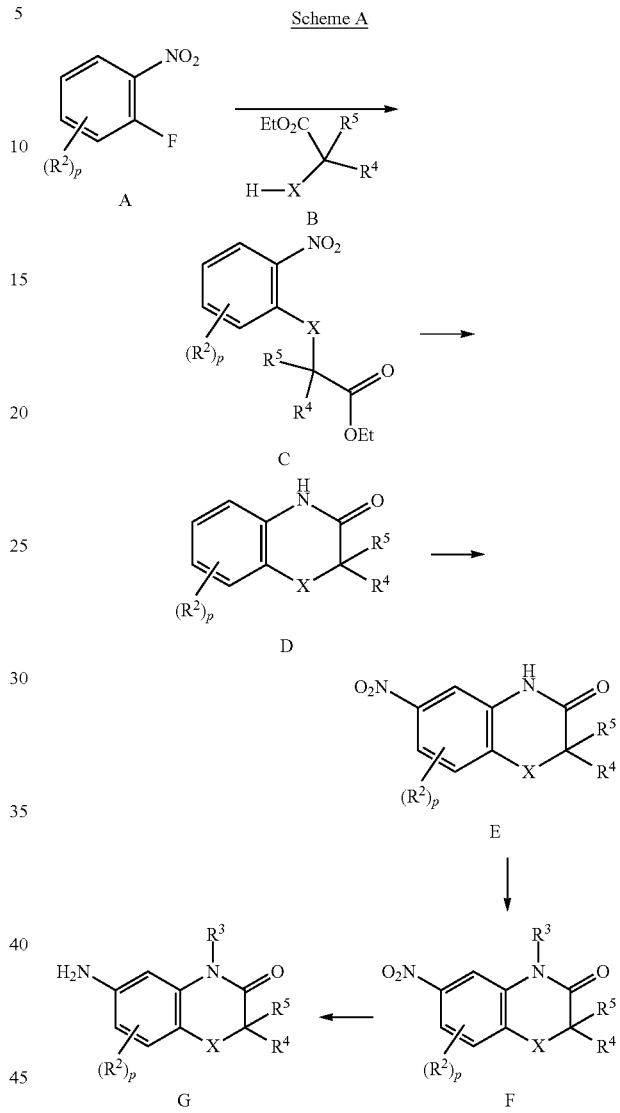

Certain intermediates useful in the synthesis of compounds of the invention can be made according to scheme A. A compound of formula A can react with a compound of formula B (where X is O, S or NR$^8$) in the presence of a base (for example, sodium hydride and 15-crown-5 at 0° C. to room temperature) to form a compound of formula C. Compound C can undergo reduction (e.g. using Fe and acetic acid at 60° C.) and subsequently cyclises to form a compound of formula D. Compound D can be nitrated (for example, using nitric acid and sulfuric acid at 0° C.) to form a compound of formula E. Compound E can react with R$^3$-LG (LG is a leaving group, e.g. C$_1$ or Br) in the presence of a base (for example, potassium carbonate in DMF at room temperature) to form a compound of formula F. The nitro group of compound F can be reduced to an amino group yielding a compound of formula G (for example, using Fe, NH$_4$Cl in methanol, THF, H$_2$O at 70° C.).

Scheme B

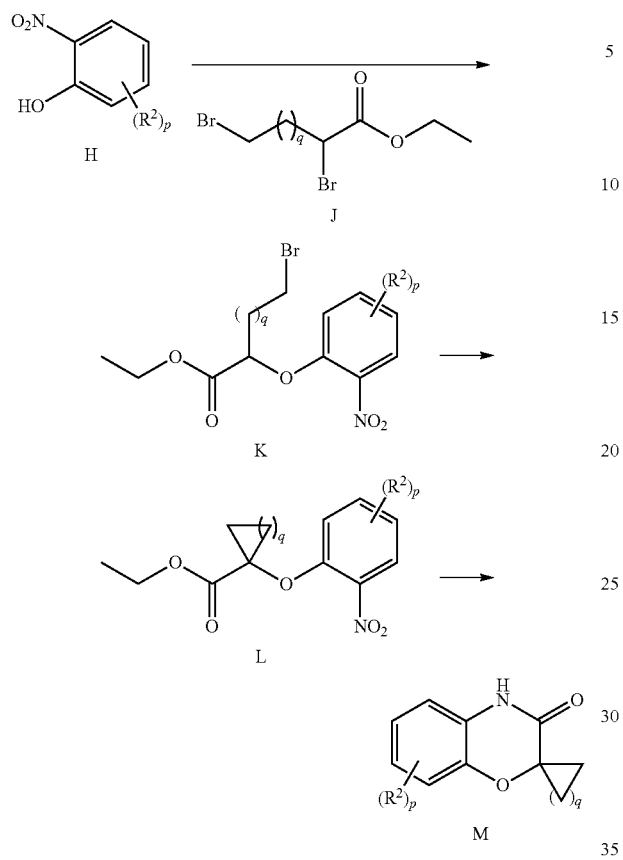

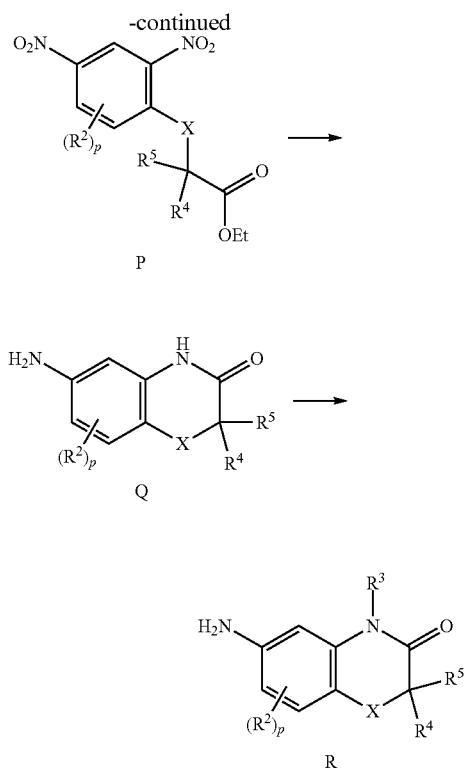

Further intermediates useful in the synthesis of compounds of the invention can be made according to scheme B. A nitrophenol compound of formula H can react with a dibromo ester of formula J in the presence of a base (for example, potassium carbonate in DMF at room temperature) to form a compound of formula K. Compound K can undergo a cyclisation reaction in the presence of a base (for example, potassium tert-butoxide in THF at room temperature) to form a compound of formula L. Compound L can undergo reduction in the presence of a reducing agent (for example, Fe and acetic acid at 60° C.) and in situ cyclisation to form a compound of formula M (a subset of compounds of formula D from Scheme A and which can be converted to the corresponding amino benzene as described in Scheme A).

Scheme C

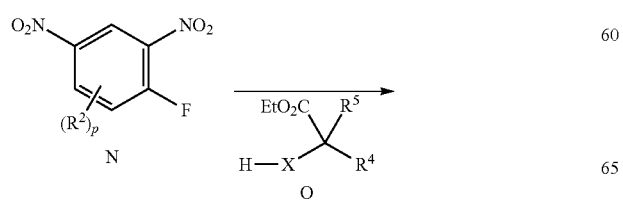

Further intermediates useful in the synthesis of compounds of the invention can be made according to scheme C. A compound of formula N can react with a compound of formula O (where X is O, S or $NR^8$) in the presence of a base (for example, triethylamine in dichloromethane at room temperature) to form a compound of formula P. Compound P can undergo reduction (using, for example, palladium on carbon and hydrogen in ethanol and dioxane at room temperature) and subsequent cyclisation can form a compound of formula Q. Compound Q can react with $R^3$—X in the presence of a base (for example sodium hydride in DMF at room temperature) to form a compound of formula R.

Scheme D

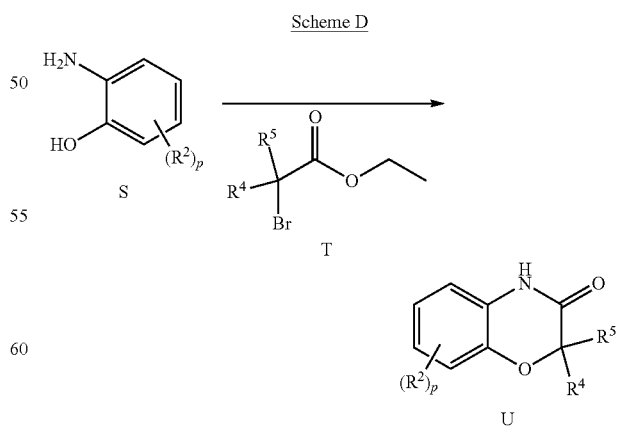

Further intermediates useful in the synthesis of compounds of the invention can be made according to scheme D. A compound of formula S can react with a compound of formula T (e.g. in the presence of KF in DMF at room temperature) to form a compound of formula U (a subset of compounds of formula D from Scheme A and which can be converted to the corresponding amino benzene as described in Scheme A).

Scheme E

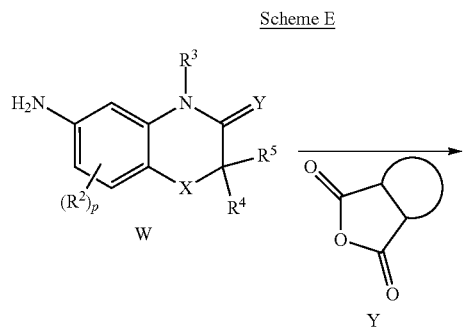

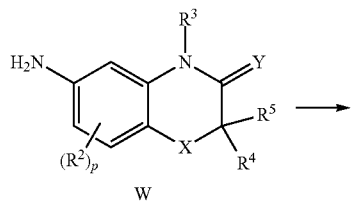

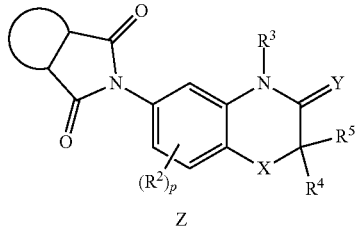

Certain compounds of the invention can be made according to scheme E. A compound of formula W (which can, for example, be made according to either scheme A or scheme C) can react with a compound of formula Y in the presence of acetic acid at 120° C. to form compounds of formula Z (a subset of compounds of formula I and formula II).

Scheme F

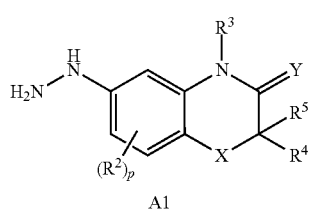
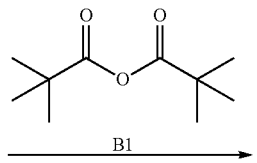
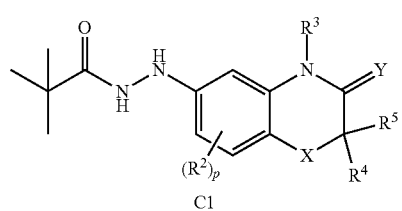

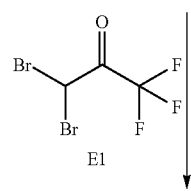

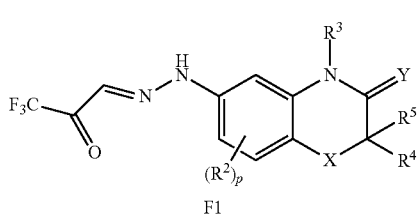

F1

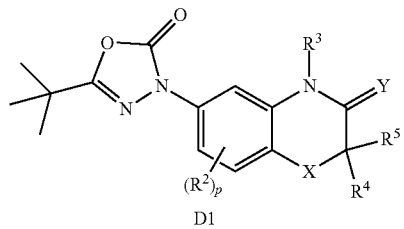

D1

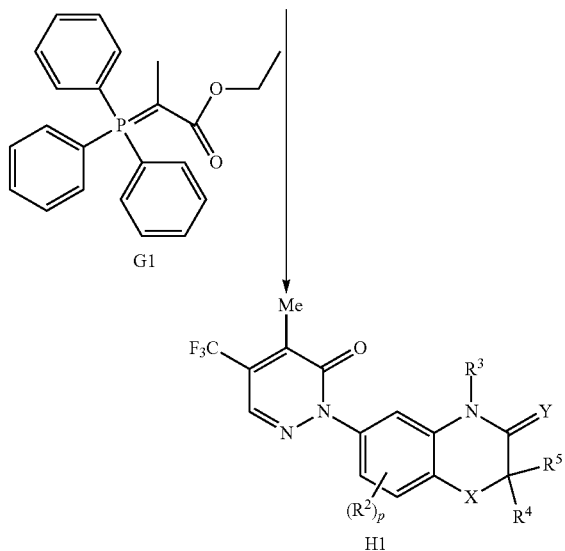

G1

H1

Certain compounds of the invention can be made according to scheme F. A compound of formula W (which can, for example, be made according to either scheme A or scheme C) can be converted (e.g. with i) NaNO₂, HCl at 0° C. and ii) SnCl₂, HCl at 0° C.) to a compound of formula A1. Compound A1 can react with a compound of formula B1 in the presence of a base (for example, triethylamine in dichloromethane at room temperature) to form a compound of formula C1. Compound C1 can react with triphosgene in toluene at 110° C. to form compounds of formula D1 (a subset of compounds of the formula I and formula II). Alternatively, compound A1 can react with a compound of formula E1 (e.g. in the presence of sodium acetate at 0° C.) to form a compound of formula F1. Compound F1 can react with a triphenylphosphine compound of formula G1 (e.g. in toluene in a microwave at 110° C.) to form compounds of formula H1 (a subset of compounds of the formula I and formula II).

Scheme G

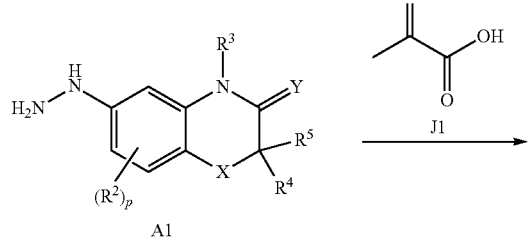

A1

J1

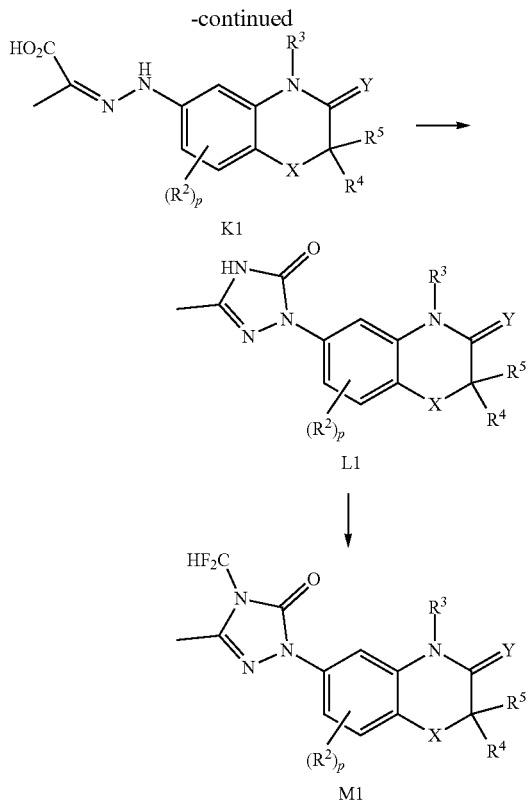

K1

L1

M1

Certain compounds of the invention can be made according to scheme G. A compound of formula A1 can react with compound J1 in water at room temperature to form a compound of formula K1. Compound K1 can be rearranged and cyclised using diphenylphosphoryl azide, triethylamine in toluene at 100° C. to form a compound of formula L1. Compound L1 can react with $CHClF_2$, potassium carbonate in DMF at 100° C. to form a compound of formula M1 (a subset of compounds of the formula I and formula II).

Scheme H

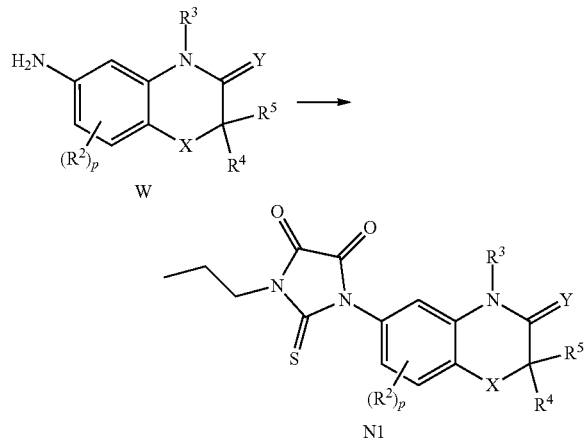

Certain compounds of the invention can be made according to scheme H. A compound of formula W (which can, for example, be made according to either scheme A or C) can be treated with triphosgene and propylamine (e.g. in the presence of $NaHCO_3$, THF, at 0° C.) and subsequently treated with oxalyl chloride (e.g. in the presence of trimethylamine in THF at room temperature) to form a compound of formula N1 (a subset of compounds of the formula (I)).

Scheme I

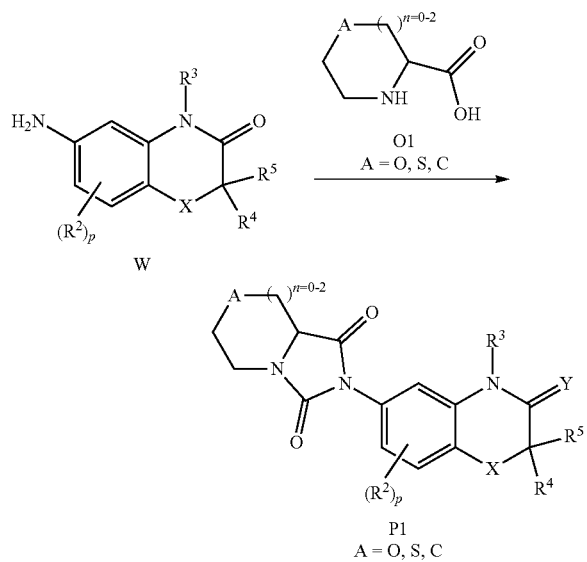

Certain compounds of the invention can be made according to scheme I. A compound of formula W (which can, for example, be made according to either scheme A or C) can be treated with triphosgene or CDI and amino acid O1 (e.g. in the presence of DIPEA and a solvent, e.g. DCM or THF) and subsequently treated with an acid (e.g. 4M HCl in dioxane at 70° C.) to form a compound of formula P1 (a subset of compounds of the formula (I)).

EXAMPLES

General Methods

Flash chromatography was carried out using a Biotage Isolera 4, with Biotage® SNAP KP-Sil cartridges, packed with 50 μm silica particles with a surface area of 500 $m^2/g$, or alternative cartridges (e.g. Puriflash, produced by Interchim) where stated, or using silica gel (40-63 μm particles). Visualisation was carried out with UV light (254 nm) and by staining with either potassium permanganate, phosphomolybdic acid (PMA) or ninhydrin solutions.

All $^1H$ NMR spectra were obtained on a Bruker AVIII 400 with 5 mm QNP or Bruker AVI 500 with 5 mm QNP. Chemical shifts are expressed in parts per million (δ) and are referenced to the solvent. Coupling constants J are expressed in Hertz (Hz).

MS was carried out on a Waters Alliance ZQ MS, using a YMC-Triart C18 50×2 mm, 5 micron LC column (solvent: 5-90% gradient of acetonitrile in water (with 1% by volume of 28% (by weight) aqueous ammonia solution)) by Method A or B, or (solvent: 5-90% gradient of acetonitrile in water (with 1% formic acid) by Method C or D. Flow rate 0.8 mL/min. Wavelengths were 254 and 210 nm.

Method A (5 Minute Basic pH)

Column: YMC-Triart C18 50×2 mm, 5 μm. Flow rate: 0.8 mL/min. Injection volume: 5 μL.

| Mobile Phase | A | $H_2O$ | |
|---|---|---|---|
| | B | $CH_3CN$ | |
| | C | 50% $H_2O$/50% $CH_3CN$ + 1.0% ammonia (aq.) | |
| Time (min) | A (%) | B (%) | C (%) |
| 0 | 95 | 0 | 5 |
| 4 | 0 | 95 | 5 |
| 4.4 | 0 | 95 | 5 |
| 4.5 | 95 | 5 | 0 |
| 4.5 | STOP | | |

Method B (15 Minute Basic pH)

Column YMC Triart-C18 50×2 mm, 5 μm Flow rate: 0.8 mL/min. Injection volume: 5 μL

| Mobile Phase | A | $H_2O$ | |
|---|---|---|---|
| | B | $CH_3CN$ | |
| | C | 50% $H_2O$/50% $CH_3CN$ + 1.0% $NH_3$ | |
| Time (min) | A (%) | B (%) | C (%) |
| 0 | 95 | 0 | 5 |
| 2.0 | 95 | 0 | 5 |
| 12.0 | 0 | 95 | 5 |
| 14.0 | 0 | 95 | 5 |
| 14.2 | 95 | 0 | 5 |

Method C (5 Minute Acidic pH)

Column: YMC-Triart C18 50×2 mm, 5 μm. Flow rate: 0.8 mL/min. Injection volume: 5 μL.

| Mobile Phase | A | $H_2O$ | |
|---|---|---|---|
| | B | $CH_3CN$ | |
| | C | 50% $H_2O$/50% $CH_3CN$ + 1.0% formic acid | |
| Time (min) | A (%) | B (%) | C (%) |
| 0 | 95 | 0 | 5 |
| 4 | 0 | 95 | 5 |
| 4.4 | 0 | 95 | 5 |

-continued

| | | | |
|---|---|---|---|
| 4.5 | 95 | 5 | 0 |
| 4.5 | STOP | | |

Method D (15 Minute Acidic pH)

Column YMC Triart-C18 50×2 mm, 5 µm Flow rate: 0.8 mL/min. Injection volume: 5 µL

| Mobile Phase | A | $H_2O$ | |
| | B | $CH_3CN$ | |
| | C | 50% $H_2O$/50% $CH_3CN$ + 1.0% formic acid | |
| Time (min) | A (%) | B (%) | C (%) |
|---|---|---|---|
| 0 | 95 | 0 | 5 |
| 2.0 | 95 | 0 | 5 |
| 12.0 | 0 | 95 | 5 |
| 14.0 | 0 | 95 | 5 |
| 14.2 | 95 | 0 | 5 |

Alternatively, MS was carried on a Waters Acquity UPLC-QDA UV-MS system using Method E (high pH) or Method F (low pH):

Method E (3.5 Minute Basic pH)

Mobile phases: Water (A)/Acetonitrile (B) both with 0.1% (v/v) Ammonia

| Time | % A | % B | Flow rate (mL/min) |
|---|---|---|---|
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: BEH C18 2.1×50 mm, 1.7 µm @ 50° C.

Method F (3.5 Minute Acidic pH)

Mobile phases: Water (A)/Acetonitrile (B) both with 0.1% (v/v) Formic Acid

| Time | % A | % B | Flow rate (mL/min) |
|---|---|---|---|
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: CSH C18 2.1×50 mm, 1.7 µm @ 50° C.

All reagents were obtained from commercial suppliers and used as supplied unless otherwise stated.

All examples are named using ChemBioDraw Ultra 14.0.

Intermediate 1: Ethyl 1-(5-fluoro-2-nitrophenoxy)cyclopropane-1-carboxylate

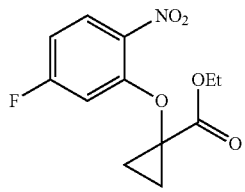

Ethyl-1-hydroxycyclopropanecarboxylate (0.491 g, 3.77 mmol) was dissolved in THF (5 mL) and cooled to 0° C. Sodium hydride (0.181 g, 4.53 mmol) was added and the reaction was stirred for 20 mins. 2,4-Difluoronitrobenzene (0.414 mL, 3.77 mmol) was then added followed by 15-crown-5 (0.015 mL, 0.075 mmol) and the reaction was stirred at room temperature for 18 h. The reaction was treated with aqueous $NH_4Cl$ and extracted with DCM. The organics were dried over $MgSO_4$ and concentrated in vacuo. The crude product was purified by chromatography ($SiO_2$, 0-50% EtOAc in PE) and the title compound was isolated as a yellow solid (622 mg, 61%). $^1H$ NMR $\delta_H$(500 MHz, $CDCl_3$) δ 7.94 (dd, J=9.1, 5.9 Hz, 1H), 6.86 (dd, J=10.1, 2.5 Hz, 1H), 6.78 (ddd, J=9.1, 7.3, 2.5 Hz, 1H), 4.21 (q, J=7.1 Hz, 2H), 1.74-1.64 (m, 2H), 1.49-1.38 (m, 2H), 1.20 (t, J=7.1 Hz, 3H).

Intermediate 2: 7-Fluorospiro[benzo[b][1,4]oxazine-2,1'-cyclopropan]-3(4H)-one

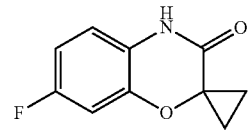 [SMILES: O=C1Nc2ccc(F)cc2OC12CC2]

Intermediate 1 (394 mg, 1.46 mmol) was dissolved in acetic acid (5 mL) and iron powder (817 mg, 14.6 mmol) was added. The reaction was heated to 60° C. for 3 hrs. The reaction was cooled, filtered through Celite®, and washed with DCM. The organics were washed with $NaHCO_3$ and brine, dried over $MgSO_4$ and concentrated in vacuo to give the title compound as a cream solid (283 mg, quantitative yield). $^1H$ NMR $\delta_H$ (500 MHz, $CDCl_3$) 8.87 (s, 1H), 6.75 (dd, J=8.6, 5.3 Hz, 1H), 6.68 (td, J=8.4, 2.7 Hz, 1H), 6.62 (dd, J=9.0, 2.6 Hz, 1H), 1.49-1.41 (m, 2H), 1.28-1.21 (m, 2H).

Intermediate 3: 7-Fluoro-6-nitro-4-(prop-2-yn-1-yl)spiro[benzo[b][1,4]oxazine-2,1'-cyclopropan]-3(4H)-one

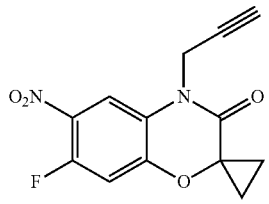

Stage 1: Intermediate 2 (250 mg, 1.29 mmol) was dissolved in conc. sulfuric acid (2.5 mL, 47 mmol) and cooled to 0° C. Conc. nitric acid (85 µL, 1.3 mmol) was added, followed by conc. sulfuric acid (2.5 mL, 47 mmol), and the reaction was stirred at 0° C. for 30 min. The reaction mixture was poured onto iced water and a yellow precipitate formed. After stirring for 10 min, the suspension was filtered, and the solid washed with water. The solid was dried at RT under vacuum for 1 h (with a nitrogen stream) to yield crude 7-fluoro-6-nitrospiro[benzo[b][1,4]oxazine-2,1'-cyclopropan]-3(4H)-one as a yellow solid (252 mg, 82%).

Stage 2: The product from Stage 1 (252 mg, 1.06 mmol) was dissolved in DMF (2.5 mL). Potassium carbonate (175 mg, 1.27 mmol) was added, followed by propargyl bromide, 80% in toluene (137 µL, 1.27 mmol). After stirring at RT for 18 h, the reaction mixture was partitioned between EtOAc and water. The aqueous layer was extracted with EtOAc (×3). The combined EtOAc layers were washed (brine), dried (MgSO$_4$) and concentrated in vacuo. The residue was purified by chromatography (SiO$_2$, 0-25% EtOAc in PE) and the title compound was isolated as an orange oil (189 mg, 65%). $^1$H NMR $\delta_H$ (500 MHz, CDCl$_3$) 7.96 (d, J=7.0 Hz, 1H), 6.83 (d, J=10.9 Hz, 1H), 4.77 (d, J=2.5 Hz, 2H), 2.37 (t, J=2.5 Hz, 1H), 1.58 (dd, J=8.6, 5.6 Hz, 2H), 1.34 (dd, J=8.5, 5.5 Hz, 2H).

Intermediate 4: 6-Amino-7-fluoro-4-(prop-2-yn-1-yl)spiro[benzo[b][1,4]oxazine-2,1'-cyclopropan]-3(4H)-one

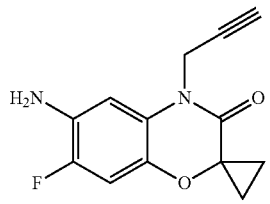 [SMILES: C#CCN1C(=O)C2(CC2)Oc2cc(F)c([N+](=O)[O-])cc21]

Intermediate 3 (189 mg, 0.684 mmol) was dissolved in a mixture of THF (4 mL) and MeOH (2 mL). Ammonium chloride (110 mg, 2.05 mmol) was dissolved in water (0.75 mL) and added to the reaction along with iron powder (115 mg, 2.05 mmol). The reaction mixture was heated to 70° C. for 5 h, then cooled to RT. The reaction mixture was diluted with EtOAc and water and filtered through Dicalite®. The aqueous layer was extracted with EtOAc (×3). The combined EtOAc layers were washed (brine), dried (MgSO$_4$) and concentrated in vacuo to yield the title compound as a brown solid (135 mg, 80%). $^1$H NMR $\delta_H$ (500 MHz, CDCl$_3$) 6.67 (s, 1H), 6.65 (d, J=3.5 Hz, 1H), 4.64 (d, J=2.5 Hz, 2H), 3.55 (v br s, 2H), 2.29 (t, J=2.5 Hz, 1H), 1.41 (dd, J=8.3, 5.3 Hz, 2H), 1.21 (dd, J=8.3, 5.3 Hz, 2H).

Intermediate 5: 7-Fluoro-6-hydrazinyl-4-(prop-2-yn-1-yl)spiro[benzo[b][1,4]oxazine-2,1'-cyclopropan]-3(4H)-one

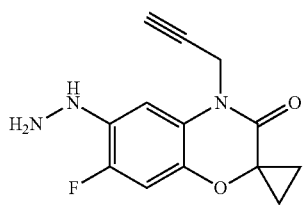 [SMILES: C#CCN1C(=O)C2(CC2)Oc2cc(F)c(NN)cc21]

Intermediate 4 (100 mg, 0.406 mmol) and hydrochloric acid (37% aq. solution, 580 µL) were added to a round-bottomed flask. The flask was cooled to 0° C. by submerging it in an ice bath and sodium nitrite (33.6 mg, 0.487 mmol) was added in a dropwise manner as a solution in water (1.25 mL) and the reaction was allowed to proceed for 1 h at 0° C. The flask was cooled to −35° C. by submerging it in a dry ice/IPA bath and a solution of tin(II) chloride dihydrate (458 mg, 2.03 mmol) in hydrochloric acid (37% aq. solution, 499 µL, 16.2 mmol) was added and the reaction was then allowed to warm to room temperature to proceed for 2 hours with vigorous stirring. The resulting precipitate was filtered, washed with diethyl ether (15 mL) to afford the title compound as a white powder (64 mg, 61% yield). $^1$H NMR $\delta_H$ (500 MHz, DMSO-d$_6$) δ 9.91 (s, 2H), 8.01 (s, 1H), 7.19 (d, J=8.0 Hz, 1H), 7.04 (d, J=11.1 Hz, 1H), 4.64 (d, J=2.3 Hz, 2H), 3.33 (t, J=2.4 Hz, 1H), 1.28 (dd, J=8.3, 5.3 Hz, 2H), 1.24 (dd, J=8.2, 5.3 Hz, 2H).

Intermediate 6: N'-(7-Fluoro-3-oxo-4-(prop-2-yn-1-yl)-3,4-dihydrospiro[benzo[b][1,4]oxazine-2,1'-cyclopropan]-6-yl)pivalohydrazide

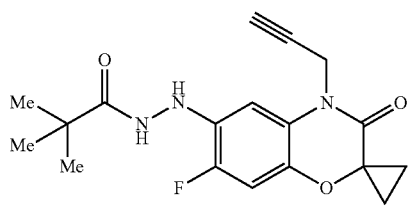 [SMILES: C#CCN1C(=O)C2(CC2)Oc2cc(F)c(NNC(=O)C(C)(C)C)cc21]

Intermediate 5 (106 mg, 0.406 mmol) and DCM (4 mL) were added to a round-bottomed flask. Triethylamine (62 µL, 0.45 mmol) was added before the dropwise addition of trimethylacetic anhydride (86 µL, 0.43 mmol). The reaction was allowed to proceed at room temperature for approx. 16 hours. Water (10 mL) and EtOAc (10 mL) were added to the reaction mixture and the layers separated. The aqueous layer was re-extracted with EtOAc (3×10 mL) and the combined organics were dried using anhydrous Na$_2$SO$_4$ and concentrated under reduced pressure to afford the title compound as a yellow solid (140 mg, >99%). LCMS (Method F): 1.61 min (346.1, MH$^+$).

Intermediate 7: (E)-7-Fluoro-4-(prop-2-yn-1-yl)-6-(2-(3,3,3-trifluoro-2-oxopropylidene)hydrazineyl)spiro[benzo[b][1,4]oxazine-2,1'-cyclopropan]-3(4H)-one

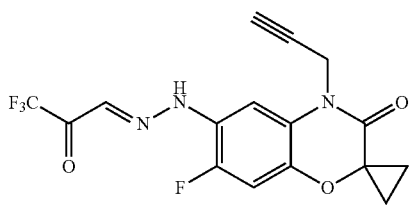 [SMILES: C#CCN1C(=O)C2(CC2)Oc2cc(F)c(N/N=C/C(=O)C(F)(F)F)cc21]

Anhydrous sodium acetate (57 mg, 0.69 mmol) and water (1.3 mL) were added to a microwave reaction vial. The vial was capped and cooled to 0° C. by submerging it in an ice bath. 1,1-Dibromo-3,3,3-trifluoroacetone (0.04 mL, 0.3 mmol) was then added and the reaction was heated to 80° C. for 1 hour. The reaction mixture was then cooled to 0° C. again before the addition of Intermediate 5 (64.8 mg, 0.248 mmol) in one portion and the reaction was then allowed to warm to room temperature to proceed for 2 hours. The reaction mixture was filtered through filter paper and the precipitate was washed with water (15 mL) and heptane (15 mL) and left to dry. This afforded the title compound as a yellow solid (44 mg, 48%). $^1$H NMR $\delta_H$ (500 MHz, DMSO-d$_6$) δ 12.33 (s, 1H), 7.71 (s, 1H), 7.43 (d, J=7.6 Hz, 1H), 7.13

(d, J=11.3 Hz, 1H), 4.66 (d, J=2.3 Hz, 2H), 3.32 (t, J=2.5 Hz, 1H), 1.31 (dd, J=8.3, 5.3 Hz, 2H), 1.26 (dd, J=8.2, 5.3 Hz, 2H).

Intermediate 8: 1-(7-Fluoro-3-oxo-4-(prop-2-yn-1-yl)-3,4-dihydrospiro[benzo[b][1,4]oxazine-2,1'-cyclopropan]-6-yl)-3-propylthiourea

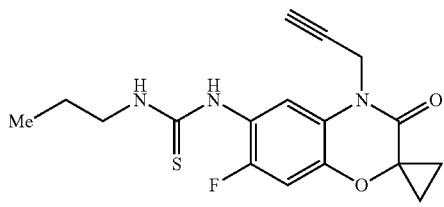 [SMILES: C#CCN1C(=O)C2(CC2)Oc2cc(F)c(NC(=S)NCCC)cc21]

Intermediate 4 (100 mg, 0.406 mmol), sodium hydrogen carbonate (119 mg, 1.42 mmol) and THF (2.0 mL) were added to a round-bottomed flask. The flask was cooled to 0° C. by submerging it in an ice bath and was fitted with a septum and purged with nitrogen. Thiophosgene (0.034 mL, 0.45 mmol) was then added in a dropwise manner, maintaining the internal reaction temperature below 10° C. The reaction was then allowed to warm to room temperature before being allowed to proceed for 2 hours. Propylamine (100 μL, 1.22 mmol) was then added in a dropwise manner and the reaction was allowed to proceed for 2 hours. 1 M aq. HCl (3 mL) was added to the reaction and the layers separated. The aqueous layer was re-extracted with EtOAc (3×10 mL) and the combined organics were dried using anhydrous $Na_2SO_4$ and concentrated under reduced pressure to afford the title compound as a pale yellow solid (131 mg, 93%). $^1$H NMR $\delta_H$ (500 MHz, DMSO-$d_6$) δ 9.15 (s, 1H), 7.83 (s, 1H), 7.43 (d, J=6.2 Hz, 1H), 7.00 (d, J=10.2 Hz, 1H), 4.67 (d, J=2.3 Hz, 2H), 3.30 (t, J=2.4 Hz, 1H), 1.60-1.45 (m, 2H), 1.43-1.18 (m, 5H), 0.89-0.80 (m, 4H). LCMS (Method F): 1.70 min (348.2, MH$^+$).

Intermediate 9: 1-Hydroxycyclobutane-1-carbonitrile

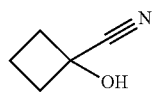

A solution of sodium bisulfite (9.65 g, 93.0 mmol) in water (10 mL) was added dropwise to a solution of cyclobutanone (5.33 mL, 71.3 mmol) and sodium cyanide (4.54 g, 93.0 mmol) in water (25 mL) at 0° C. and the reaction mixture stirred at RT for 90 mins. The aqueous solution was then extracted into ether and the combined organic fractions were then dried ($MgSO_4$) and concentrated in vacuo to give the title compound as a pale yellow oil (5.45 g, 78%). $^1$H NMR $\delta_H$(500 MHz, CDCl$_3$) 2.72-2.62 (m, 2H), 2.41-2.31 (m, 2H), 2.06-1.91 (m, 2H).

Intermediate 10: Benzyl 3-cyano-3-hydroxyazetidine-1-carboxylate

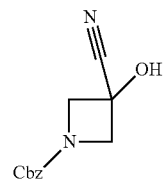 [SMILES: N#CC1(O)CN(C(=O)OCc2ccccc2)C1]

Prepared according to the experimental procedure described for Intermediate 9, using sodium bisulfite (3.30 g, 31.7 mmol) in water (10 mL), benzyl-3-oxoazetidine-1-carboxylate (5.000 g, 24.36 mmol) and sodium cyanide (1.55 g, 31.7 mmol) in water (20 mL) to afford the title compound as a viscous orange oil (4.41 g, 78%). $^1$H NMR $\delta_H$ (500 MHz, DMSO-$d_6$) 7.60 (s, 1H), 7.44-7.27 (m, 5H), 5.07 (s, 2H), 4.41 (d, J=6.9 Hz, 2H), 4.00 (d, J=6.9 Hz, 2H).

Intermediate 11: 1-(5-Fluoro-2,4-dinitrophenoxy)cyclobutane-1-carbonitrile

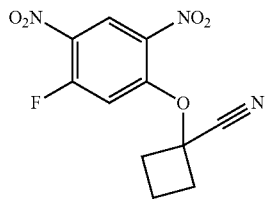 [SMILES: N#CC1(Oc2cc(F)c([N+](=O)[O-])cc2[N+](=O)[O-])CCC1]

Triethylamine (3.44 mL, 24.7 mmol) was added to a solution of 1,5-difluoro-2,4-dinitrobenzene (5.04 g, 24.7 mmol) and Intermediate 9 (2.00 g, 20.6 mmol) in DCM (25 mL) at RT and the reaction mixture stirred for 18 h. The reaction was then concentrated in vacuo and the residue purified by flash chromatography (SiO$_2$, 0-66% EtOAc in PE) to give the title compound as an orange solid (4.53 g, 78%). $^1$H NMR $\delta_H$ (500 MHz, DMSO-$d_6$) 8.92 (d, J=7.8 Hz, 1H), 7.56 (d, J=12.0 Hz, 1H), 3.17-3.02 (m, 2H), 2.72-2.61 (m, 2H), 2.12-2.00 (m, 2H).

Intermediates 12-13

The following intermediates were prepared using the general method described for Intermediate 11, from the appropriate intermediate:

| Intermediate No. | Compound | ¹H NMR/LCMS |
|---|---|---|
| 12 From Intermediate 10 | Benzyl 3-cyano-3-(5-fluoro-2,4-dinitrophenoxy)azetidine-1-carboxylate | (500 MHz, CDCl₃): δ 8.90 (d, J = 7.6 Hz, 1H), 7.43-7.34 (m, 5H), 6.88 (d, J = 10.6 Hz, 1H), 5.16 (s, 2H), 4.75 (dd, J = 10.3, 1.0 Hz, 2H), 4.50 (dd, J = 10.4, 0.7 Hz, 2H). |
| 13 | Methyl 1-(5-fluoro-2,4-dinitrophenoxy)cyclopropane-1-carboxylate | (500 MHz, DMSO-d₆): δ 8.80 (d, J = 7.7 Hz, 1H), 7.04 (d, J = 11.7 Hz, 1H), 3.83 (s, 3H), 1.88-1.78 (m, 2H), 1.56-1.46 (m, 2H). |

Intermediate 14: 6-Amino-7-fluorospiro[benzo[b][1,4]oxazine-2,1'-cyclopropan]-3(4H)-one

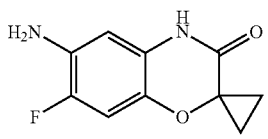 [SMILES: Nc1cc2c(cc1F)OC1(CC1)C(=O)N2]

To a 50 mL round-bottomed flask was added palladium on activated charcoal (89 mg, 0.083 mmol) and Intermediate 13 (500 mg, 1.67 mmol). The flask was sealed with a rubber septum and purged with nitrogen before ethanol (11 mL) and dioxane (11 mL) were added. The flask was evacuated, fitted with a hydrogen balloon, filling the reaction vessel with hydrogen, and the reaction was then allowed to proceed at RT for approx. 22 h. The reaction mixture was filtered through Celite®, washing with EtOAc (100 mL) to give a filtrate which was dried using anhydrous Na₂SO₄ and concentrated under reduced pressure to afford the title compound as a brown solid (635 mg, 91%). ¹H NMR δ_H (500 MHz, DMSO-d₆) 10.56 (s, 1H), 6.64 (d, J=11.4 Hz, 1H), 6.37 (d, J=8.9 Hz, 1H), 4.76 (s, 2H), 1.22-1.07 (m, 4H).

Intermediate 15: 6-Amino-7-fluorospiro[benzo[b][1,4]oxazine-2,1'-cyclobutan]-3(4H)-one

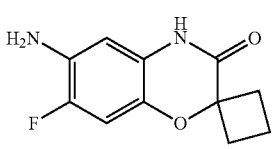 [SMILES: Nc1cc2c(cc1F)OC1(CCC1)C(=O)N2]

Hydrochloric acid (37% aq., 19.92 mL, 645.0 mmol) was slowly added to a solution of Intermediate 11 (4.53 g, 16.1 mmol) and iron powder (5.40 g, 97.0 mmol) in THF (40 mL), methanol (20 mL) and water (10 mL) and stirred at 70° C. for 18 h. The reaction mixture was then neutralised with NaOH (1 M) and filtered through a pad of Celite®. The filter cake was then washed with 10% MeOH:EtOAc before being concentrated in vacuo. The residue was purified by chromatography (SiO₂, 0-66% EtOAc in PE) to give the title compound as a grey solid (0.621 g, 17%). ¹H NMR δ_H (500 MHz, DMSO-d₆) 10.40 (s, 1H), 6.76 (d, J=11.4 Hz, 1H), 6.33 (d, J=8.9 Hz, 1H), 4.88 (s, 2H), 2.46-2.38 (m, 2H), 2.15 (ddd, J=13.2, 10.3, 5.2 Hz, 2H), 1.88 (dd, J=10.3, 4.8 Hz, 1H), 1.80-1.72 (m, 1H).

Intermediate 16: Benzyl 6'-amino-7'-fluoro-3'-oxo-3,4'-dihydrospiro[azetidine-3,2'-benzo[b][1,4]oxazine]-1-carboxylate

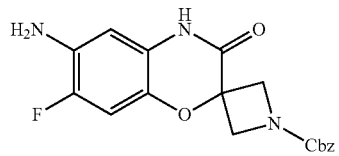 [SMILES: Nc1cc2c(cc1F)OC1(CN(C(=O)OCc3ccccc3)C1)C(=O)N2]

Prepared according to the experimental procedure described for Intermediate 15, using hydrochloric acid (37% aq., 6.88 mL, 223 mmol), Intermediate 12 (2.32 g, 5.57 mmol), iron powder (1.87 g, 33.4 mmol), THF (40 mL), MeOH (20 mL) and water (10 mL). The crude residue was purified by chromatography (SiO₂, 0-66% PE:EtOAc) to give the title compound as a grey solid (0.711 g, 36%). ¹H NMR δ_H (500 MHz, DMSO-d₆) 10.80 (s, 1H), 7.45-7.24 (m, 5H), 6.87 (d, J=11.3 Hz, 1H), 6.36 (d, J=8.8 Hz, 1H), 5.08 (s, 2H), 5.00 (s, 2H), 4.35 (d, J=18.3 Hz, 2H), 4.03 (dd, J=14.2, 7.1 Hz, 2H).

Intermediate 17: 6-Amino-7-fluoro-4-(prop-2-yn-1-yl)spiro[benzo[b][1,4]oxazine-2,1'-cyclobutan]-3(1H)-one

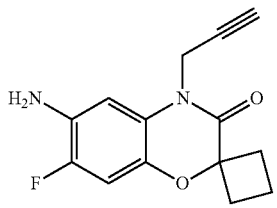 [SMILES: C#CCN1C(=O)C2(CCC2)Oc2cc(F)c(N)cc21]

A solution of Intermediate 11 (295 mg, 1.33 mmol) in DMF (4.5 mL) was added dropwise to a suspension of sodium hydride (60% dispersion in mineral oil, 53 mg, 1.3 mmol) in DMF (2 mL) at RT and stirred for 30 mins. Propargyl bromide (0.126 mL, 1.33 mmol, 80% solution in PhMe) was then added dropwise and the reaction mixture stirred for 18 h. The reaction was then quenched with water and extracted into EtOAc before being dried (MgSO$_4$) and concentrated in vacuo to give the title compound (0.338 g, 99%). $^1$H NMR $\delta_H$ (500 MHz, CDCl$_3$) 6.61 (d, J=10.6 Hz, 1H), 6.51 (d, J=8.2 Hz, 1H), 4.47 (d, J=2.2 Hz, 2H), 2.49-2.35 (m, 2H), 2.16-2.04 (m, 3H), 1.79 (tdd, J=11.2, 9.8, 4.4 Hz, 2H). LCMS (method B): 2.62 mins (261.3, MH$^+$).

Intermediates 18-22

The following intermediates were prepared using the general method described for Intermediate 17, from the appropriate intermediate and alkyl halide:

| Intermediate No. | Compound | $^1$H NMR/LCMS |
|---|---|---|
| 18 | Benzyl 6'-amino-7'-fluoro-3'-oxo-4'-(prop-2-yn-1-yl)-3',4'-dihydrospiro[azetidine-3,2'-benzo[b][1,4]oxazine]-1-carboxylate | (500 MHz, DMSO-d$_6$): δ 7.41-7.27 (m, 5H), 6.97 (d, J = 11.1 Hz, 1H), 6.69 (d, J = 8.5 Hz, 1H), 5.13 (s, 2H), 5.08 (s, 2H), 4.63 (d, J = 2.4 Hz, 2H), 4.33 (d, J = 5.8 Hz, 2H), 4.03 (d, J = 7.1 Hz, 2H), 3.39-3.31 (m, 1H). |
| 19 | 6-Amino-4-(cyclobutylmethyl)-7-fluorospiro[benzo[b][1,4]oxazine-2,1'-cyclopropan]-3(4H)-one | (500 MHz, DMSO-d$_6$): δ 6.69 (d, J = 11.1 Hz, 1H), 6.64 (d, J = 8.7 Hz, 1H), 4.92 (s, 2H), 3.89 (d, J = 7.3 Hz, 2H), 2.64 (m, 1H), 1.94 (m, 2H), 1.84-1.78 (m, 2H), 1.74 (m, 2H), 1.17 (m, 2H), 1.11 (m, 2H). |
| 20 | 6-Amino-7-fluoro-4-propylspiro[benzo[b][1,4]oxazine-2,1'-cyclopropan]-3(4H)-one | (500 MHz, DMSO-d$_6$): δ 6.72 (d, J = 11.1 Hz, 1H), 6.67 (d, J = 8.5 Hz, 1H), 5.09 (s, 2H), 3.78-3.72 (m, 2H), 1.63-1.54 (m, 2H), 1.20-1.15 (m, 2H), 1.14-1.09 (m, 2H), 0.89 (t, J = 7.4 Hz, 3H). |

| Intermediate No. | Compound | ¹H NMR/LCMS |
|---|---|---|
| 21 | Methyl 2-(6-amino-7-fluoro-3-oxospiro[benzo[b][1,4]oxazine-2,1'-cyclopropan]-4(3H)-yl)propanoate | (500 MHz, DMSO-$d_6$): δ 6.76 (d, J = 11.1 Hz, 1H), 6.56 (d, J = 8.5 Hz, 1H), 5.02 (q, J = 6.9 Hz, 1H), 4.95 (s, 2H), 3.63 (s, 23H), 1.49 (d, J = 7.0 Hz, 3H), 1.26-1.22 (m, 1H), 1.20-1.16 (m, 1H), 1.14-1.10 (m, 1H), 1.07 (m, 1H). |
| 22 | Ethyl 2-(6-amino-7-fluoro-3-oxospiro[benzo[b][1,4]oxazine-2,1'-cyclopropan]-4(3H)-yl)propanoate | (500 MHz, DMSO-$d_6$): δ 6.76 (d, J = 11.1 Hz, 1H), 6.57 (d, J = 8.5 Hz, 1H), 4.99 (q, J = 6.9 Hz, 1H), 4.94 (s, 2H), 4.16-4.02 (m, 2H), 1.49 (d, J = 7.0 Hz, 3H), 1.25-1.06 (m, 7H). |

Intermediate 23: 2-(Dimethylamino)-4-(trifluoromethyl)-6H-1,3-oxazin-6-one

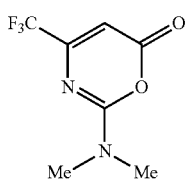

Phosgene dimethyliminium chloride (4.97 g, 30.6 mmol) was added to a solution of 3-amino-4,4,4-trifluorocrotonate (4.00 g, 21.8 mmol) in CHCl₃ (14.5 mL) and the reaction mixture stirred at 60° C. for 18 h. The reaction mixture was then diluted with DCM (20 mL) and washed with HCl (1 M). The organic phase was then dried (MgSO₄) and concentrated in vacuo to give the title compound as a yellow powder (3.608 g, 64%). ¹H NMR $δ_H$ (500 MHz, CDCl₃) 5.88 (s, 1H), 3.25 (s, 3H), 3.20 (s, 3H).

Intermediate 24: 4-((7-Fluoro-3-oxo-4-(prop-2-yn-1-yl)-3,4-dihydrospiro[benzo[b][1,4]oxazine-2,1'-cyclopropan]-6-yl)amino)-4-oxobutanoic acid

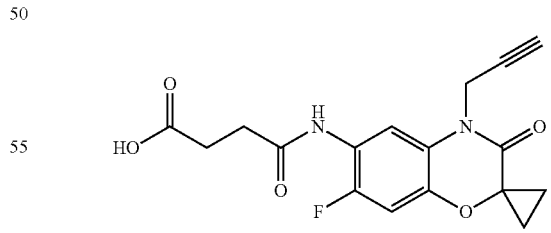

Intermediate 4 (30 mg, 0.12 mmol), dihydrofuran-2,5-dione (14.6 mg, 0.146 mmol), and acetic acid (1.6 mL) were added to a 10 mL round-bottomed flask. The reaction was heated at 80° C. for 6 h. The reaction was allowed to cool to RT and water (20 mL) and EtOAc (20 mL) were added to the reaction mixture and the layers separated. The aqueous layer was extracted with EtOAc (3×20 mL) and the combined organics were dried over MgSO₄ and concentrated under reduced pressure to afford the title compound as an orange/brown solid containing EtOAc (47.6 mg, 113% (by mass; product not pure)). $^1$H NMR $\delta_H$ (500 MHz, DMSO-$d_6$) 12.11 (s, 1H), 9.78 (s, 1H), 7.77 (d, J=7.4 Hz, 1H), 7.01 (d, J=10.7 Hz, 1H), 4.64 (d, J=2.6 Hz, 2H), 3.32 (t, J=2.5 Hz, 1H), b 2.66-2.61 (m, 2H), 1.35-1.22 (m, 6H).

Intermediate 25: 5-((7-Fluoro-3-oxo-4-(prop-2-yn-1-yl)-3,4-dihydrospiro[benzo[b][1,4]oxazine-2,1'-cyclopropan]-6-yl)amino)-3-methyl-5-oxopentanoic acid

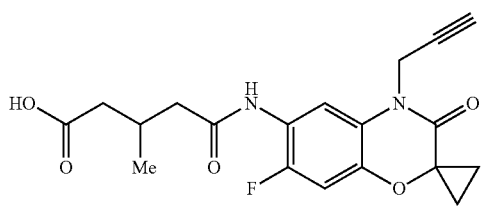 [SMILES: C#CCN1C(=O)C2(CC2)Oc2cc(F)c(NC(=O)CC(C)CC(=O)O)cc21]

Prepared according to the experimental procedure used for Intermediate 24, using Intermediate 4 (30 mg, 0.12 mmol), methylglutaric anhydride (18.7 mg, 0.146 mmol), and acetic acid (1.6 mL) to afford the title compound as an orange/brown tar containing EtOAc (62 mg). $^1$H NMR $\delta_H$ (500 MHz, DMSO-$d_6$) 12.08 (s, 1H), 9.72 (s, 1H), 7.66 (d, J=7.4 Hz, 1H), 7.00 (d, J=10.5 Hz, 1H), 4.67 (d, J=2.2 Hz, 2H), 3.31 (t, J=2.5 Hz, 1H), δ 2.40-2.25 (m, 4H), 2.10 (m, 1H), 1.28 (dd, J=3.9, 2.2 Hz, 2H), 1.25 (dd, J=3.8, 2.1 Hz, 2H), 0.96 (d, J=5.9 Hz, 3H).

Intermediate 26: 5-Fluoro-2-(7-fluoro-3-oxo-3,4-dihydrospiro[benzo[b][1,4]oxazine-2,1'-cyclopropan]-6-yl)isoindoline-1,3-dione

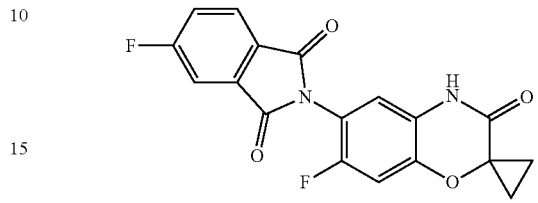

Prepared according to the experimental procedure used for Example 1, using 4-fluorophthalic anhydride (144 mg, 0.865 mmol), Intermediate 14 (150 mg, 0.721 mmol) and acetic acid (7.2 mL) to afford the title compound as a brown solid (237.8 mg, 93%). $^1$H NMR $\delta_H$ (500 MHz, DMSO-$d_6$) 11.06 (s, 1H), 8.07 (dd, J=8.3, 4.5 Hz, 1H), 7.92 (dd, J=7.5, 2.2 Hz, 1H), 7.78-7.73 (m, 1H), 7.12 (d, J=10.2 Hz, 1H), 7.09 (d, J=7.2 Hz, 1H), 1.30 (dd, J=6.5, 2.7 Hz, 2H), 1.26 (dd, J=6.4, 2.8 Hz, 2H).

Intermediates 27-30

The following intermediates were prepared using the general method described for Intermediate 17, from the appropriate intermediate and alkyl halide:

| Intermediate No. | Compound | $^1$H NMR/LCMS |
|---|---|---|
| 27 | 6-Amino-4-(cyclopropylmethyl)-7-fluorospiro[benzo[b][1,4]oxazine-2,1'-cyclopropan]-3(4H)-one | (500 MHz, DMSO-$d_6$): δ 6.76 (d, J = 8.7 Hz, 1H), 6.71 (d, J = 11.1 Hz, 1H), 4.94 (s, 2H), 3.72 (d, J = 6.9 Hz, 2H), 1.24-1.05 (m, 5H), 0.54-0.42 (m, 2H), 0.41-0.29 (m, 2H). LCMS (Method F): 1.63 min (263.1, [MH]$^+$). |
| 28 | 2-(6-Amino-7-fluoro-3-oxospiro[benzo[b][1,4]oxazine-2,1'-cyclopropan]-4(3H)-yl)acetonitrile | (500 MHz, DMSO-$d_6$): δ 6.81 (d, J = 11.1 Hz, 1H), 6.68 (d, J = 8.4 Hz, 1H), 5.11 (s, 2H), 4.97 (s, 2H), 1.27-1.23 (m, 4H). LCMS (Method F): 1.44 min (246.1, [MH]$^-$). |

-continued

| Intermediate No. | Compound | ¹H NMR/LCMS |
|---|---|---|
| 29 | 6-Amino-7-fluoro-4-(3-methylbut-2-en-1-yl)spiro[benzo[b][1,4]oxazine-2,1'-cyclopropan]-3(4H)-one 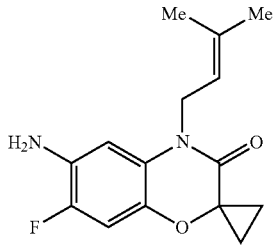 | LCMS (Method F): 1.83 min (277.1, [MH]⁺). |
| 30 | 6-Amino-7-fluoro-4-(oxiran-2-ylmethyl)spiro[benzo[b][1,4]oxazine-2,1'-cyclopropan]-3(4H)-one 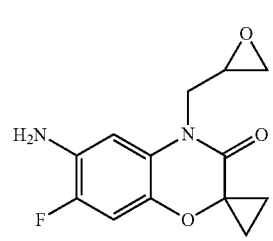 | (500 MHz, DMSO-d₆): δ 6.74 (d, J = 1.9 Hz, 1H), 6.72 (d, J = 4.4 Hz, 1H), 4.94 (s, 2H), 4.16 (dd, J = 15.2, 3.6 Hz, 1H), 3.81 (dd, J = 15.2, 5.3 Hz, 1H), 3.18-3.15 (m, 1H), 2.79 (dd, J = 4.9, 4.1 Hz, 1H), 2.63 (dd, J = 5.0, 2.6 Hz, 1H), 1.20-1.12 (m, 4H). LCMS (Method F): 1.36 min (265.0, [MH]⁺). |

Intermediate 31: 2-(6-Amino-7-fluoro-3-oxospiro[benzo[b][1,4]oxazine-2,1'-cyclopropan]-4(3H)-yl)propanoic acid

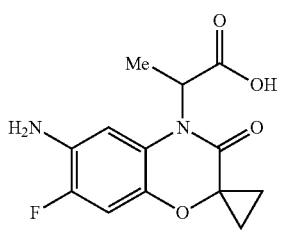 [SMILES: CC(C(=O)O)N1C(=O)C2(CC2)Oc2cc(F)c(N)cc21]

Methanol (1.6 mL) was added to Intermediate 21 (147 mg, 0.500 mmol) and sodium hydroxide (100 mg, 2.50 mmol) and the resulting mixture was stirred at RT for 20 h. Water (30 mL), sat. brine (2 mL), 1 M aq. HCl (2 mL) and EtOAc (20 mL) were added and the layers separated. The aqueous layer was extracted with EtOAc (3×10 mL) and the combined organics were dried over MgSO₄ and concentrated in vacuo to afford the title compound as a pale orange solid (102 mg, 73%). 1H NMR δ_H (500 MHz, DMSO-d₆) 12.82 (s, 1H), 6.74 (d, J=11.1 Hz, 1H), 6.56 (d, J=8.6 Hz, 1H), 5.00-4.90 (m, 3H), 1.47 (d, J=7.0 Hz, 3H), 1.26-1.05 (m, 4H). LCMS (Method F): 1.34 min (281.0, MH⁺).

Intermediate 32: 4-(Cyclopropylmethyl)-7-fluoro-6-iodospiro[benzo[b][1,4]oxazine-2,1'-cyclopropan]-3(4H)-one

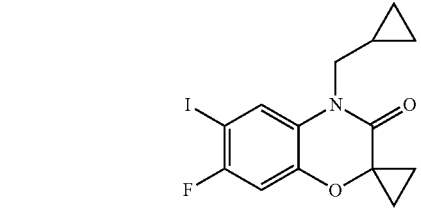 [SMILES: O=C1N(CC2CC2)c2cc(I)c(F)cc2OC12CC2]

Intermediate 27 (500 mg, 1.91 mmol), aq. HCl (37% solution, 1.5 mL) and MeCN (8 mL) were added to a 25 mL round-bottomed flask. The flask was cooled to 0° C. and tert-butyl nitrite (230 μL, 1.91 mmol) was added in a dropwise manner and the reaction was allowed to proceed for 1 h at 0° C. Potassium iodide (633 mg, 3.81 mmol) was then added dropwise as a solution in water (5 mL) before the addition of MeCN (5 mL) and the reaction was allowed to warm to RT for 2 h. The reaction mixture was added to 20% aq. Na₂S₂O₃ (100 mL) and EtOAc (50 mL), the aqueous layer was extracted with EtOAc (3×50 mL) and the combined organics were dried (MgSO₄) and concentrated in vacuo. The crude residue was dissolved in EtOAc (10 mL) and a white precipitate formed. The precipitate was filtered off and discarded and the filtrate was again concentrated in vacuo to afford an off-white solid (644 mg, 91%). ¹H NMR $\delta_H$ (500 MHz, DMSO-d$_6$): δ 7.68 (d, J=6.1 Hz, 1H), 7.00 (d, J=8.2 Hz, 1H), 3.87 (d, J=6.9 Hz, 2H), 1.32-1.15 (m, 4H), 1.14-1.00 (m, 1H), 0.52-0.38 (m, 2H), 0.37-0.24 (m, 2H). LCMS (Method F): 2.27 min (374.0, MH$^+$).

Intermediates 33-34

The following intermediates were prepared using the general method described in Example 32 from the appropriate Intermediate and Intermediate 23:

mmol) in acetic acid (2.0 mL, 35 mmol). The reaction mixture was heated to 120° C. for 2 h, then cooled to RT and diluted with water. The aqueous solution was extracted with EtOAc (×3). The combined EtOAc layers were washed (aq. NaHCO$_3$), dried (MgSO$_4$) and concentrated in vacuo. The residue was purified by chromatography (SiO$_2$, 0-25% EtOAc in PE) and the title compound was isolated as a yellow solid (63 mg, 82%). $^1$H NMR $\delta_H$ (500 MHz, CDCl$_3$) 7.04 (d, J=6.8 Hz, 1H), 6.81 (d, J=9.6 Hz, 1H), 4.68 (d, J=2.5 Hz, 2H), 2.51-2.44 (m, 4H), 2.31 (t, J=2.5 Hz, 1H), 1.90-

| Intermediate No. | Compound | $^1$H NMR/LCMS |
|---|---|---|
| 33 | 3-(4-(Cyclopropylmethyl)-7-fluoro-3-oxo-3,4-dihydrospiro[benzo[b][1,4]oxazine-2,1'-cyclopropan]-6-yl)-6-(trifluoromethyl)pyrimidine-2,4-(1H,3H)-dione | (500 MHz, CDCl$_3$) 6.93 (d, J = 6.8 Hz, 1H), 6.79 (d, J = 9.6 Hz, 1H), 6.67 (d, J = 10.8 Hz, 1H), 6.23 (s, 1H), 3.86-3.76 (m, 2H), 1.39 (ddd, J = 20.7, 8.0, 4.7 Hz, 5H), 1.32-1.20 (m, 2H), 1.17 (d, J = 5.1 Hz, 2H). LCMS (Method C): 3.10 min, (426.1 MH$^+$). |
| 34 | Methyl 2-(6-(2,6-dioxo-4-(trifluoromethyl)-3,6-dihydropyrimidin-1(2H)-yl)-7-fluoro-3-oxospiro[benzo[b][1,4]oxazine-2,1'-cyclopropan]-4(3H)-yl)propanoate | (500 MHz, CDCl$_3$) δ 6.84 (d, J = 9.5 Hz, 1H), 6.66 (t, J = 6.4 Hz, 1H), 6.26 (d, J = 4.4 Hz, 1H), 5.30-5.26 (m, 1H), 3.72 (d, J = 3.6 Hz, 3H), 1.61 (dd, J = 7.2, 1.8 Hz, 3H), 1.32-1.20 (m, 4H). LCMS (Method C): 2.89 min, (458.1 MH$^+$). |

Example 1: 2-(7-Fluoro-3-oxo-4-(prop-2-yn-1-yl)-3,4-dihydrospiro[benzo[b][1,4]oxazine-2,1'-cyclopropan]-6-yl)-4,5,6,7-tetrahydro-1H-isoindole-1,3(2H)-dione

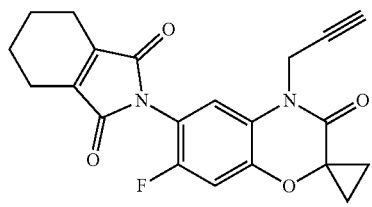 [SMILES: C#CCN1C(=O)C2(CC2)Oc2cc(F)c(N3C(=O)C4=C(CCCC4)C3=O)cc21]

3,4,5,6-Tetrahydrophthalic anhydride (37 mg, 0.24 mmol) was added to a solution of Intermediate 4 (50 mg, 0.20

1.82 (m, 4H), 1.49 (dd, J=8.5, 5.4 Hz, 2H), 1.28 (dd, J=8.4, 5.4 Hz, 2H). LCMS (Method A): 3.29 min (381.1, MH$^+$).

Example 2: 1-(7-Fluoro-3-oxo-4-(prop-2-yn-1-yl)-3,4-dihydrospiro[benzo[b][1,4]oxazine-2,1'-cyclopropan]-6-yl)-3-propyl-2-thioxoimidazolidine-4,5-dione

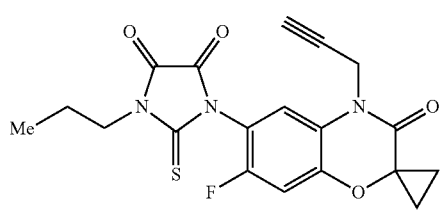 [SMILES: C#CCN1C(=O)C2(CC2)Oc2cc(F)c(N3C(=O)C(=O)N(CCC)C3=S)cc21]

Intermediate 8 (50 mg, 0.14 mmol) was added to a flask containing triethylamine (44 μL, 0.32 mmol) and THF (2.5 mL). The flask was fitted with a rubber septum and purged with nitrogen before the dropwise addition of oxalyl chloride (13.4 μL, 0.158 mmol). The reaction was allowed to proceed at room temperature for approx. 20 hours. Water (10 mL) and EtOAc (10 mL) were added to the reaction mixture and the layers separated. The aqueous layer was re-extracted with EtOAc (3×10 mL) and the combined organics were dried using anhydrous $Na_2SO_4$ and concentrated under reduced pressure to afford a yellow solid. The crude product was purified by chromatography ($SiO_2$, 0-20% EtOAc in PE) to afford the title compound as a yellow solid (42 mg, 73%). $^1$H NMR $\delta_H$ (500 MHz, DMSO-$d_6$) 7.38 (d, J=6.8 Hz, 1H), 7.22 (d, J=9.9 Hz, 1H), 4.65-4.55 (m, 2H), 3.85 (td, J=7.0, 1.9 Hz, 2H), 3.36 (t, J=2.4 Hz, 1H), 1.74-1.65 (m, 2H), 1.39-1.30 (m, 4H), 0.94 (t, J=7.4 Hz, 3H). LCMS (Method F): 2.06 min (402.2, MH$^+$).

Example 3: 6-(5-(tert-Butyl)-2-oxo-1,3,4-oxadiazol-3(2H)-yl)-7-fluoro-4-(prop-2-yn-1-yl)spiro[benzo[b][1,4]oxazine-2,1'-cyclopropan]-3(4H)-one

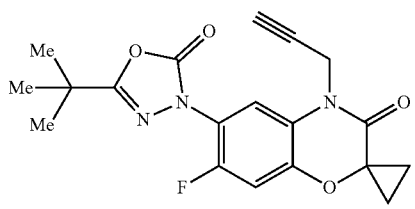 [SMILES: C#CCN1C(=O)C2(CC2)Oc2cc(F)c(-n3nc(C(C)(C)C)oc3=O)cc21]

Intermediate 6 (140 mg, 0.405 mmol) and anhydrous toluene (4 mL) were added to a microwave reaction vial. The vial was capped, purged with nitrogen and triphosgene (120 mg, 0.405 mmol) was added dropwise as a solution in anhydrous toluene (0.5 mL). The reaction was then heated to 110° C. for 4 hours. The reaction was allowed to cool to room temperature, water (10 mL) and sat. brine (3 mL) were added to the reaction mixture and the layers separated. The aqueous layer was re-extracted with EtOAc (3×10 mL) and the combined organics were dried using anhydrous $MgSO_4$ and concentrated under reduced pressure to afford a pale yellow solid. The crude residue was passed through a short pad of silica, eluting with 50% EtOAc in PE (10 mL) to afford the title compound as a yellow solid (59 mg, 39%). $^1$H NMR $\delta_H$ (500 MHz, DMSO-$d_6$) 7.54 (d, J=7.1 Hz, 1H), 7.22 (d, J=10.3 Hz, 1H), 4.71 (d, J=2.3 Hz, 2H), 2.30 (s, 1H), 1.39-1.21 (m, 13H). LCMS (Method F): 2.01 min (372.1, MH$^+$).

Example 4: 7-Fluoro-6-(5-methyl-6-oxo-4-(trifluoromethyl)pyridazin-1(6H)-yl)-4-(prop-2-yn-1-yl)spiro[benzo[b][1,4]oxazine-2,1'-cyclopropan]-3(4H)-one

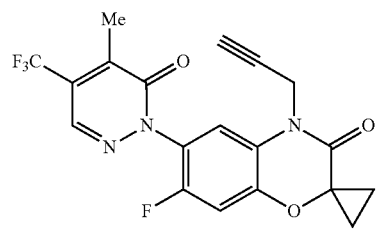 [SMILES: C#CCN1C(=O)C2(CC2)Oc2cc(F)c(-n3ncc(C(F)(F)F)c(C)c3=O)cc21]

Intermediate 7 (44 mg, 0.12 mmol), (carbethoxyethylidene)triphenylphosphorane (64.8 mg, 0.179 mmol), anhydrous toluene (1.2 mL) and powdered molecular sieves (50 mg) were added to a microwave reaction vial. The vial was capped, purged with nitrogen and the reaction was then heated to 110° C. for approx. 16 hours. The reaction mixture was filtered, washing with EtOAc (10 mL) to afford a filtrate which was concentrated under reduced pressure to afford a yellow solid. The crude residue was purified by chromatography ($SiO_2$, 0-25% EtOAc in PE) to afford the title compound as a yellow solid (28 mg, 58%). $^1$H NMR $\delta_H$ (500 MHz, DMSO-$d_6$) 8.33 (s, 1H), 7.47 (d, J=6.9 Hz, 1H), 7.22 (d, J=10.1 Hz, 1H), 4.70 (s, 2H), 3.32-3.30 (m, 1H), 2.32 (s, 3H), 1.36-1.33 (m, 4H). LCMS (Method F): 1.95 min (408.1, MH$^+$).

Example 5

The following examples were prepared using the general method described in Example 1 from Intermediate 4 and the appropriate anhydride derivative.

| Example No. | Compound | $^1$H NMR/LCMS |
|---|---|---|
| 5 | 5-Fluoro-2-(7-fluoro-3-oxo-4-(prop-2-yn-1-yl)-3,4-dihydrospiro[benzo[b][1,4]oxazine-2,1'-cyclopropan]-6-yl)isoindoline-1,3-dione | (500 MHz, CDCl$_3$): δ 7.99 (dd, J = 8.2, 4.4 Hz, 1H), 7.65 (dd, J = 6.9, 2.2 Hz, 1H), 7.49 (td, J = 8.5, 2.1 Hz, 1H), 7.11 (d, J = 6.7 Hz, 1H), 6.85 (d, J = 9.6 Hz, 1H), 4.68 (d, J = 2.3 Hz, 2H), 2.29 (d, J = 2.3 Hz, 1H), 1.50-1.47 (m, 2H), 1.27 (dd, J = 9.9, 4.3 Hz, 2H). LCMS (Method F): 1.92 min (395.1, [MH]$^+$). |

Examples 6-26

The following examples were prepared using the general method described for Example 1, from the appropriate intermediate and anhydride derivative:

| Example No. | Compound | ¹H NMR/LCMS |
|---|---|---|
| 6 | 4-Fluoro-2-(7-fluoro-3-oxo-4-(prop-2-yn-1-yl)-3,4-dihydrospiro[benzo[b][1,4]oxazine-2,1'-cyclopropan]-6-yl)isoindoline-1,3-dione | (500 MHz, CDCl$_3$): δ 7.83 (m, 2H), 7.51-7.46 (m, 1H), 7.11 (d, J = 6.7 Hz, 1H), 6.85 (d, J = 9.6 Hz, 1H), 4.67 (d, J = 2.4 Hz, 2H), 2.29 (t, J = 2.4 Hz, 1H), 1.49 (dd, J = 8.4, 5.4 Hz, 2H), 1.28 (dd, J = 8.3, 5.4 Hz, 2H). LCMS (Method F): 1.88 min (395.1, MH$^+$). |
| 7 | 2-(7-Fluoro-3-oxo-4-(prop-2-yn-1-yl)-3,4-dihydrospiro[benzo[b][1,4]oxazine-2,1'-cyclopropan]-6-yl)isoindoline-1,3-dione | (500 MHz, DMSO-d$_6$): δ 8.03 (dd, J = 5.5, 3.0 Hz, 2H), 7.96 (dd, J = 5.5, 3.1 Hz, 2H), 7.53 (d, J = 7.0 Hz, 1H), 7.23 (d, J = 9.9 Hz, 1H), 4.65 (d, J = 2.4 Hz, 2H), 3.31 (t, J = 2.4 Hz, 1H), 1.42-1.29 (m, 4H). LCMS (Method F): 1.90 min (377.1, MH+). |
| 8 | 2-(7-Fluoro-3-oxo-4-(prop-2-yn-1-yl)-3,4-dihydrospiro[benzo[b][1,4]oxazine-2,1'-cyclopropan]-6-yl)-5-methylisoindoline-1,3-dione | (500 MHz, CDCl$_3$): δ 7.86 (d, J = 7.7 Hz, 1H), 7.78 (s, 1H), 7.61 (d, J = 7.7 Hz, 1H), 7.12 (d, J = 6.7 Hz, 1H), 6.84 (d, J = 9.6 Hz, 1H), 4.67 (d, J = 2.5 Hz, 2H), 2.56 (s, 3H), 2.28 (t, J = 2.5 Hz, 1H), 1.48 (dd, J = 8.5, 5.4 Hz, 2H), 1.27 (dd, J = 8.4, 5.4 Hz, 2H). LCMS (Method F): 2.04 min (391.1, MH$^+$). |
| 9 | 2-(7-Fluoro-3-oxo-4-(prop-2-yn-1-yl)-3,4-dihydrospiro[benzo[b][1,4]oxazine-2,1'-cyclopropan]-6-yl)-5-hydroxyisoindoline-1,3-dione | (500 MHz, DMSO-d$_6$): δ 11.31 (s, 1H), 7.72 (dd, J = 8.4, 7.2 Hz, 1H), 7.48 (d, J = 7.1 Hz, 1H), 7.41 (d, J = 6.7 Hz, 1H), 7.31 (d, J = 7.9 Hz, 1H), 7.20 (d, J = 9.9 Hz, 1H), 4.66 (d, J = 1.6 Hz, 2H), 3.30 (t, J = 2.4 Hz, 1H), 1.34 (m, 4H). LCMS (Method F): .181 min (393.1, MH$^+$). |

-continued

| Example No. | Compound | ¹H NMR/LCMS |
|---|---|---|
| 10 | 2-(7-Fluoro-3-oxo-4-(prop-2-yn-1-yl)-3,4-dihydrospiro[benzo[b][1,4]oxazine-2,1'-cyclopropan]-6-yl)-5-methoxyisoindoline-1,3-dione | (500 MHz, DMSO-d$_6$): δ 7.94 (d, J = 8.3 Hz, 1H), 7.54 (d, J = 2.3 Hz, 1H), 7.51 (d, J = 7.1 Hz, 1H), 7.43 (dd, J = 8.4, 2.3 Hz, 1H), 7.22 (d, J = 9.9 Hz, 1H), 4.66 (d, J = 2.3 Hz, 2H), 3.97 (s, 3H), 3.30 (t, J = 2.4 Hz, 1H), 1.39-1.29 (m, 4H). LCMS (Method F): 1.96 min (407.2, MH$^+$). |
| 11 | 2-(7-Fluoro-3-oxo-4-(prop-2-yn-1-yl)-3,4-dihydrospiro[benzo[b][1,4]oxazine-2,1'-cyclopropan]-6-yl)-3a,4,7,7a-tetrahydro-1H-4,7-methanoisoindole-1,3(2H)-dione | (500 MHz, DMSO-d$_6$): δ 7.30-7.16 (m, 2H), 6.37 (s, 2H), 4.71 (s, 2H), 3.33-3.28 (m, 1H), 3.23 (s, 2H), 2.95 (s, 2H), 1.61-1.41 (m, 2H), 1.36-1.28 (m, 4H). LCMS (Method F): 1.83 min (393.1, MH$^+$). |
| 12 | 1-(7-Fluoro-3-oxo-4-(prop-2-yn-1-yl)-3,4-dihydrospiro[benzo[b][1,4]oxazine-2,1'-cyclopropan]-6-yl)-1H-pyrrole-2,5-dione | (500 MHz, CDCl$_3$): δ 7.03 (d, J = 6.8 Hz, 1H), 6.92 (s, 2H), 6.81 (d, J = 9.6 Hz, 1H), 4.66 (d, J = 2.5 Hz, 2H), 2.29 (t, J = 2.5 Hz, 1H), 1.47 (dd, J = 8.5, 5.4 Hz, 2H), 1.26 (dd, J = 8.4, 5.4 Hz, 2H). LCMS (Method F): 1.70 min (327.0, MH$^+$). |
| 13 | 3-(7-Fluoro-3-oxo-4-(prop-2-yn-1-yl)-3,4-dihydrospiro[benzo[b][1,4]oxazine-2,1'-cyclopropan]-6-yl)-3-azabicyclo[3.1.0]hexane-2,4-dione | (500 MHz, DMSO-d$_6$): δ 7.29 (d, J = 7.1 Hz, 1H), 7.13 (d, J = 10.0 Hz, 1H), 4.66 (d, J = 2.4 Hz, 2H), 3.31 (m, 1H), 2.80 (dd, J = 8.1, 3.6 Hz, 2H), 2.53-2.51 (m, 1H), 1.72 (m, 1H), 1.32 (t, J = 2.5 Hz, 2H), 1.30 (t, J = 2.4 Hz, 2H). LCMS (Method F): 1.62 min (341.2, MH$^+$). |

| Example No. | Compound | $^1$H NMR/LCMS |
|---|---|---|
| 14 | 1-(7-Fluoro-3-oxo-4-(prop-2-yn-1-yl)-3,4-dihydrospiro[benzo[b][1,4]oxazine-2,1'-cyclopropan]-6-yl)-3-(trifluoromethyl)-1H-pyrrole-2,5-dione | (500 MHz, DMSO-$d_6$): δ 7.22 (q, J = 1.7 Hz, 1H), 7.04 (d, J = 6.7 Hz, 1H), 6.83 (d, J = 9.6 Hz, 1H), 4.67 (d, J = 2.5 Hz, 2H), 2.31 (t, J = 2.5 Hz, 1H), 1.49 (dd, J = 8.5, 5.5 Hz, 2H), 1.28 (dd, J = 8.4, 5.4 Hz, 2H). LCMS (Method F): 1.91 min (395.1, MH$^+$). |
| 15 | Methyl 2-(6-(1,3-dioxo-1,3,4,5,6,7-hexahydro-2H-isoindol-2-yl)-7-fluoro-3-oxospiro[benzo[b][1,4]oxazine-2,1'-cyclopropan]-4(3H)-yl)propanoate | (500 MHz, DMSO-$d_6$): δ 7.32 (d, J = 7.0 Hz, 1H), 7.18 (d, J = 9.9 Hz, 1H), 5.05 (q, J = 6.9 Hz, 1H), 3.63 (s, 3H), 2.38-2.32 (m, 4H), 1.74 (m, 4H), 1.48 (d, J = 6.9 Hz, 3H), 1.34-1.20 (m, 4H). LCMS (Method F): 2.01 min (429.2, MH$^+$). |
| 16 | Methyl 2-(7-fluoro-6-(5-fluoro-1,3-dioxoisoindolin-2-yl)-3-oxospiro[benzo[b][1,4]oxazine-2,1'-cyclopropan]-4(3H)-yl)propanoate | (500 MHz, CDCl$_3$): δ 7.98 (dd, J = 8.3, 4.4 Hz, 1H), 7.64 (dd, J = 6.9, 2.2 Hz, 1H), 7.51-7.46 (m, 1H), 6.87 (d, J = 9.6 Hz, 1H), 6.74 (d, J = 6.6 Hz, 1H), 5.30 (q, J = 7.2 Hz, 1H), 3.75 (s, 3H), 1.64 (d, J = 7.2 Hz, 3H), 1.55-1.52 (m, 1H), 1.39-1.22 (m, 3H). LCMS (Method F): 1.98 min (443.2, MH$^+$). |

-continued

| Example No. | Compound | $^1$H NMR/LCMS |
|---|---|---|
| 17 | Methyl 2-(6-(2,5-dioxo-3-(trifluoromethyl)-2,5-dihydro-1H-pyrrol-1-yl)-7-fluoro-3-oxospiro[benzo[b][1,4]oxazine-2,1'-cyclopropan]-4(3H)-yl)propanoate 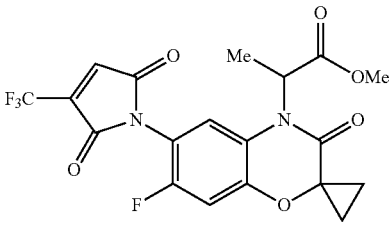 | (500 MHz, CDCl$_3$): δ 7.20 (q, J = 1.6 Hz, 1H), 6.85 (d, J = 9.6 Hz, 1H), 6.66 (d, J = 6.6 Hz, 1H), 5.29 (q, J = 7.1 Hz, 1H), 3.75 (s, 3H), 1.63 (d, J = 7.2 Hz, 3H), 1.55-1.51 (m, 1H), 1.40-1.34 (m, 1H), 1.33-1.21 (m, 2H). LCMS (Method F): 1.97 min (443.2, MH$^+$). |
| 18 | Ethyl 2-(6-(1,3-dioxo-1,3,4,5,6,7-hexahydro-2H-isoindol-2-yl)-7-fluoro-3-oxospiro[benzo[b][1,4]oxazine-2,1'-cyclopropan]-4(3H)-yl)propanoate 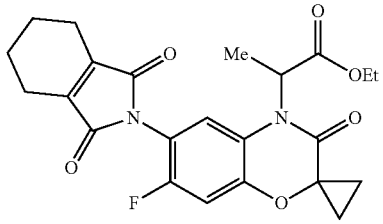 | (500 MHz, CDCl$_3$): δ 6.81 (d, J = 9.6 Hz, 1H), 6.66 (d, J = 6.7 Hz, 1H), 5.23 (q, J = 7.2 Hz, 1H), 4.26-4.14 (m, 2H), 2.46-2.41 (m, 4H), 1.86-1.81 (m, 4H), 1.62 (d, J = 7.2 Hz, 3H), 1.50 (m, 1H), 1.37-1.31 (m, 1H), 1.30-1.21 (m, 2H), 1.19 (t, J = 7.1 Hz, 3H). LCMS (Method F): 2.06 min (443.2, MH$^+$). |
| 19 | Ethyl 2-(7-fluoro-6-(5-fluoro-1,3-dioxoisoindolin-2-yl)-3-oxospiro[benzo[b][1,4]oxazine-2,1'-cyclopropan]-4(3H)-yl)propanoate 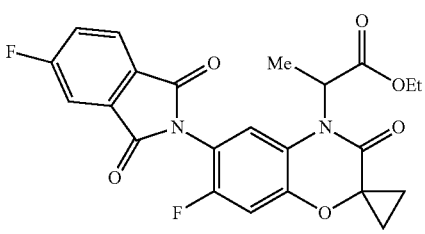 | (500 MHz, CDCl$_3$): δ 7.98 (dd, J = 8.3, 4.5 Hz, 1H), 7.64 (dd, J = 6.9, 2.2 Hz, 1H), 7.51-7.46 (m, 1H), 6.86 (d, J = 9.6 Hz, 1H), 6.76 (d, J = 6.6 Hz, 1H), 5.25 (q, J = 7.2 Hz, 1H), 4.27-4.15 (m, 2H), 1.64 (d, J = 7.2 Hz, 3H), 1.54-1.50 (m, 1H), 1.39-1.34 (m, 1H), 1.33-1.22 (m, 2H), 1.20 (t, J = 7.1 Hz, 3H). LCMS (Method F): 2.06 min (457.2, MH$^+$). |

-continued

| Example No. | Compound | ¹H NMR/LCMS |
|---|---|---|
| 20 | Ethyl 2-(6-(2,5-dioxo-3-(trifluoromethyl)-2,5-dihydro-1H-pyrrol-1-yl)-7-fluoro-3-oxospiro[benzo[b][1,4]oxazine-2,1'-cyclopropan]-4(3H)-yl)propanoate | (500 MHz, CDCl₃): δ 7.20 (q, J = 1.6 Hz, 1H), 6.85 (d, J = 9.6 Hz, 1H), 6.69 (d, J = 6.6 Hz, 1H), 5.26 (q, J = 7.2 Hz, 1H), 4.27-4.14 (m, 2H), 1.63 (d, J = 7.2 Hz, 3H), 1.52 (m, 1H), 1.40-1.34 (m, 1H), 1.33-1.23 (m, 2H), 1.20 (t, J = 7.1 Hz, 3H). LCMS (Method F): 2.02 min (457.1, MH⁺). |
| 21 | 2-(4-(Cyclobutylmethyl)-7-fluoro-3-oxo-3,4-dihydrospiro[benzo[b][1,4]oxazine-2,1'-cyclopropan]-6-yl)-5-fluoroisoindoline-1,3-dione | (500 MHz, CDCl₃): δ 7.99 (dd, J = 8.2, 4.4 Hz, 1H), 7.65 (dd, J = 6.9, 2.1 Hz, 1H), 7.51-7.46 (m, 1H), 6.85 (d, J = 6.8 Hz, 1H), 6.81 (d, J = 9.6 Hz, 1H), 3.98 (d, J = 7.3 Hz, 2H), 2.74-2.66 (m, 1H), 2.02 (m, 2H), 1.90-1.76 (m, 4H), 1.43 (dd, J = 8.4, 5.4 Hz, 2H), 1.23 (dd, J = 8.3, 5.3 Hz, 2H). LCMS (Method D): 9.78 min (425.2, MH⁺). |
| 22 | 5-Fluoro-2-(7-fluoro-3-oxo-4-propyl-3,4-dihydrospiro[benzo[b][1,4]oxazine-2,1'-cyclopropan]-6-yl)isoindoline-1,3-dione | (500 MHz, CDCl₃): δ 7.99 (dd, J = 8.2, 4.4 Hz, 1H), 7.65 (dd, J = 6.9, 2.1 Hz, 1H), 7.51-7.47 (m, 1H), 6.86 (d, J = 6.7 Hz, 1H), 6.82 (d, J = 9.6 Hz, 1H), 3.89-3.83 (m, 2H), 1.70 (m, 2H), 1.44 (dd, J = 8.4, 5.4 Hz, 2H), 1.23 (dd, J = 8.3, 5.3 Hz, 2H), 0.96 (t, J = 7.4 Hz, 3H). LCMS (Method D): 9.26 min (399.2, MH⁺). |
| 23 | 5-Fluoro-2-(7-fluoro-3-oxo-4-(prop-2-yn-1-yl)-3,4-dihydrospiro[benzo[b][1,4]oxazine-2,1'-cyclobutan]-6-yl)isoindoline-1,3-dione | (500 MHz, CDCl₃): δ 8.01 (dd, J = 8.2, 4.4 Hz, 1H), 7.67 (dd, J = 6.9, 2.2 Hz, 1H), 7.51 (td, J = 8.6, 2.3 Hz, 1H), 7.10 (d, J = 6.8 Hz, 1H), 6.99 (d, J = 9.7 Hz, 1H), 4.70 (d, J = 2.5 Hz, 2H), 2.75-2.62 (m, 2H), 2.44-2.32 (m, 2H), 2.30 (t, J = 2.5 Hz, 1H), 2.06-1.97 (m, 2H). LCMS (Method B): 3.57 mins (409.2, MH⁺). |

| Example No. | Compound | ¹H NMR/LCMS |
|---|---|---|
| 24 | 1-(7-Fluoro-3-oxo-4-(prop-2-yn-1-yl)-3,4-dihydrospiro[benzo[b][1,4]oxazine-2,1'-cyclobutan]-6-yl)-3-(trifluoromethyl)-1H-pyrrole-2,5-dione | (500 MHz, CDCl₃): δ 7.24 (q, J = 1.6 Hz, 1H), 7.03 (t, J = 5.8 Hz, 1H), 6.97 (d, J = 9.7 Hz, 1H), 4.68 (d, J = 2.5 Hz, 2H), 2.74-2.60 (m, 2H), 2.44-2.32 (m, 2H), 2.31 (t, J = 2.5 Hz, 1H), 2.05-1.94 (m, 2H). LCMS (Method B): .356 min (409.2, MH⁺). |
| 25 | Benzyl 7'-fluoro-6'-(5-fluroo-1,3-dioxoisoindolin-2-yl)-3'-oxo-4'-(prop-2-yn-1-yl)-3',4'-dihydrospiro[azetidine-3,2'-benzo[b][1,4]oxazine]-1-carboxylate | (500 MHz, CDCl₃): δ 7.96-7.88 (m, 1H), 7.58 (dd, J = 6.9, 2.2 Hz, 1H), 7.43 (td, J = 8.6, 2.3 Hz, 1H), 7.34-7.24 (m, 5H), 7.07 (d, J = 6.6 Hz, 1H), 6.98 (d, J = 9.4 Hz, 1H), 5.07 (s, 2H), 4.63 (s, 2H), 4.49 (d, J = 9.6 Hz, 2H), 4.11 (dd, J = 9.7, 0.9 Hz, 2H), 2.23 (t, J = 2.5 Hz, 1H). LCMS (Method A): 3.60 min (544.3, MH⁺). |

Examples 26-27

The following examples were prepared using the general method described for Intermediate 17, from the appropriate intermediate and alkyl halide:

| Example No. | Compound | ¹H NMR/LCMS |
|---|---|---|
| 26 | 2-(4-(Cyclopropylmethyl)-7-fluoro-3-oxo-3,4-dihydrospiro[benzo[b][1,4]oxazine-2,1'-cyclopropan]-6-yl)-5-fluoroisoindoline-1,3-dione | (500 MHz, CDCl₃): δ 7.99 (dd, J = 8.3, 4.4 Hz, 1H), 7.65 (dd, J = 7.0, 2.1 Hz, 1H), 7.51-7.46 (m, 1H), 7.02 (d, J = 6.8 Hz, 1H), 6.83 (d, J = 9.7 Hz, 1H), 3.82 (d, J = 6.9 Hz, 2H), 1.44 (dd, J = 8.4, 5.4 Hz, 2H), 1.24 (dd, J = 8.3, 5.3 Hz, 2H), 1.19-1.13 (m, 1H), 0.57-0.52 (m, 2H), 0.43-0.39 (m, 2H). LCMS (Method D): 9.41 min (411.2, MH⁺). |

| Example No. | Compound | ¹H NMR/LCMS |
|---|---|---|
| 27 | 5-Fluoro-2-(7-fluoro-4-(2-methoxyethyl)-3-oxo-3,4-dihydrospiro[benzo[b][1,4]oxazine-2,1'-cyclopropan]-6-yl)isoindoline-1,3-dione 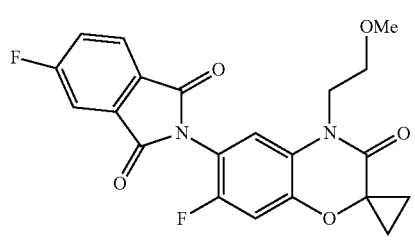 | (500 MHz, CDCl$_3$): δ 7.98 (dd, J = 8.2, 4.4 Hz, 1H), 7.65 (dd, J = 6.9, 2.3 Hz, 1H), 7.48 (td, J = 8.5, 2.3 Hz, 1H), 7.21 (d, J = 6.9 Hz, 1H), 6.80 (d, J = 9.6 Hz, 1H), 4.07 (t, J = 5.5 Hz, 2H), 3.65 (t, J = 5.5 Hz, 2H), 3.34 (s, 3H), 1.44 (dd, J = 8.4, 5.4 Hz, 2H), 1.25 (dd, J = 8.4, 5.3 Hz, 2H). LCMS (Method D): 8.67 min (415.2, MH$^+$). |

Example 28: 1-(7-Fluoro-3-oxo-4-(prop-2-yn-1-yl)-3,4-dihydrospiro[benzo[b][1,4]oxazine-2,1'-cyclopropan]-6-yl)pyrrolidine-2,5-dione

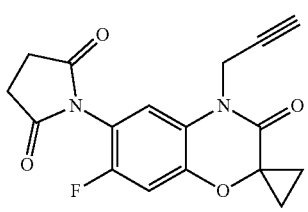 [SMILES: C#CCN1C(=O)C2(CC2)Oc2cc(F)c(N3C(=O)CCC3=O)cc21]

Intermediate 24 (126 mg, 0.363 mmol), HATU (173 mg, 0.454 mmol) and N,N-diisopropylethylamine (0.190 mL, 1.09 mmol) were dissolved in DCM (2.4 mL) in a 10 mL round-bottomed flask. The flask was sealed with a rubber septum and the reaction was allowed to proceed for approx. 18 h. at RT. The reaction was diluted with DCM (10 mL) and added to a mixture of water (10 mL), 1M aq. HCl (4 mL) and saturated brine (2 mL). The layers separated and the aqueous layer was extracted with DCM (3×10 mL). The combined organics were dried over MgSO$_4$, filtered and concentrated under reduced pressure to afford a colourless tar. The crude residue was purified by chromatography (SiO$_2$, 0-40% EtOAc in PE) to afford the title compound as an off-white solid (73 mg, 61%). ¹H NMR δ$_H$ (500 MHz, DMSO-d$_6$) 6.99 (d, J=6.7 Hz, 1H), 6.81 (d, J=9.7 Hz, 1H), 4.65 (d, J=2.5 Hz, 2H), 2.97 (d, J=4.2 Hz, 4H), 2.29 (t, J=2.5 Hz, 1H), 1.46 (dd, J=8.5, 5.4 Hz, 2H), 1.26 (dd, J=8.4, 5.4 Hz, 2H). LCMS (Method F): 1.52 min (329.1, MH$^+$).

Example 29: 1-(7-Fluoro-3-oxo-4-(prop-2-yn-1-yl)-3,4-dihydrospiro[benzo[b][1,4]oxazine-2,1'-cyclopropan]-6-yl)-4-methylpiperidine-2,6-dione

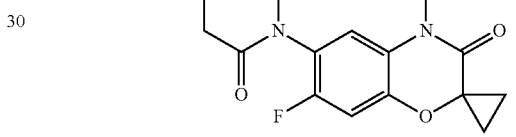

Prepared according to the procedure used for Example 28, using Intermediate 25 (152 mg, 0.406 mmol), HATU (193 mg, 0.508 mmol), N,N-diisopropylethylamine (0.212 mL, 1.21 mmol) and DCM (2.7 mL) to afford a crude, yellow tar. The crude residue was purified by chromatography (SiO$_2$, 0-35% EtOAc in PE) to afford the title compound as a yellow solid (89 mg, 62%). ¹H NMR δ$_H$ (500 MHz, CDCl$_3$) 6.88 (t, J=7.0 Hz, 1H), 6.76 (dd, J=9.5, 2.9 Hz, 1H), 4.65-4.61 (m, 2H), 2.94 (m, 2H), 2.61-2.41 (m, 3H), 2.26 (t, J=2.4 Hz, 1H), 1.46 (dd, J=8.5, 5.4 Hz, 2H), 1.25 (dd, J=8.5 Hz, 2H), 1.20 (t, J=6.4 Hz, 3H). LCMS (Method F): 1.67 min (357.2, MH$^+$).

Example 30: 5-Fluoro-2-(7-fluoro-4-(3-iodoprop-2-yn-1-yl)-3-oxo-3,4-dihydrospiro[benzo[b][1,4]oxazine-2,1'-cyclopropan]-6-yl)isoindoline-1,3-dione

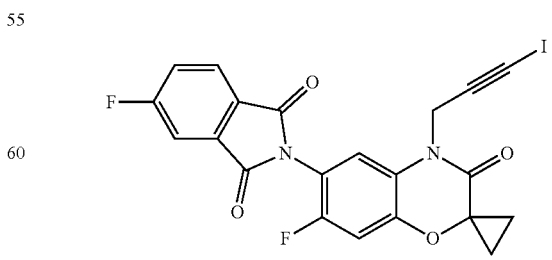

Silver nitrate (2.58 mg, 0.015 mmol) followed by N-iodosuccinimide (35.9 mg, 0.160 mmol) were added to a solution of Example 5 (60 mg, 0.15 mmol) in anhydrous DMF (0.3 mL). The reaction was allowed to proceed at RT for 4 h. To the reaction mixture was added water (3 mL), saturated brine (0.5 mL) and EtOAc (3 mL) and the layers separated. The aqueous layer was extracted with EtOAc (2×3 mL). The combined organics were washed with saturated NaHCO$_3$ (3 mL) and brine (3 mL), dried over MgSO$_4$ and concentrated in vacuo to afford the title compound as a pale yellow solid. $^1$H NMR $\delta_H$ (500 MHz, CDCl$_3$) 8.00 (dd, J=8.3, 4.3 Hz, 1H), 7.67 (dd, J=6.9, 2.2 Hz, 1H), 7.49 (td, J=8.6, 2.3 Hz, 1H), 7.07 (d, J=6.7 Hz, 1H), 6.84 (d, J=9.6 Hz, 1H), 4.80 (s, 2H), 1.49 (dd, J=8.5, 5.4 Hz, 2H), 1.28 (dd, J=8.4, 5.4 Hz, 2H).

LCMS (Method D): 9.34 min (521.1, MH$^+$).

Example 31: (Z)-7-Fluoro-6-((3-oxotetrahydro-1H, 3H-[1,3,4]thiadiazolo[3,4-a]pyridazin-1-ylidene) amino)-4-(prop-2-yn-1-yl)spiro[benzo[b][1,4] oxazine-2,1'-cyclopropan]-3(4H)-one

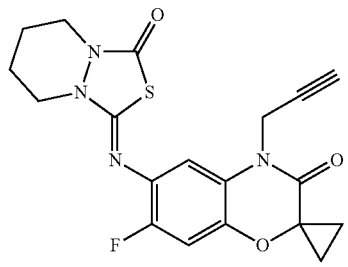 [SMILES: C#CCN1C(=O)C2(CC2)Oc2cc(F)c(/N=c3\sc(=O)n4n3CCCC4)cc21]

Intermediate 4 (100 mg, 0.414 mmol), sodium hydrogen carbonate (119 mg, 1.42 mmol) and THF (2 mL) were added to a 10 mL round-bottomed flask. The flask was cooled to 0° C. by submerging it in an ice bath and was purged with nitrogen. Thiophosgene (0.034 mL, 0.45 mmol) was then added in a dropwise manner. The reaction was then allowed to warm to RT before being allowed to proceed for 2 h. Hexahydropyridazine dihydrochloride (71.1 mg, 0.447 mmol) was then added and the reaction was allowed to proceed for 1 h. THF (2 mL) and triphosgene (181 mg, 0.609 mmol) were then added to the reaction mixture and the reaction was allowed to proceed for 18 h. Water (10 mL) was added to the reaction and the layers separated. The aqueous layer was extracted with EtOAc (3×10 mL) and the combined organics were dried using anhydrous Na$_2$SO$_4$ and concentrated under reduced pressure to afford a colourless oil. The crude residue was purified by chromatography (SiO$_2$, 0-25% EtOAc in PE) to afford the title compound as a yellow solid (57 mg, 35%). $^1$H NMR $\delta_H$ (500 MHz, DMSO-d$_6$) 7.01 (d, J=10.5 Hz, 1H), 6.91 (d, J=7.9 Hz, 1H), 4.72 (d, J=2.3 Hz, 2H), 3.81-3.73 (m, 2H), 3.73-3.64 (m, 2H), 1.89-1.79 (m, 2H), 1.79-1.65 (m, 2H), 1.30 (dd, J=8.3, 5.3 Hz, 2H), 1.26 (dd, J=8.3, 5.2 Hz, 2H). LCMS (Method F): 1.97 min (401.2, MH$^+$).

Example 32: 3-(7-Fluoro-3-oxo-4-(prop-2-yn-1-yl)-3,4-dihydrospiro[benzo[b][1,4]oxazine-2,1'-cyclopropan]-6-yl)-6-(trifluoromethyl)pyrimidine-2,4(1H,3H)-dione

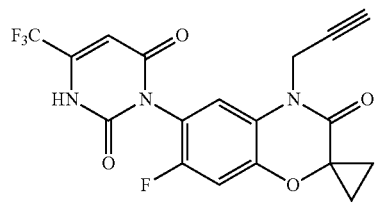 [SMILES: C#CCN1C(=O)C2(CC2)Oc2cc(F)c(-n3c(=O)cc(C(F)(F)F)[nH]c3=O)cc21]

Intermediate 4 (80 mg, 0.33 mmol), Intermediate 23 (81 mg, 0.39 mmol) and acetic acid (3.3 mL) were added to a 10 mL round-bottomed flask. The reaction was heated to 120° C. for 2 h. The reaction was allowed to cool to RT and diluted with water (5 mL) and the mixture was extracted with EtOAc (3×10 mL). The combined organics were washed with sat. aq. NaHCO$_3$ (10 mL) and sat. brine (10 mL), dried over MgSO$_4$ and concentrated under reduced pressure to afford the title compound as a brown solid (119 mg, 89%). $^1$H NMR $\delta_H$ (500 MHz, DMSO-d$_6$) 12.77 (s, 1H), 7.38 (m, 1H), 7.14 (d, J=9.8 Hz, 1H), 6.35 (s, 1H), 4.64 (q, J=18.0 Hz, 2H), 3.28 (d, J=2.1 Hz, 1H), 1.33 (m, 4H).

Example 33: 3-(7-Fluoro-3-oxo-4-(prop-2-yn-1-yl)-3,4-dihydrospiro[benzo[b][1,4]oxazine-2,1'-cyclobutan]-6-yl)-6-(trifluoromethyl)pyrimidine-2,4(1H,3H)-dione

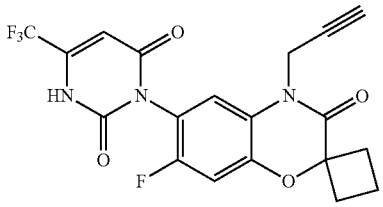 [SMILES: C#CCN1C(=O)C2(CCC2)Oc2cc(F)c(-n3c(=O)cc(C(F)(F)F)[nH]c3=O)cc21]

Prepared according to the experimental procedure used for Example 32, using Intermediate 17 (0.050 g, 0.19 mmol), acetic acid (2 mL) and 2-(dimethylamino)-4-(trifluoromethyl)-6H-1,3-oxazin-6-one (0.048 g, 0.23 mmol). Chromatography (SiO$_2$, 0-33% EtOAc— in PE) of the residue gave the title compound as a cream oil (0.04 g, 49%). $^1$H NMR $\delta_H$ (500 MHz, CDCl$_3$) 9.61 (s, 1H), 7.02 (d, J=6.8 Hz, 1H), 6.97 (d, J=9.7 Hz, 1H), 6.29 (s, 1H), 4.67 (d, J=3.9, 2.5 Hz, 2H), 2.75-2.62 (m, 2H), 2.44-2.32 (m, 2H), 2.28 (t, J=2.5 Hz, 1H), 2.04-1.90 (m, 2H). LCMS (Method B): 3.01 min (422.4, MH$^-$).

Example 34: 3-(7-Fluoro-3-oxo-4-(prop-2-yn-1-yl)-3,4-dihydrospiro[benzo[b][1,4]oxazine-2,1'-cyclopropan]-6-yl)-1-methyl-6-(trifluoromethyl)pyrimidine-2,4(1H,3H)-dione

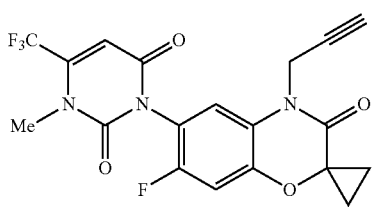 [SMILES: C#CCN1C(=O)C2(CC2)Oc2cc(F)c(-n3c(=O)cc(C(F)(F)F)n(C)c3=O)cc21]

Example 32 (80 mg, 0.33 mmol), potassium carbonate (100 mg, 0.726 mmol), iodomethane (90.0 μL, 1.45 mmol) and DMF (2.9 mL) were added to a 20 mL round-bottomed flask. The flask was fitted with a rubber septum and the reaction was allowed to proceed at RT for approx. 18 h. Water (30 mL) and DCM (20 mL) were added to the reaction mixture and the layers separated. The aqueous layer was extracted with 3×20 mL DCM and the combined organics were washed with water (20 mL), dried with $Na_2SO_4$ and concentrated under reduced pressure to afford the title compound as a white solid (76 mg, 62%). $^1$H NMR $\delta_H$ (500 MHz, DMSO-$d_6$) 7.37 (d, J=7.0 Hz, 1H), 7.17 (d, J=9.9 Hz, 1H), 6.60 (s, 1H), 4.62 (m, 2H), 3.43 (s, 3H), 3.31 (t, J=2.4 Hz, 1H), 1.39-1.28 (m, 4H). LCMS (Method F): 1.86 min (424.1, MH$^+$).

Example 35

The following example was prepared using the general method described for Example 1, from the appropriate intermediate and anhydride derivative:

Example 36: 5-Fluoro-2-(7-fluoro-4-(oxiran-2-ylmethyl)-3-oxo-3,4-dihydrospiro[benzo[b][1,4]oxazine-2,1'-cyclopropan]-6-yl)isoindoline-1,3-dione

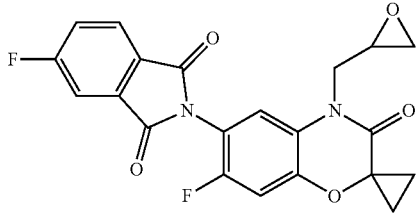 [SMILES: O=C1c2ccc(F)cc2C(=O)N1c1cc2c(cc1F)OC1(CC1)C(=O)N2CC1CO1]

N,N-diisopropylethylamine (0.765 mL, 4.39 mmol) was added to a solution of Intermediate 30 (193 mg, 0.732 mmol), HATU (835 mg, 2.20 mmol) and 4-fluorophthalic acid (135 mg, 0.732 mmol) in DCM (5 mL). The mixture was stirred at RT for 18 h. The reaction was diluted with DCM (10 mL) and added to water (10 mL), 1 M aq. HCl (4 mL) and saturated brine (2 mL). The layers were separated and the aqueous layer was extracted with DCM (3×10 mL). The combined organics were washed with 1 M aq. HCl (2×5 mL), dried over $MgSO_4$, and concentrated in vacuo. The residue was purified by column chromatography ($SiO_2$, 0-60% EtOAc+1% NEt$_3$ in PE) to afford the title compound as an off-white solid (52 mg, 17%). $^1$H NMR $\delta_H$ (500 MHz, CDCl$_3$) 7.98 (dd, J=8.3, 4.4 Hz, 1H), 7.64 (dd, J=6.9, 2.2 Hz, 1H), 7.48 (td, J=8.5, 2.3 Hz, 1H), 7.25 (d, J=7.0 Hz, 1H), 6.82 (d, J=9.6 Hz, 1H), 4.64 (dd, J=15.3, 2.4 Hz, 1H), 3.51 (dd, J=15.3, 6.4 Hz, 1H), 3.23 (m, 1H), 2.86 (t, J=4.4 Hz, 1H), 2.66 (dd, J=4.6, 2.6 Hz, 1H), 1.38-1.23 (m, 4H). LCMS (Method D): 8.75 min (413.1, MH+).

Examples 37-38

The following examples were prepared using the general method described in Example 31 from the appropriate Intermediate:

| Example No. | Compound | $^1$H NMR/LCMS |
|---|---|---|
| 35 | 2-(7-Fluoro-6-(5-fluoro-1,3-dioxoisoindolin-2-yl)-3-oxospiro[benzo[b][1,4]oxazine-2,1'-cyclopropan]-4(3H)-yl)propanoic acid 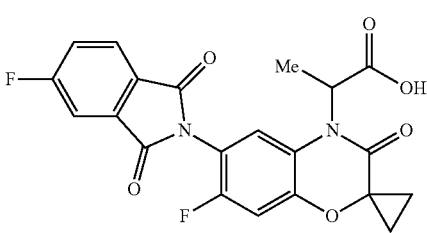 | (500 MHz, DMSO-$d_6$): δ 12.92 (s, 1H), 8.10 (dd, J = 8.3, 4.6 Hz, 1H), 7.95 (dd, J = 7.4, 2.3 Hz, 1H), 7.82-7.77 (m, 1H), 7.47 (d, J = 7.0 Hz, 1H), 7.23 (d, J = 9.8 Hz, 1H), 4.94 (q, J = 7.2 Hz, 1H), 1.49 (d, J = 7.0 Hz, 3H), 1.38-1.19 (m, 4H). LCMS (Method D): 8.18 min (429.1, MH$^+$). |

| Example No. | Compound | ¹H NMR/LCMS |
|---|---|---|
| 37 | (Z)-4-(Cyclopropylmethyl)-7-fluoro-6-((3-oxotetrahydro-1H,3H-[1,3,4]thiadiazolo[3,4-a]pyridazin-1-ylidene)amino)spiro[benzo[b][1,4]oxazine-2,1'-cyclopropyl]-3(4H)-one | (500 MHz, DMSO-d₆): δ 6.99 (d, J = 8.0 Hz, 1H), 6.97 (d, J = 10.5 Hz, 1H), 3.82 (d, J = 6.9 Hz, 2H), 3.77-3.72 (m, 2H), 3.72-3.62 (m, 2H), 1.87-1.79 (m, 2H), 1.78-1.71 (m, 2H), 1.28-1.24 (m, 2H), 1.23-1.19 (m, 2H), 1.16-1.09 (m, 1H), 0.,50-0.42 (m, 2H), 0.35-0.28 (m, 2H). LCMS (Method F): 2.05 min (417.2, MH⁺). |
| 38 | Methyl (Z)-2-(7-fluoro-3-oxo-6-((3-oxotetrahydro-1H,3H-[1,3,4]thiadiazolo[3,4-a]pyridazin-1-ylidene)amino)spiro[benzo[b][1,4]oxazine-2,1'-cyclopropan]-4(3H)-yl)propanoate | (500 MHz, DMSO-d₆): δ 7.02 (d, J = 10.4 Hz, 1H), 6.90 (d, J = 7.8 Hz, 1H), 5.10 (q, J = 6.9 Hz, 1H), 3.77-3.71 (m, 2H), 3.68 (td, J = 5.8, 1.4 Hz, 2H), 3.62 (s, 3H), 1.86-1.79 (m, 2H), 1.78-1.71 (m, 2H), 1.47 (d, J = 6.9 Hz, 3H), 1.31-1.16 (m, 4H). LCMS (Method F): 1.96 min (449.1, MH⁺). |

Examples 39-43

The following examples were prepared using the general method described in Example 34 from the appropriate Intermediate and alkyl halide:

| Example No. | Compound | ¹H NMR/LCMS |
|---|---|---|
| 39 | 3-(4-(Cyclopropylmethyl)-7-fluoro-3-oxo-3,4-dihydrospiro[benzo[b][1,4]oxazine-2,1'-cyclopropan]-6-yl)-1-methyl-6-(trifluoromethyl)pyrimidine-2,4(1H,3H)-dione | (500 MHz, CDCl₃): δ 6.83 (d, J = 9.5 Hz, 1H), 6.64 (dd, J = 8.3, 6.7 Hz, 1H), 6.37 (d, J = 3.1 Hz, 1H), 5.31-5.20 (m, 1H), 3.72 (d, J = 2.2 Hz, 3H), 3.58-3.54 (m, 3H), 1.61 (d, J = 7.2 Hz, 3H), 1.55-1.49 (m, 2H), 1.41-1.20 (m, 2H) LCMS (Method C): 3.30 min (472.0, MH⁺). |

| Example No. | Compound | ¹H NMR/LCMS |
| --- | --- | --- |
| 40 | Methyl 2-(7-fluroo-6-(3-methyl-2,6-dioxo-4-(trifluoromethyl)-3,6-dihydropyrimidin-1(2H)-yl)-3-oxospiro[benzo[b][1,4]oxazine-2,1'-cyclopropan]-4(3H)-yl)propanoate | (500 MHz, DMSO-d$_6$): δ 7.49 (d, J = 7.1 Hz, 1H), 7.12 (d, J = 9.9 Hz, 1H), 6.60 (s, 1H), 3.83-3.65 (m, 2H), 3.43 (s, 3H), 1.29 (dd, J = 7.8, 4.6 Hz, 4H), 1.10 (tt, J = 7.8, 4.3 Hz, 1H), 0.47-0.44 (m, 2H), 0.34-0.31 (m, 2H). LCMS (Method C): 3.55 min (440.1, MH$^+$). |
| 41 | 3-(7-Fluoro-3-oxo-4-(prop-2-yn-1-yl)-3,4-dihydrospiro[benzo[b][1,4]oxazine-2,1'-cyclopropan]-6-yl)-1-(prop-2-yn-1-yl)-6-(trifluoromethyl)pyrimidine-2,4-(1H,3H)-dione | (500 MHz, DMSO-d$_6$): δ 7.44 (d, J = 7.0 Hz, 1H), 7.19 (d, J = 9.9 Hz, 1H), 6.69 (s, 1H), 4.74-4.50 (m, 4H), 3.45 (t, J = 2.3 Hz, 1H), 3.30 (t, J = 2.4 Hz, 1H), 1.37-1.30 (m, 4H). LCMS (Method F): 1.82 min (446.1, MH$^-$). |
| 42 | Methyl 2-(3-(7-fluroo-3-oxo-4-(prop-2-yn-1-yl)-3,4-dihydrospiro[benzo[b][1,4]oxazine-2,1'-cyclopropan]-6-yl)-2,4-dioxo-6-(trifluoromethyl)-3,4-dihydropyrimidin-1(2H)-yl)acetate | (500 MHz, DMSO-d$_6$): δ 7.39 (d, J = 7.0 Hz, 1H), 7.19 (d, J = 9.9 Hz, 1H), 6.76 (s, 1H), 4.86-4.53 (m, 4H), 3.71 (s, 3H), 3.31 (t, J = 2.3 Hz, 1H), 1.41-1.25 (m, 4H). LCMS (Method F): 1.79 min (482.1, MH$^+$). |

| Example No. | Compound | ¹H NMR/LCMS |
|---|---|---|
| 43 | 3-(7-Fluoro-3-oxo-4-(prop-2-yn-1-yl)-3,4-dihydrospiro[benzo[b][1,4]oxazine-2,1'-cyclopropan]-6-yl)-1-propyl-6-(trifluoromethyl)pyrimidine-2,4-(1H,3H)-dione | (500 MHz, DMSO-d₆): δ 7.41 (d, J = 7.1 Hz, 1H), 7.17 (d, J = 9.8 Hz, 1H), 6.60 (s, 1H), 4.71-4.33 (m, 1H), 3.86-3.68 (m, 2H), 1.75-1.54 (m, 4H), 1.38-1.29 (m, 4H), 0.89 (t, J = 7.4 Hz, 3H). LCMS (Method F): 2.00 min (452.1, MH⁺). |

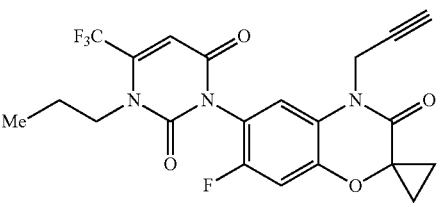

Example 44: 2-(7-Fluoro-3-oxo-4-(prop-2-yn-1-yl)-3,4-dihydrospiro[benzo[b][1,4]oxazine-2,1'-cyclopropan]-6-yl)tetrahydro-1H-pyrrolo[1,2-c]imidazole-1,3(2H)-dione Example 45: 2-(7-Fluoro-3-oxo-4-(prop-2-yn-1-yl)-3,4-dihydrospiro[benzo[b][1,4]oxazine-2,1'-cyclopropan]-6-yl)tetrahydro-1H-imidazo[5,1-c][1,4]oxazine-1,3(2H)-dione

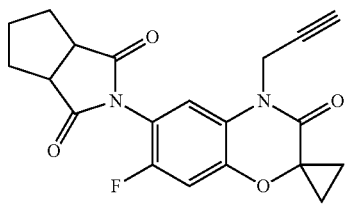 [SMILES: C#CCN1C(=O)C2(CC2)Oc2cc(F)c(N3C(=O)C4CCCC4C3=O)cc21]

N,N'—Carbonyl diimidazole (296 mg, 1.83 mmol) was added to a solution of Intermediate 4 (150 mg, 0.609 mmol) and triethylamine (0.127 mL, 0.914 mmol) in MeCN (10 mL). The reaction was heated at 80° C. for 1 h. DL-proline (70.1 mg, 0.609 mmol) was then added and the reaction continued at 80° C. for 2 h. The reaction was allowed to cool to RT and was poured onto 1 M aq. HCl and extracted with EtOAc (3×20 mL). The organics were dried over MgSO₄ and concentrated in vacuo. The crude residue was dissolved in dioxane (5 mL) and HCl (4 M dioxane solution, 0.30 mL, 1.22 mmol) was added. The reaction was heated at 70° C. for 2 h. The reaction was cooled to RT and concentrated in vacuo. The crude residue was purified by chromatography (SiO₂, 0-50% EtOAc in PE) to afford the title compound as a white solid (52 mg, 23%). ¹H NMR δ$_H$ (500 MHz, DMSO-d₆) 7.37 (d, J=7.0 Hz, 1H), 7.17 (d, J=10.0 Hz, 1H), 4.74-4.60 (m, 2H), 4.45 (t, J=8.3 Hz, 1H), 3.61-3.52 (m, 1H), 3.33 (s, 1H), 3.31 (t, J=2.3 Hz, 1H), 3.25 (ddt, J=10.9, 8.5, 3.9 Hz, 1H), 2.21 (s, 1H), 2.11 (d, J=10.4 Hz, 1H), 2.10-2.01 (m, 1H), 1.35-1.28 (m, 4H). LCMS (Method C): 2.93 min (370.1, MH⁺).

Intermediate 4 (50.0 mg, 0.203 mmol) and anhydrous THF (2 mL) were added to a 5 mL round-bottomed flask. The flask was fitted with a rubber septum and purged with nitrogen before the addition of triethylamine (0.059 mL, 0.42 mmol) and triphosgene (63.3 mg, 0.213 mmol, as a solution in anhydrous THF (0.4 mL)) and the reaction was allowed to proceed at RT for 2 h. 3-Morpholinecarboxylic acid (32.0 mg, 0.244 mmol), anhydrous DCM (5 mL) and triethylamine (0.0590 mL, 0.426 mmol) were added and the reaction was allowed to proceed for 18 h at RT The reaction was added to 1 M aq. HCl (20 mL) and EtOAc (10 mL) and the layers separated. The aqueous layer was extracted with EtOAc (3×10 mL) and the combined organics were dried using MgSO₄ and concentrated in vacuo to afford a crude brown oil. The crude residue was dissolved in dioxane (12 mL), HCl (4 M solution in dioxane, 0.609 mL, 2.44 mmol) was added and the reaction was heated at 70° C. for 3 h. The reaction mixture was concentrated in vacuo to afford a crude brown solid. The crude residue was purified by chromatography (SiO₂, 0-60% EtOAc in PE) to afford the title compound as an off-white solid (62 mg, 80%). ¹H NMR δ$_H$ (500 MHz, DMSO-d₆) 7.36 (d, J=6.5 Hz, 1H), 7.18 (d, J=10.0 Hz, 1H), 4.73-4.59 (m, 2H), 4.54 (dd, J=8.7, 4.3 Hz, 1H), 4.19 (dd, J=10.8, 4.5 Hz, 1H), 3.96-3.85 (m, 2H), 3.68-3.38 (m, 2H), 3.31 (t, J=2.4 Hz, 1H), 3.20 (td, J=13.4, 4.0 Hz, 1H), 1.38-1.27 (m, 4H). LCMS (Method F): 0.96 min (386.1, MH⁺).

Examples 46-52

The following examples were prepared using the general method described in Example 45 from the appropriate Intermediate and amino acid derivative:

| Example No. | Compound | ¹H NMR/LCMS |
|---|---|---|
| 46 | 2-(4-(Cyclopropylmethyl)-7-fluoro-3-oxo-3,4-dihydrospiro[benzo[b][1,4]oxazine-2,1'-cyclopropan]-6-yl)-6-hydroxytetrahydro-1H-pyrrolo[1,2-c]imidazole-1,3-(2H)-dione | (500 MHz, DMSO-$d_6$): δ 7.47 (d, J = 7.2 Hz, 1H), 7.12 (d, J = 10.0 Hz, 1H), 5.38 (s, 1H), 4.58 (s, 1H), 3.87-3.68 (m, 3H), 3.09 (d, J = 11.6 Hz, 1H), 2.54 (t, J = 5.6 Hz, 1H), 2.09 (s, 1H), 1.36-1.04 (m, 6H), 0.55-0.41 (m, 2H), 0.40-0.26 (m, 2H). LCMS (Method F): 1.55 min (402.2, MH⁺). |
| 47 | 2-(7-Fluoro-3-oxo-4-(prop-2-yn-1-yl)-3,4-dihydrospiro[benzo[b][1,4]oxazine-2,1'-cyclopropan]-6-yl)tetrahydroimidazo[1,5-a]pyridine-1,3(2H,5H)-dione | (500 MHz, CDCl₃): δ 7.05 (d, J = 6.8 Hz, 1H), 6.79 (d, J = 9.7 Hz, 1H), 4.66 (d, J = 2.5 Hz, 2H), 4.33-4.21 (m, 1H), 4.05-3.93 (m, 1H), 2.94 (td, J = 12.5, 3.6 Hz, 1H), 2.38-2.24 (m, 2H), 2.08 (d, J = 7.0 Hz, 1H), 1.81 (d, J = 11.4 Hz, 1H), 1.65-1.56 (m, 3H), 1.48-1.40 (m, 2H), 1.30-1.18 (m, 2H). LCMS (Method C): 3.14 min (384.1, MH⁺). |
| 48 | 2-(4-(Cyclopropylmethyl)-7-fluoro-3-oxo-3,4-dihydrospiro[benzo[b][1,4]oxazine-2,1'-cyclopropan]-6-yl)tetrahydro-1H-imidazo[5,1-c][1,4]oxazine-1,3(2H)-dione | (500 MHz, DMSO-$d_6$): δ 7.48 (d, J = 7.1 Hz, 1H), 7.14 (d, J = 10.0 Hz, 1H), 4.53 (s, 1H), 4.19 (s, 1H), 3.94-3.88 (m, 2H), 3.86-3.75 (m, 2H), 3.43 (td, J = 11.7, 3.2 Hz, 1H), 3.20 (td, J = 13.4, 4.0 Hz, 1H), 1.34-1.10 (m, 6H), 0.50-0.45 (m, 2H), 0.38-0.34 (m, 2H). LCMS (Method F): 1.66 min (402.2, MH⁺). |

-continued

| Example No. | Compound | ¹H NMR/LCMS |
|---|---|---|
| 49 | Methyl 2-(6-(1,3-dioxotetrahydro-1H-imidazo[5,1-c][1,4]oxazin-2(3H)-yl)-7-fluoro-3-oxospiro[benzo[b][1,4]oxazine-2,1'-cyclopropan]-4(3H)-yl)propanoate | LCMS (Method F): 1.50 min (434.1, MH⁻). |
| 50 | 2-(6-(1,3-Dioxotetrahydro-1H-imidazo[5,1-c][1,4]oxazin-2(3H)-yl)-7-fluoro-3-oxospiro[benzo[b][1,4]oxazine-2,1'-cyclopropan]-4(3H)-yl)acetonitrile | (500 MHz, DMSO-$d_6$): δ 7.49 (d, J = 7.0 Hz, 1H), 7.25 (d, J = 9.9 Hz, 1H), 5.02 (s, 2H), 4.57 (tt, J = 14.6, 7.5 Hz, 1H), 4.23 (dd, J = 10.7, 4.7 Hz, 1H), 3.99-3.85 (m, 2H), 3.67-3.38 (m, 2H), 3.28-3.15 (m, 1H), 1.47-1.29 (m, 4H). LCMS (Method F): 1.48 min (387.1, MH⁺). |
| 51 | 2-(7-Fluoro-4-(3-methylbut-2-en-1-yl)-3-oxo-3,4-dihydrospiro[benzo[b][1,4]oxazine-2,1'-cyclopropan]-6-yl)tetrahydro-1H-imidazo[5,1-c][1,4]oxazine-1,3(2H)-dione | (500 MHz, DMSO-$d_6$): δ 7.19 (d, J = 6.9 Hz, 1H), 7.13 (d, J = 10.0 Hz, 1H), 5.10 (t, J = 6.5 Hz, 1H), 4.63-4.39 (m, 3H), 4.19 (dd, J = 10.7, 4.4 Hz, 1H), 3.91 (dd, J = 11.5, 3.4 Hz, 2H), 3.41 (td, J = 11.8, 3.1 Hz, 1H), 3.19 (td, J = 13.2, 4.0 Hz, 1H), 1.73 (s, 3H), 1.67 (s, 3H), 1.39-1.19 (m, 5H). LCMS (Method F): .180 min (416.2, MH⁺). |

| Example No. | Compound | ¹H NMR/LCMS |
|---|---|---|
| 62 | 2-(4-(Cyclopropylmethyl)-7-fluoro-3-oxo-3,4-dihydrospiro[benzo[b][1,4]oxazine-2,1'-cyclopropan]-6-yl)tetrahydro-1H-pyrrolo[1,2-c]imidazole-1,3(2H)-dione | LCMS (Method F): 1.73 min (386.2, MH⁺). |
| 53 | 2-(7-Fluoro-3-oxo-4-(prop-2-yn-1-yl)-3,4-dihydrospiro[benzo[b][1,4]oxazine-2,1'-cyclopropan]-6-yl)tetrahydro-1H-imidazo[5,1-c][1,4]thiazine-1,3(2H)-dione | (500 MHz, DMSO-d₆): δ 7.33 (d, J = 6.6 Hz, 1H), 7.18 (d, J = 10.0 Hz, 1H), 4.66 (s, 2H), 4.43 (s, 1H), 4.29 (dt, J = 13.2, 2.8 Hz, 1H), 3.32 (t, J = 2.4 Hz, 1H), 3.13 (td, J = 13.3, 2.9 Hz, 1H), 3.01-2.94 (m, 1H), 2.80-2.71 (m, 1H), 2.69-2.62 (m, 2H), 1.36-1.28 (m, 4H). LCMS (Method F): 1.71 min (402.2, MH⁺). |

Comparative Example: 3-(7-Fluoro-3-oxo-4-(prop-2-yn-1-yl)-3,4-dihydrospiro[benzo[b][1,4]oxazine-2,1'-cyclopropan]-6-yl)-1,5-dimethyl-6-thioxo-1,3,5-triazinane-2,4-dione

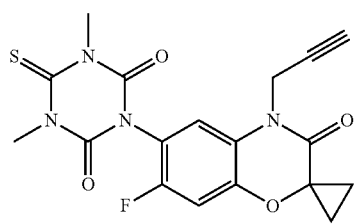 [SMILES: C#CCN1C(=O)C2(CC2)Oc2cc(F)c(-n3c(=O)n(C)c(=S)n(C)c3=O)cc21]

Trichloromethyl chloroformate (36 μL, 0.30 mmol) was added to a solution of Intermediate 4 (66 mg, 0.27 mmol) in toluene (2.5 mL), and the reaction was heated to 110° C. for 6 h. The reaction mixture was concentrated in vacuo, and the residue re-dissolved in toluene (2.5 mL). N,N'-Dimethylthiourea (34 mg, 0.32 mmol), triethylamine (37 μL, 0.27 mmol) and N,N'-carbonyl diimidazole (87 mg, 0.54 mmol) were added, and the reaction mixture was heated to 80° C. for 18 h. After cooling to RT, the reaction mixture was partitioned between EtOAc and water. The aqueous layer was extracted with EtOAc (×3). The combined EtOAc layers were washed (aq. NaHCO₃, then brine), dried (MgSO₄) and concentrated in vacuo. The residue was purified by chromatography (SiO₂, 0-40% EtOAc in PE) and the title compound was isolated as a yellow solid (54 mg, 50%). ¹H NMR δ_H (500 MHz, CDCl₃) 7.10 (d, J=6.8 Hz, 1H), 6.85 (d, J=9.6 Hz, 1H), 4.67 (d, J=2.5 Hz, 2H), 3.82 (s, 6H), 2.31 (t, J=2.5 Hz, 1H), 1.51 (dd, J=8.5, 5.5 Hz, 2H), 1.30 (dd, J=8.4, 5.4 Hz, 2H). LCMS (Method E): 1.91 min (no ionisation).

Example 54—Testing the Herbicidal Activity of Compounds of the Invention

The compounds were screened at three concentrations (0.2, 1 and 5 kg/ha) against 2 weed species (*Stellaria media*—Chickweed and *Lolium perenne*).

The seeds were sown in the cells of 96 cell trays (4-6 seeds per cell). For the pre-emergence assay, 75 μL of a suspension of the test compound, at the above doses, was added on top of the soil 1 day after sowing. For the post-emergence assay, the seedlings were sprayed with 200 μL of a suspension of the test compound two weeks after sowing. The formulation used is 25% acetone and 75% water/0.01% Tween 20.

Each treatment was replicated three times. The plants were kept in a glasshouse (uncontrolled conditions) and assessed 7 days after treatment. A small number of compounds were tested in a first trial. The results of the first trial are shown in Table 1. A larger number of compounds were tested in a second trial. The results of the second trial are shown in Table 2.

The assessment was based on the % control of plant growth in each cell. The data is presented in Tables 1 and 2 in which A represents a percentage control between 80 and 100%; B represents a percentage control of 20-80%; C represents a percentage control below 20% and D indicates that the compound was not tested at that concentration.

All of the compounds showed some herbicidal activity against the weed species.

TABLE 1

| | Pre-Emergence | | | | | | Post-Emergence | | | | | |
|---|---|---|---|---|---|---|---|---|---|---|---|---|
| | Stellaria | | | Lollium | | | Stellaria | | | Lollium | | |
| | kg/ha | | | | | | | | | | | |
| Example | 0.2 | 1 | 5 | 0.2 | 1 | 5 | 0.2 | 1 | 5 | 0.2 | 1 | 5 |
| Comparative Example | C | C | C | C | B | A | C | B | B | B | B | A |
| 1 | C | C | C | B | B | B | C | B | B | C | B | A |
| 2 | B | B | B | C | C | C | B | B | B | C | C | C |
| 3 | B | A | A | C | B | A | B | B | B | B | A | A |
| 4 | A | A | A | A | A | A | B | B | B | A | A | A |

TABLE 2

| | Pre-Emergence | | | | | | Post-Emergence | | | | | |
|---|---|---|---|---|---|---|---|---|---|---|---|---|
| | Stellaria | | | Lollium | | | Stellaria | | | Lollium | | |
| | kg/ha | | | | | | | | | | | |
| Example | 0.2 | 1 | 5 | 0.2 | 1 | 5 | 0.2 | 1 | 5 | 0.2 | 1 | 5 |
| Comparative Example | B | A | A | C | B | A | B | A | A | B | B | A |
| 1 | B | A | A | B | B | A | A | A | A | B | A | A |
| 2 | B | B | B | C | C | C | B | B | B | C | C | C |
| 4 | A | A | A | A | A | A | A | A | A | A | A | A |
| 5 | D | A | A | D | B | A | A | A | A | B | B | A |
| 6 | B | B | A | C | C | B | B | A | A | B | A | A |
| 7 | A | A | A | B | A | A | A | A | A | C | B | B |
| 8 | A | A | A | B | A | A | A | A | A | B | A | A |
| 9 | C | C | B | C | C | B | C | C | B | C | C | B |
| 10 | B | A | A | C | C | C | B | A | A | C | C | C |
| 13 | B | A | A | C | C | B | A | A | A | C | C | C |
| 14 | C | C | C | C | C | C | C | C | C | C | C | C |
| 15 | A | A | A | B | A | A | A | A | A | B | A | A |
| 16 | A | A | A | C | B | A | A | A | A | B | B | A |
| 17 | B | B | A | C | B | B | C | B | B | C | C | C |
| 18 | A | A | A | A | A | A | A | A | A | B | A | A |
| 19 | A | A | A | B | A | A | A | A | A | B | A | A |
| 20 | C | B | B | C | C | C | B | A | A | C | C | C |
| 21 | A | A | A | C | B | A | A | A | A | C | B | B |
| 22 | A | A | A | C | B | B | A | A | A | B | B | A |
| 23 | C | A | A | C | B | A | A | A | A | C | C | C |
| 24 | C | B | B | C | B | B | C | C | C | C | C | C |
| 25 | B | B | B | C | C | C | C | C | C | C | C | C |
| 26 | A | A | A | A | A | A | A | A | A | A | A | A |
| 27 | A | A | A | B | A | A | A | A | A | B | A | A |
| 28 | A | A | A | A | A | A | A | A | A | B | A | A |
| 29 | A | A | A | A | A | A | A | A | A | C | B | B |
| 30 | A | A | A | B | B | A | A | A | A | C | C | C |
| 31 | A | A | A | A | A | A | A | A | A | A | A | A |
| 33 | C | B | B | C | C | C | C | C | B | C | C | C |
| 34 | A | A | A | B | A | A | A | A | A | B | A | A |
| 35 | C | B | B | C | B | B | A | A | A | C | B | B |
| 36 | C | B | A | C | B | B | A | A | A | C | B | B |
| 37 | D | D | D | D | D | D | A | A | A | B | B | A |
| 38 | D | D | D | D | D | D | A | A | A | B | B | A |
| 39 | A | A | A | A | A | A | A | A | A | A | A | A |
| 40 | A | A | A | B | A | A | A | A | A | B | B | A |
| 41 | A | A | A | A | A | A | A | A | A | C | B | A |
| 42 | B | A | A | C | B | A | A | A | A | B | A | A |
| 43 | B | A | A | B | A | A | A | A | A | B | A | A |
| 44 | A | A | A | C | B | A | A | A | A | A | A | A |
| 45 | D | D | D | D | D | D | A | A | A | A | A | A |
| 46 | D | D | D | D | D | D | C | C | C | C | C | C |
| 47 | A | A | B | A | A | A | A | A | A | A | A | A |
| 48 | D | D | D | D | D | D | A | A | A | C | C | B |
| 49 | D | D | D | D | D | D | A | A | A | C | C | C |

TABLE 2-continued

| | Pre-Emergence | | | | | | Post-Emergence | | | | | |
|---|---|---|---|---|---|---|---|---|---|---|---|---|
| | Stellaria | | | Lollium | | | Stellaria | | | Lollium | | |
| | kg/ha | | | | | | | | | | | |
| Example | 0.2 | 1 | 5 | 0.2 | 1 | 5 | 0.2 | 1 | 5 | 0.2 | 1 | 5 |
| 50 | D | D | D | D | D | D | A | A | A | C | C | C |
| 51 | D | D | D | D | D | D | A | A | A | C | C | C |
| 52 | D | D | D | D | D | D | A | A | A | C | B | B |

Many of the compounds showed excellent herbicidal activity against all tested species (Example 4, 8, 15, 18, 19, 26, 27, 28, 29, 31, 34, 39, 41, 43, 44 and 47).

The invention claimed is:
1. A compound of formula II:

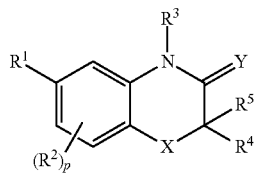

wherein
X is independently selected from $CR^6R^7$, $NR^8$, O, S, S(O) and $S(O)_2$;
Y is independently selected from O and S;
$R^1$ is independently selected from:

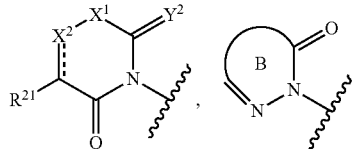

and $N=CR^{10}R^{11}$; wherein $R^{10}$ and $R^{11}$ together with the carbon atom to which they are attached form a 5- to 9-membered bicyclic or monocyclic heterocyclyl group, wherein said heterocyclyl group is optionally unsaturated; and wherein said heterocyclyl group comprises at least one nitrogen atom in the ring and is optionally substituted with from 1 to 6 $R^9$ groups;
wherein ====== is either a carbon-carbon double bond or a carbon-carbon single bond;
$=Y^2$ is $=O$ or $=S$;
$X^1$ is independently absent or is selected from $NR^{19}$ and $CR^{22}R^{22}$;
$X^2$ is independently absent or is $CR^{21}$;
ring B is a 5- or 6-membered heterocyclyl group; and wherein said heterocyclyl group is optionally fused to a 5- or 6-membered cycloalkyl or heterocycloalkyl ring and wherein the group $R^1$ is optionally substituted with from 1 to 5 $R^9$ groups;
$R^2$ is independently at each occurrence selected from $C_1$-$C_6$-alkyl, $C_1$-$C_6$-haloalkyl, halogen, nitro, $OR^{12}$, $SR^{13}$, $OS(O)_2R^{13}$, $S(O)_2R^{13}$, $S(O)_2NR^{13}R^{13}$, $S(O)(NR^{13})R^{13}$, $S(O)R^{13}$, cyano, $C_2$-$C_6$-alkenyl, $C_2$-$C_6$-alkynyl, and $NR^{13}R^{14}$;
$R^3$ is selected from $C_1$-$C_6$-alkyl, $C_1$-$C_6$-haloalkyl, $C_3$-$C_6$-cycloalkyl, $C_3$-$C_6$-alkenyl, $C_3$-$C_6$-alkynyl, 4- to 6-membered heterocycloalkyl, $C_2$-$C_3$-alkylene-$OR^{13a}$ and $C_1$-$C_3$-alkylene-$R^{3a}$; wherein $R^{3a}$ is selected from: cyano, 3- to 6-membered heterocycloalkyl, $C_3$-$C_6$-cycloalkyl and $CO_2R^{13a}$, $R^4$ and $R^5$ together with the carbon atom to which they are attached form a cyclic group selected from $C_3$-$C_6$-cycloalkyl and a 4- to 6-membered heterocycloalkyl, wherein said heterocycloalkyl group comprises at least one heteroatom selected from N, O and S; and wherein said cycloalkyl group or heterocycloalkyl group is optionally substituted with from 1 to 4 R'5 groups;

$R^6$, $R^7$ and $R^8$ are each independently selected from H, $C_1$-$C_6$-alkyl and $C_3$-$C_6$-cycloalkyl;

$R^9$ is independently at each occurrence selected from: =O, =S, =$NR^{13}$, $C_1$-$C_6$-alkyl, $C_1$-$C_6$-haloalkyl, halogen, nitro, $OR^{12}$, $SR^{13}$, $S(O)_2R^{13}$, $S(O)_2NR^{13}R^{13}$, $S(O)(NR^{13})R^{13}$, $S(O)R^{13}$, $C(O)R^{13}$, $C(O)NR^{13}R^{13}$, $C(O)OR^{13}$, cyano, $C_2$-$C_6$-alkenyl, $C_2$-$C_6$-alkynyl, and $NR^{13}R^{14}$;

$R^{12}$ is independently at each occurrence selected from: H, $C_1$-$C_6$-alkyl, $C_3$-$C_6$-cycloalkyl, $C_1$-$C_6$-haloalkyl and 4- to 6-membered heterocycloalkyl;

$R^{13}$ is independently at each occurrence selected from: H, benzyl, $C_3$-$C_6$-cycloalkyl and $C_1$-$C_6$-alkyl;

or where two $R^{13}$ groups are attached to the same nitrogen atom, said $R^{13}$ groups, together with said nitrogen atom form a 4-, 5-, 6- or 7-membered heterocycloalkyl ring;

$R^{13a}$ is independently selected from: H, $C_3$-$C_6$-cycloalkyl and $C_1$-$C_6$-alkyl;

$R^{14}$ is independently at each occurrence selected from: H, benzyl, $C_1$-$C_6$-alkyl, $C_3$-$C_6$-cycloalkyl, $C(O)$—$C_1$-$C_6$-alkyl, $S(O)_2$—$C_1$-$C_6$-alkyl and 4- to 6-membered heterocycloalkyl;

or where a $R^{13}$ group and a $R^{14}$ group are attached to the same nitrogen atom, said $R^{13}$ and $R^{14}$ groups, together with said nitrogen atom form a 4-, 5-, 6- or 7-membered heterocycloalkyl ring;

$R^{15}$ is independently at each occurrence selected from: =O, =S, =$NR^{13}$, $C_1$-$C_6$-alkyl, $C_1$-$C_6$-haloalkyl, halogen, nitro, $OR^{12}$, $SR^{13}$, $S(O)_2R^{13}$, $S(O)_2NR^{13}R^{13}$, $S(O)(NR^{13})R^{13}$, $S(O)R^{13}$, $C(O)R^{13}$, $C(O)NR^{13}R^{13}$, $C(O)OR^{13}$, cyano, $C_2$-$C_6$-alkenyl, $C_2$-$C_6$-alkynyl, and $NR^{13}R^{14}$;

$R^{19}$ is independently selected from H, $C_1$-$C_6$-alkyl, $C_1$-$C_6$-haloalkyl, $C_3$-$C_6$-cycloalkyl, $C_3$-$C_6$-alkenyl, $C_3$-$C_6$-alkynyl, 4- to 6-membered heterocycloalkyl, $C_2$-$C_3$-alkylene-$OR^{13}$a and $C_1$-$C_3$-alkylene-$R^{19a}$; wherein $R^{19a}$ is selected from: cyano, 3- to 6-membered heterocycloalkyl, $C_3$-$C_6$-cycloalkyl and $CO_2R^{13a}$;

$R^{21}$ is independently selected from H, halo, $C_1$-$C_4$-alkyl and $C_1$-$C_4$-haloalkyl;

or two $R^{21}$ groups, together with the carbon atoms to which they are attached form a phenyl ring, a $C_3$-$C_6$-cycloalkyl ring, 5- to 7-membered heterocycloalkyl ring or a 5- or 6-membered bridged bicyclic cycloalkyl or cycloalkenyl ring system, said ring or ring system being optionally substituted with from 1 to 6 $R^9$ groups;

or $R^{19}$ and one $R^{21}$ group, together with the nitrogen and carbon atoms to which they are attached form a 5- to 7-membered heterocycloalkyl ring, said ring being optionally substituted with from 1 to 6 $R^9$ groups;

$R^{22}$ is independently at each occurrence selected from H and $C_1$-$C_4$-alkyl; and p is an integer selected from 0, 1, 2 and 3;

wherein any abovementioned alkyl, alkenyl, alkynyl, alkylene, cycloalkyl, heterocycloalkyl (including where two $R^{13}$ groups or an $R^{13}$ group and an $R^{14}$ group together with a nitrogen to which they are attached form a heterocycloalkyl ring) group is optionally substituted, where chemically possible, by 1 to 4 substituents which are each independently selected at each occurrence from the group consisting of: =O; =$NR^a$, =$NOR^a$, $C_1$-$C_4$-alkyl, halo, nitro, cyano, $C_1$-$C_4$-haloalkyl, $C_2$-$C_4$-alkenyl, $C_2$-$C_4$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$ and $OR^a$;

wherein $R^a$ is independently selected from H and $C_1$-$C_4$-alkyl; and $R^b$ is independently H, $C(O)$—$C_1$-$C_4$-alkyl, $S(O)_2$—$C_1$-$C_4$-alkyl; or an agronomically acceptable salt or N-oxide thereof.

2. A compound of claim 1 wherein X is selected from O and S.

3. A compound of claim 1, wherein Y is O.

4. A compound of claim 1, wherein $R^1$ has the structure:

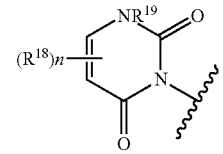

wherein $R^{18}$ is independently at each occurrence selected from $C_1$-$C_4$-alkyl, $C_1$-$C_4$-haloalkyl, halogen, nitro, $OR^{12}$, $SR^{13}$, cyano, $C_2$-$C_4$-alkenyl, $C_2$-$C_4$-alkynyl and $NR^{13}R^{14}$; and n is an integer independently selected from 0, 1 and 2; wherein where n is 2, the two $R^{18}$ groups may together with the carbon atoms to which they are attached form a benzene ring.

5. A compound of claim 1, wherein $R^1$ has the structure:

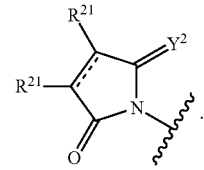

6. A compound of claim 1, wherein $R^1$ has the structure:

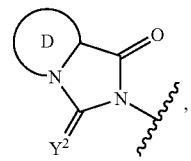

wherein ring D is a 5- to 7-membered heterocycloalkyl ring, said ring being optionally substituted with from 1 to 6 $R^9$ groups.

7. A compound of claim 1, wherein $R^1$ has the structure:

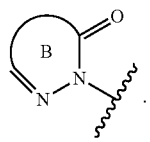

8. A compound of claim 1, wherein $R^3$ is selected from $C_1$-$C_6$-alkyl, $C_3$-$C_6$-alkenyl, $C_3$-$C_6$-alkynyl, $C_2$-$C_3$-alkylene-$OR^{13a}$ and $C_1$-$C_3$-alkylene-$R^{3a}$; wherein $R^{3a}$ is selected from: cyano, 3- to 6-membered heterocycloalkyl, $C_3$-$C_6$-cycloalkyl and $CO_2R^{13a}$.

9. A compound of claim 8, wherein $R^3$ is selected from propargyl, $CH_2$-cyclopropyl, $CH(Me)C(O)OR^{13a}$ and $CH_2CH_2OMe$.

10. A compound of claim 1, wherein $R^4$ and $R^5$ together with the carbon atom to which they are attached form a $C_3$-$C_6$-cycloalkyl group; wherein the cycloalkyl group is optionally substituted with from 1 to 4 $R^{15}$ groups.

11. A compound of claim 10, wherein $R^4$ and $R^5$ together with the carbon atom to which they are attached form a cyclopropyl group; wherein the cyclopropyl group is optionally substituted with from 1 to 4 $R^{15}$ groups.

12. A compound of claim 1, wherein $R^4$ and $R^5$, together with the carbon to which they are attached have the structure:

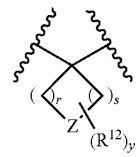

wherein Z is independently selected from —$NR^{16}$—, —O—, —S(O)—, —$S(O)_2$—, —$S(O)NR^{17}$— and —S—; $R^{16}$ is independently selected from H, $C_1$-$C_4$-alkyl, $S(O)_2R^{13}$, $C(O)R^{13}$, $C_3$-$C_4$-alkenyl and $C_3$-$C_4$-alkynyl; $R^{17}$ is independently selected from H, $C_1$-$C_4$-alkyl, $C_3$-$C_4$-alkenyl and $C_3$-$C_4$-alkynyl; y is an integer selected from 0, 1, 2 and 3; r and s are each an integer selected from 1, 2 and 3; and wherein the sum of r and s is 2, 3 or 4.

13. A compound of claim 12, wherein Z is $NR^{16}$.

14. A compound of claim 12, wherein Z is O.

15. A compound of claim 12, wherein the sum of r and s is 2.

16. A compound of claim 12, wherein the sum of r and s is 3.

17. A compound of claim 12, wherein the sum of r and s is 4.

18. A compound of claim 1, wherein p is 1 and the single $R^2$ substituent is situated para to the nitrogen that is also attached to $R^3$.

19. A compound of claim 1, wherein the compound of formula (I) is selected from:

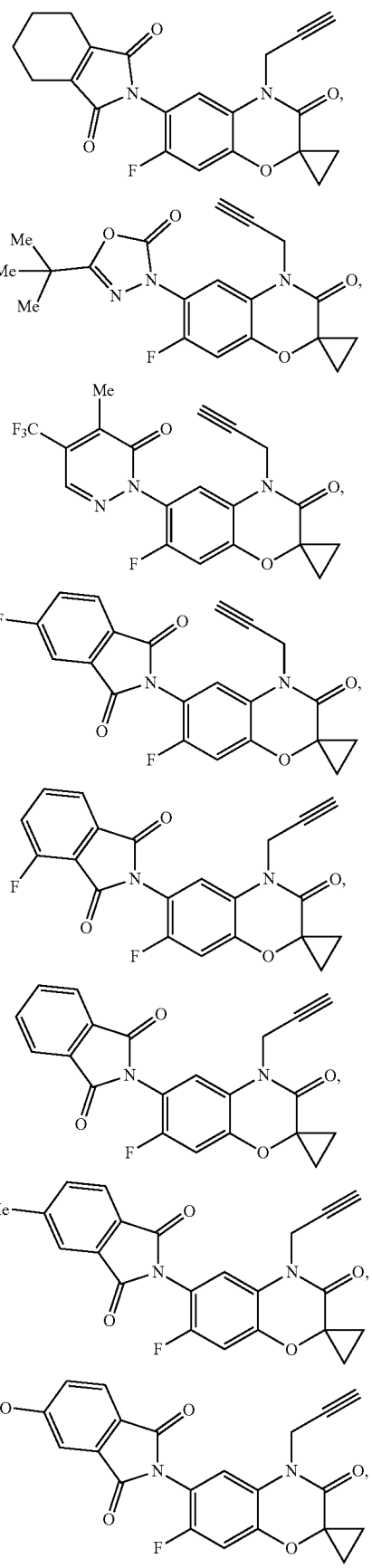

-continued
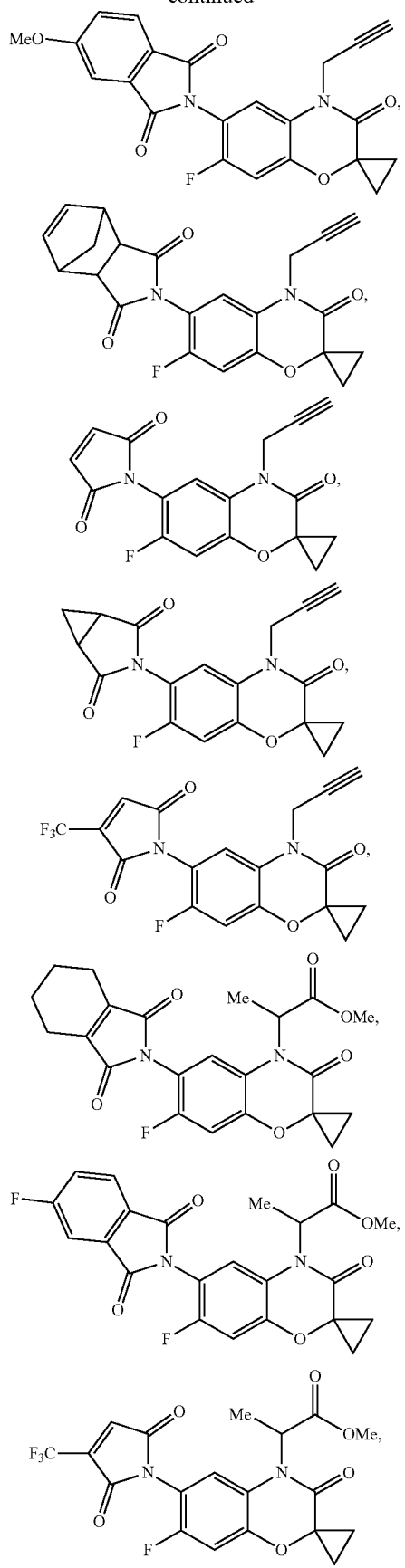
-continued
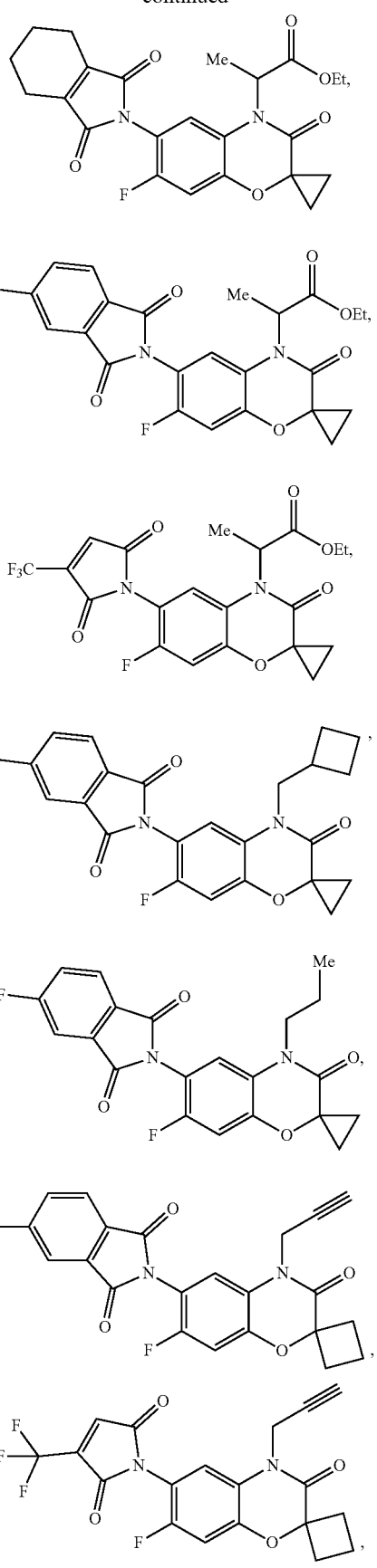

107
-continued
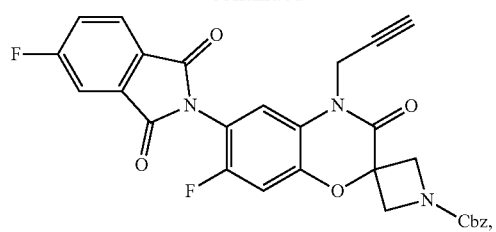
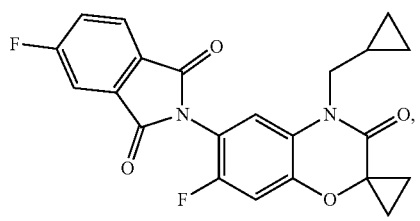
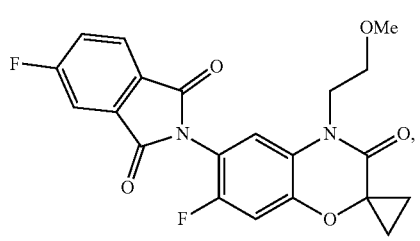
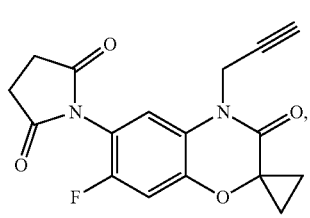
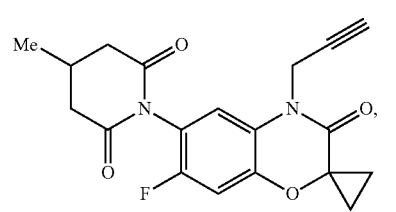
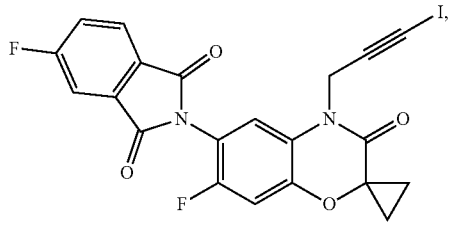
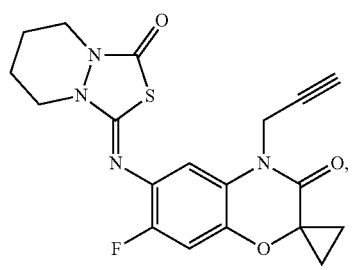
108
-continued
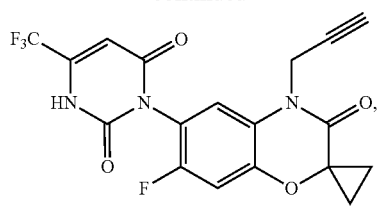
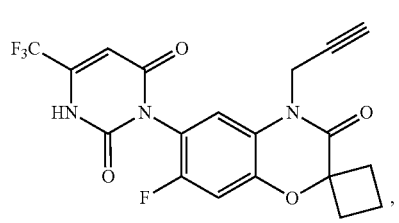
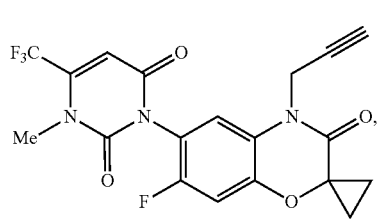
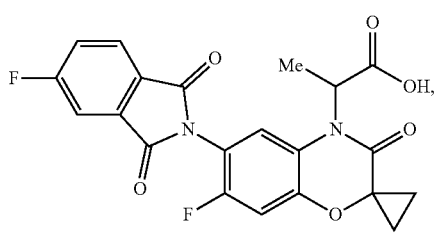
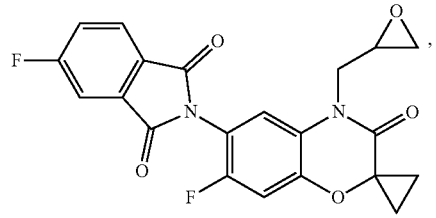
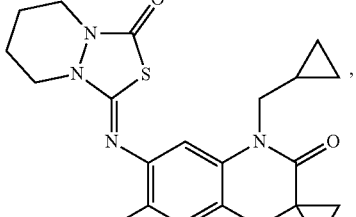
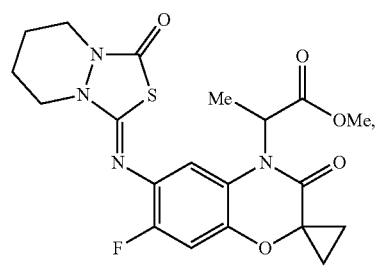

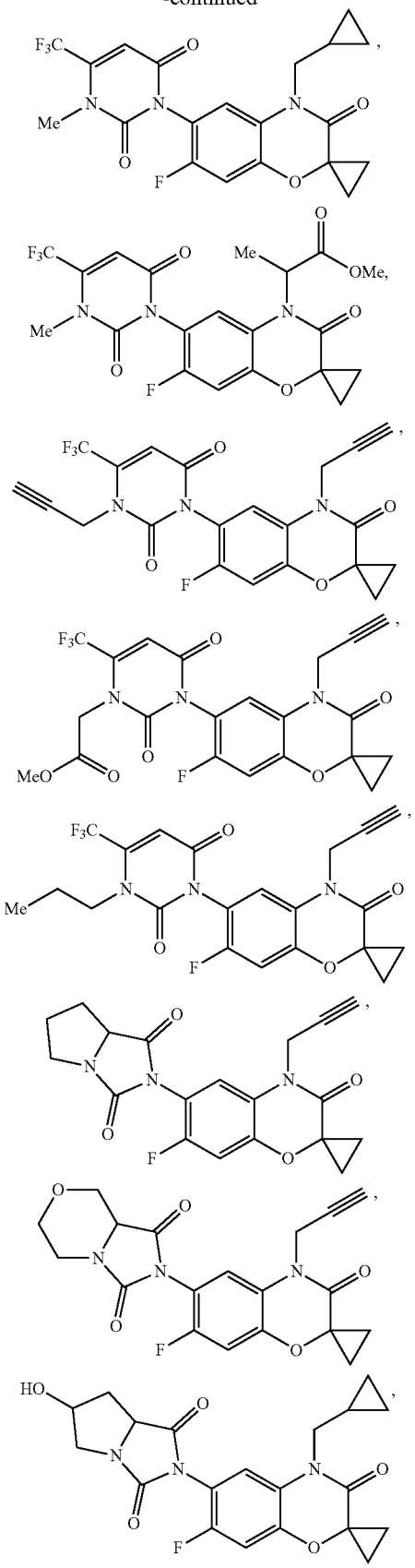
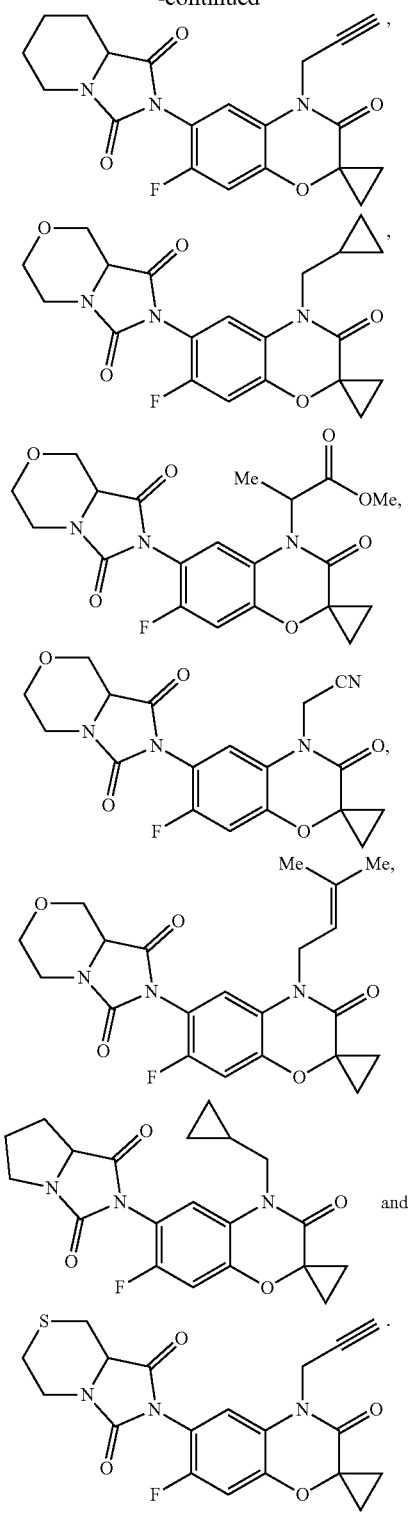
20. A herbicidal composition comprising a herbicidally effective amount of an active compound of claim 1.
21. A method for controlling weeds, the method comprising applying a compound of claim 1 to the plants or to the area where it is intended that the plants will grow.
* * * * *